(12) United States Patent
Brotherton-Pleiss et al.

(10) Patent No.: US 8,889,682 B2
(45) Date of Patent: Nov. 18, 2014

(54) INHIBITORS OF BRUTON'S TYROSINE KINASE

(75) Inventors: Christine E. Brotherton-Pleiss, Sunnyvale, CA (US); Saul Jaime-Figueroa, Morris Plains, NJ (US); Francisco Javier Lopez-Tapia, Mahwah, NJ (US); Yan Lou, Glen Ridge, NJ (US); Timothy D. Owens, San Carlos, CA (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/586,958

(22) Filed: Aug. 16, 2012

(65) Prior Publication Data

US 2013/0045965 A1 Feb. 21, 2013

Related U.S. Application Data

(60) Provisional application No. 61/524,374, filed on Aug. 17, 2011, provisional application No. 61/649,991, filed on May 22, 2012.

(51) Int. Cl.
*A61K 31/501* (2006.01)
*A61K 31/502* (2006.01)
*C07D 237/02* (2006.01)
*C07D 413/14* (2006.01)

(52) U.S. Cl.
USPC .......................................... 514/248; 544/239

(58) Field of Classification Search
CPC . A61K 31/501; A61K 31/495; C07D 401/14; C07D 237/30; A01N 43/50
USPC ............................ 544/237, 238, 239; 514/248
See application file for complete search history.

(56) References Cited

U.S. PATENT DOCUMENTS

2010/0222325 A1 9/2010 Berthel et al.

FOREIGN PATENT DOCUMENTS

WO 2009/098144 8/2009

OTHER PUBLICATIONS (International Search Report PCT/EP2012/065844 Oct. 1, 2012).

*Primary Examiner* — Paul V. Ward

(57) ABSTRACT

This application discloses compounds according to generic Formula I:

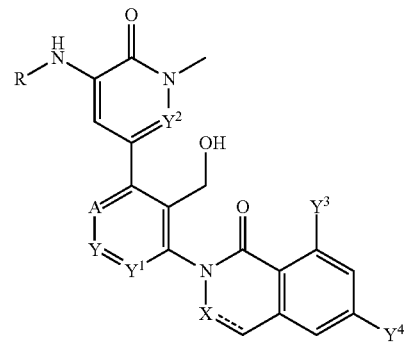

wherein the variables are defined as described herein, and which inhibit Btk. The compounds disclosed herein are useful to modulate the activity of Btk and treat diseases associated with excessive Btk activity. The compounds are further useful to treat inflammatory and auto immune diseases associated with aberrant B-cell proliferation, such as rheumatoid arthritis. Also disclosed are compositions containing compounds of Formula I and at least one carrier, diluent or excipient.

10 Claims, No Drawings

INHIBITORS OF BRUTON'S TYROSINE KINASE

PRIORITY TO RELATED APPLICATIONS

This application is entitled to the benefit of U.S. provisional patent application Ser. No. 61/649,991 filed on May 22, 2012, and U.S. provisional patent application Ser. No. 61/524,374 filed on Aug. 17, 2011.

FIELD OF THE INVENTION

The present invention relates to the use of novel derivatives which inhibit Btk and are useful for the treatment of autoimmune and inflammatory diseases caused by aberrant B-cell activation. The novel compounds described herein are useful for the treatment of rheumatoid arthritis and asthma.

Protein kinases constitute one of the largest families of human enzymes and regulate many different signaling processes by adding phosphate groups to proteins (T. Hunter, *Cell* 1987 50:823-829). Specifically, tyrosine kinases phosphorylate proteins on the phenolic moiety of tyrosine residues. The tyrosine kinase family includes members that control cell growth, migration, and differentiation. Abnormal kinase activity has been implicated in a variety of human diseases including cancers, autoimmune and inflammatory diseases. Since protein kinases are among the key regulators of cell signaling they provide a target to modulate cellular function with small molecular kinase inhibitors and thus make good drug design targets. In addition to treatment of kinase-mediated disease processes, selective and efficacious inhibitors of kinase activity are also useful for investigation of cell signaling processes and identification of other cellular targets of therapeutic interest.

There is good evidence that B-cells play a key role in the pathogenesis of autoimmune and/or inflammatory disease. Protein-based therapeutics that deplete B cells such as Rituxan are effective against autoantibody-driven inflammatory diseases such as rheumatoid arthritis (Rastetter et al. *Annu Rev Med* 2004 55:477). Therefore inhibitors of the protein kinases that play a role in B-cell activation should be useful therapeutics for B-cell mediated disease pathology such as autoantibody production.

Signaling through the B-cell receptor (BCR) controls a range of B-cell responses including proliferation and differentiation into mature antibody producing cells. The BCR is a key regulatory point for B-cell activity and aberrant signaling can cause deregulated B-cell proliferation and formation of pathogenic autoantibodies that lead to multiple autoimmune and/or inflammatory diseases. Bruton's Tyrosine Kinase (Btk) is a non-BCR associated kinase that is membrane proximal and immediately downstream from BCR. Lack of Btk has been shown to block BCR signaling and therefore inhibition of Btk could be a useful therapeutic approach to block B-cell mediated disease processes.

Btk is a member of the Tec family of tyrosine kinases, and has been shown to be a critical regulator of early B-cell development and mature B-cell activation and survival (Khan et al. *Immunity* 1995 3:283; Ellmeier et al. J. Exp. Med. 2000 192:1611). Mutation of Btk in humans leads to the condition X-linked agammaglobulinemia (XLA) (reviewed in Rosen et al. *New Eng. J. Med.* 1995 333:431 and Lindvall et al. *Immunol. Rev.* 2005 203:200). These patients are immunocompromised and show impaired maturation of B-cells, decreased immunoglobulin and peripheral B-cell levels, diminished T-cell independent immune responses as well as attenuated calcium mobilization following BCR stimulation.

Evidence for a role for Btk in autoimmune and inflammatory diseases has also been provided by Btk-deficient mouse models. In preclinical murine models of systemic lupus erythematosus (SLE), Btk-deficient mice show marked amelioration of disease progression. In addition, Btk-deficient mice are resistant to collagen-induced arthritis (Jansson and Holmdahl *Clin. Exp. Immunol.* 1993 94:459). A selective Btk inhibitor has been demonstrated dose-dependent efficacy in a mouse arthritis model (Z. Pan et al., *Chem. Med. Chem.* 2007 2:58-61).

Btk is also expressed by cells other than B-cells that may be involved in disease processes. For example, Btk is expressed by mast cells and Btk-deficient bone marrow derived mast cells demonstrate impaired antigen induced degranulation (Iwaki et al. *J. Biol. Chem.* 2005 280:40261). This shows Btk could be useful to treat pathological mast cells responses such as allergy and asthma. Also monocytes from XLA patients, in which Btk activity is absent, show decreased TNF alpha production following stimulation (Horwood et al. *J Exp Med* 197:1603, 2003). Therefore TNF alpha mediated inflammation could be modulated by small molecular Btk inhibitors. Also, Btk has been reported to play a role in apoptosis (Islam and Smith *Immunol. Rev.* 2000 178:49,) and thus Btk inhibitors would be useful for the treatment of certain B-cell lymphomas and leukemias (Feldhahn et al. *J. Exp. Med.* 2005 201:1837).

SUMMARY OF THE INVENTION

The present application provides the Btk inhibitor compounds of Formula I, methods of use thereof, as described herein below:

The application provides a compound of Formula I,

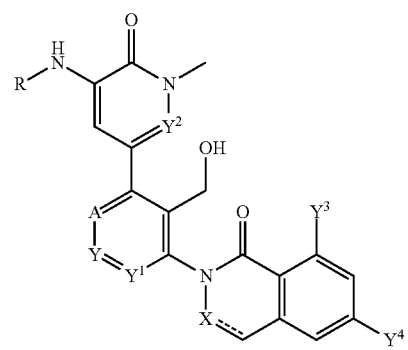

I wherein:
═ is either a single or double bond;
each X is independently CH, CH$_2$, CHX', or N;
X' is lower alkyl;
R is H, —R$^1$, —R$^1$—R$^2$—R$^3$, —R$^1$—R$^3$, or —R$^2$—R$^3$;
R$^1$ is aryl, heteroaryl, bicyclic heteroaryl, cycloalkyl, heterocycloalkyl, or bicyclic heterocycle, each of which is optionally substituted with one or more lower alkyl, hydroxy, hydroxy lower alkyl, lower alkoxy, halo, nitro, amino, amido, cyano, oxo, or lower haloalkyl;
R$^2$ is —C(═O), —C(═O)O, —C(═O)NR$^{2'}$, —NHC(═O) O, —C(R$^{2'}$)$_2$, —O, —S, —C(═NH)NR$^{2'}$, or —S(═O)$_2$;
each R$^{2'}$ is independently H or lower alkyl;
R$^3$ is H or R$^4$;
R$^4$ is lower alkyl, lower haloalkyl, lower alkoxy, amino, lower alkyl amino, cycloalkyl amino, lower dialkyl amino, aryl, arylalkyl, alkylaryl, heteroaryl, lower alkyl heteroaryl, heteroaryl lower alkyl, cycloalkyl, lower alkyl cycloalkyl, cycloalkyl lower alkyl, heterocycloalkyl, lower alkyl heterocycloalkyl, heterocycloalkyl lower alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring;

each of A, Y, and $Y^1$ is CH or N, with the proviso that at least one of A, Y, and $Y^1$ must be N;

$Y^2$ is CH or N;

$Y^3$ is H or F;

$Y^4$ is $Y^{4a}$; $Y^{4b}$, $Y^{4c}$, or $Y^{4d}$;

$Y^{4a}$ is H or halogen;

$Y^{4b}$ is lower alkyl, optionally substituted with one or more substituents selected from the group consisting of lower haloalkyl, halogen, hydroxy, amino, cyano, and lower alkoxy;

$Y^{4c}$ is lower cycloalkyl, optionally substituted with one or more substituents selected from the group consisting of lower alkyl, lower haloalkyl, halogen, hydroxy, amino, cyano, and lower alkoxy; and $Y^{4d}$ is amino, optionally substituted with one or more lower alkyl, alkoxy lower alkyl, or hydroxy lower alkyl;

or a pharmaceutically acceptable salt thereof.

The application provides a method for treating an inflammatory and/or autoimmune condition comprising administering to a patient in need thereof a therapeutically effective amount of the Btk inhibitor compound of Formula I.

The application provides a pharmaceutical composition comprising the Btk inhibitor compound of any one of Formula I, admixed with at least one pharmaceutically acceptable carrier, excipient or diluent.

DETAILED DESCRIPTION OF THE INVENTION

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

As used herein, unless specifically indicated otherwise, the word "or" is used in the "inclusive" sense of "and/or" and not the "exclusive" sense of "either/or".

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or "------" drawn through a bond each refer to the point of attachment of a functional group or other chemical moiety to the rest of the molecule of which it is a part. Thus, for example:

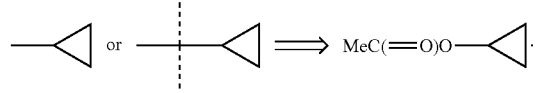

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen atom or a substituent.

The phrase "optional bond" means that the bond may or may not be present, and that the description includes single, double, or triple bonds. If a substituent is designated to be a "bond" or "absent", the atoms linked to the substituents are then directly connected.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Certain compounds of Formulae I may exhibit tautomerism. Tautomeric compounds can exist as two or more inter-convertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (het)aryl refers to either an aryl or a heteroaryl group.

The term "spirocycloalkyl", as used herein, means a spirocyclic cycloalkyl group, such as, for example, spiro[3.3]heptane. The term spiroheterocycloalkyl, as used herein, means a spirocyclic heterocycloalkyl, such as, for example, 2,6-diaza spiro[3.3]heptane.

The term "acyl" as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl refers to a group —C(=O)R contain 6 carbon atoms. The term "arylcarbonyl" as used herein means a group of formula C(=O)R wherein R is an aryl group; the term "benzoyl" as used herein an "arylcarbonyl" group wherein R is phenyl.

The term "ester" as used herein denotes a group of formula —C(=O)OR wherein R is lower alkyl as defined herein.

The term "alkyl" as used herein denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as used herein refers to an alkyl composed of 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"-, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical.

The terms "haloalkyl" or "halo-lower alkyl" or "lower haloalkyl" refers to a straight or branched chain hydrocarbon residue containing 1 to 6 carbon atoms wherein one or more carbon atoms are substituted with one or more halogen atoms.

The term "alkylene" or "alkylenyl" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH(i-Pr)CH$_2$—), unless otherwise indicated. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The term "PCy$_3$" refers to a phosphine trisubstituted with three cyclic moieties.

The terms "haloalkoxy" or "halo-lower alkoxy" or "lower haloalkoxy" refers to a lower alkoxy group, wherein one or more carbon atoms are substituted with one or more halogen atoms.

The term "hydroxyalkyl" as used herein denotes an alkyl radical as herein defined wherein one to three hydrogen atoms on different carbon atoms is/are replaced by hydroxyl groups.

The terms "alkylsulfonyl" and "arylsulfonyl" as used herein refers to a group of formula —S(=O)$_2$R wherein R is alkyl or aryl respectively and alkyl and aryl are as defined herein. The term "heteroalkylsulfonyl" as used herein refers herein denotes a group of formula —S(=O)$_2$R wherein R is "heteroalkyl" as defined herein.

The terms "alkylsulfonylamino" and "arylsulfonylamino" as used herein refers to a group of formula —NR'S(=O)$_2$R wherein R is alkyl or aryl respectively, R' is hydrogen or $C_{1-3}$ alkyl, and alkyl and aryl are as defined herein.

The term "cycloalkyl" as used herein refers to a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to a cycloalkyl composed of 3 to 7 carbons in the carbocyclic ring.

The term carboxy-alkyl as used herein refers to an alkyl moiety wherein one, hydrogen atom has been replaced with a carboxyl with the understanding that the point of attachment of the heteroalkyl radical is through a carbon atom. The term "carboxy" or "carboxyl" refers to a —CO$_2$H moiety.

The term "heteroaryl" or "heteroaromatic" as used herein means a monocyclic or bicyclic radical of 5 to 12 ring atoms having at least one aromatic or partially unsaturated ring containing four to eight atoms per ring, incorporating one or more N, O, or S heteroatoms, the remaining ring atoms being carbon, with the understanding that the attachment point of the heteroaryl radical will be on an aromatic or partially unsaturated ring. As well known to those skilled in the art, heteroaryl rings have less aromatic character than their all-carbon counter parts. Thus, for the purposes of the invention, a heteroaryl group need only have some degree of aromatic character. Examples of heteroaryl moieties include monocyclic aromatic heterocycles having 5 to 6 ring atoms and 1 to 3 heteroatoms include, but is not limited to, pyridinyl, pyrimidinyl, pyrazinyl, oxazinyl, pyrrolyl, pyrazolyl, imidazolyl, oxazolyl, 4,5-Dihydro-oxazolyl, 5,6-Dihydro-4H-[1,3]oxazolyl, isoxazole, thiazole, isothiazole, triazoline, thiadiazole and oxadiaxoline which can optionally be substituted with one or more, preferably one or two substituents selected from hydroxy, cyano, alkyl, alkoxy, thio, lower haloalkoxy, alkylthio, halo, lower haloalkyl, alkylsulfinyl, alkylsulfonyl, halogen, amino, alkylamino, dialkylamino, aminoalkyl, alkylaminoalkyl, and dialkylaminoalkyl, nitro, alkoxycarbonyl and carbamoyl, alkylcarbamoyl, dialkylcarbamoyl, arylcarbamoyl, alkylcarbonylamino and arylcarbonylamino. Examples of bicyclic moieties include, but are not limited to, 4,5,6,7-tetrahydro-pyrazolo[1,5-a]pyrazin-2-yl, quinolinyl, isoquinolinyl, benzofuryl, benzothiophenyl, benzoxazole, benzisoxazole, benzothiazole, naphthyridinyl, 5,6,7,8-Tetrahydro-[1,6]naphthyridinyl, and benzisothiazole. Bicyclic moieties can be optionally substituted on either ring, however the point of attachment is on a ring containing a heteroatom.

The term "heterocyclyl", "heterocycloalkyl" or "heterocycle" as used herein denotes a monovalent saturated cyclic radical, consisting of one or more rings, preferably one to two rings, including spirocyclic ring systems, of three to eight atoms per ring, incorporating one or more ring heteroatoms (chosen from N,O or $S(O)_{0-2}$), and which can optionally be independently substituted with one or more, preferably one or two substituents selected from hydroxy, oxo, cyano, lower alkyl, lower alkoxy, lower haloalkoxy, alkylthio, halo, lower haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, and ionic forms thereof, unless otherwise indicated. Examples of heterocyclic radicals include, but are not limited to, morpholinyl, piperazinyl, piperidinyl, azetidinyl, pyrrolidinyl, hexahydroazepinyl, oxetanyl, tetrahydrofuranyl, tetrahydrothiophenyl, oxazolidinyl, thiazolidinyl, isoxazolidinyl, tetrahydropyranyl, thiomorpholinyl, quinuclidinyl and imidazolinyl, and ionic forms thereof. Examples may also be bicyclic, such as, for example, 3,8-diaza-bicyclo[3.2.1]octane, 2,5-diaza-bicyclo[2.2.2]octane, or octahydro-pyrazino[2,1-c][1,4]oxazine.

Inhibitors of Btk

This application is related to U.S. Pat. No. 7,902,194, filed on Jun. 24, 2009, U.S. patent application Ser. No. 12/711,312, filed on Feb. 24, 2010, and U.S. patent application Ser. No. 12/978, 187, filed on Jan. 10, 2011, the disclosures of which are incorporated herein by reference in its entirety.

The compounds of generic Formula I, as described herein, incorporating the replacement of the standard aryl ring linker with pyridyl in the linker position gives clearly differentiated and unexpectedly improved properties, such as: 1.) general increases in solubility, 2.) increasing evenness in polarity distribution throughout the scaffold, as amphiphilic vector is less pronounced, and 3) general improvement in plasma protein binding, resulting in increase in the free concentration of drug in human and rat plasma.

The application provides a compound of Formula I,

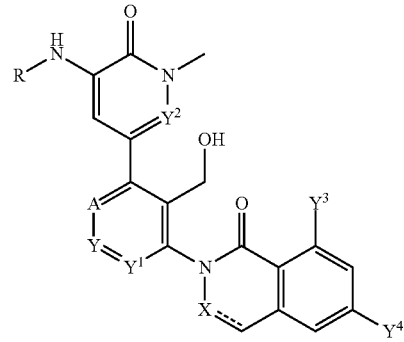

I wherein:
= is either a single or double bond;
each X is independently CH, $CH_2$, CHX', or N;
X' is lower alkyl;
R is H, —$R^1$, —$R^1$—$R^2$—$R^3$, —$R^1$—$R^3$, or —$R^2$—$R^3$;
$R^1$ is aryl, heteroaryl, bicyclic heteroaryl, cycloalkyl, heterocycloalkyl, or bicyclic heterocycle, each of which is optionally substituted with one or more lower alkyl, hydroxy, hydroxy lower alkyl, lower alkoxy, halo, nitro, amino, amido, cyano, oxo, or lower haloalkyl;
$R^2$ is —C(=O), —C(=O)O, —C(=O)$NR^{2'}$, —NHC(=O)O, —C($R^{2'}$)$_2$, —O, —S, —C(=NH)$NR^{2'}$, or —S(=O)$_2$;
each $R^{2'}$ is independently H or lower alkyl;
$R^3$ is H or $R^4$;
$R^4$ is lower alkyl, lower haloalkyl, lower alkoxy, amino, lower alkyl amino, cycloalkyl amino, lower dialkyl amino, aryl, arylalkyl, alkylaryl, heteroaryl, lower alkyl heteroaryl, heteroaryl lower alkyl, cycloalkyl, lower alkyl cycloalkyl, cycloalkyl lower alkyl, heterocycloalkyl, lower alkyl heterocycloalkyl, heterocycloalkyl lower alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring;
each of A, Y, and $Y^1$ is CH or N, with the proviso that at least one of A, Y, and $Y^1$ must be N;
$Y^2$ is CH or N;
$Y^3$ is H or F;
$Y^4$ is $Y^{4a}$, $Y^{4b}$, $Y^{4c}$, or $Y^{4d}$;
$Y^{4a}$ is H or halogen;
$Y^{4b}$ is lower alkyl, optionally substituted with one or more substituents selected from the group consisting of lower haloalkyl, halogen, hydroxy, amino, cyano, and lower alkoxy;
$Y^{4c}$ is lower cycloalkyl, optionally substituted with one or more substituents selected from the group consisting of lower alkyl, lower haloalkyl, halogen, hydroxy, amino, cyano, and lower alkoxy; and
$Y^{4d}$ is amino, optionally substituted with one or more lower alkyl, alkoxy lower alkyl, or hydroxy lower alkyl;
or a pharmaceutically acceptable salt thereof.

The application provides a compound of Formula I, wherein X is CH.

The application provides a compound of Formula I, wherein X is N.

The application provides a compound of Formula I, wherein ═ is a double bond.

The application provides a compound of Formula I, wherein ═ is a single bond.

The application provides a compound of Formula I, wherein ═ is a double bond and X is CH.

The application provides a compound of Formula I, wherein ═ is a single bond and i X is $CH_2$.

The application provides a compound of Formula I, wherein ═ is a single bond and i X is CHR'.

The application provides a compound of Formula I, wherein ═ is a double bond and i X is N.

The application provides a compound of Formula I, wherein ═ is a single bond and i X is NH.

The application provides a compound of Formula I, wherein ═ is a single bond and i X is NR'.

The application provides a compound of Formula I, wherein A is CH, Y is CH, and $Y^1$ is N.

The application provides a compound of Formula I, wherein A is N, Y is CH, and $Y^1$ is CH.

The application provides a compound of Formula I, wherein A is CH, Y is N, and $Y^1$ is CH.

The application provides a compound of Formula I, wherein ═ is a double bond, X is i N, A is CH, Y is CH, and $Y^1$ is N.

The application provides a compound of Formula I, wherein X is CH, A is CH, Y is CH and $Y^1$ is N.

The application provides a compound of Formula I, wherein X is CH, A is CH, Y is CH and $Y^1$ is N.

The application provides a compound of Formula I, wherein $Y^3$ is H, ═ is a double bond, X is N, A is CH, Y is CH and $Y^1$ is N.

The application provides a compound of Formula I, wherein $Y^3$ is F, ═ is a double bond, X is N, A is CH, Y is CH and $Y^1$ is N.

The application provides a compound of Formula I, wherein $Y^4$ is tert-butyl, $Y^3$ is F, ═ is a double bond, X is N, A is CH, Y is CH and $Y^1$ is N.

The application provides a compound of Formula I, wherein $Y^2$ is CH.

The application provides a compound of Formula I, wherein $Y^2$ is N.

The application provides a compound of Formula I, wherein Y is N and $Y^1$ is CH.

The application provides a compound of Formula I, wherein $Y^2$ is CH, Y is N and $Y^1$ is CH.

The application provides a compound of Formula I, wherein ═ is a double bond, X is i N, $Y^2$ is CH, Y is N and $Y^1$ is CH.

The application provides a compound of Formula I, wherein $Y^3$ is H.

The application provides a compound of Formula I, wherein $Y^3$ is F.

The application provides a compound of Formula I, wherein ═ is a double bond, X is N and $Y^3$ is F.

The application provides a compound of Formula I, wherein $Y^4$ is cyclopropyl.

The application provides a compound of Formula I, wherein ═ is a double bond, X is N and $Y^4$ is cyclopropyl.

The application provides a compound of Formula I, wherein $Y^3$ is F and $Y^4$ is cyclopropyl.

The application provides a compound of Formula I, wherein ═ is a double bond, X is N, $Y^3$ is F, and $Y^4$ is cyclopropyl.

The application provides a compound of Formula I, wherein $Y^4$ is dimethylamino.

The application provides a compound of Formula I, wherein ═ is a double bond, X is N and $Y^4$ is dimethylamino.

The application provides a compound of Formula I, wherein $Y^3$ is F and $Y^4$ is dimethylamino.

The application provides a compound of Formula I, wherein ═ is a double bond, X is N, $Y^3$ is F, and $Y^4$ is dimethylamino.

The application provides a compound of Formula I, wherein $Y^4$ is tert-butyl.

The application provides a compound of Formula I, wherein ═ is a double bond, X is N and $Y^4$ is tert-butyl.

The application provides a compound of Formula I, wherein $Y^3$ is F and $Y^4$ is tert-butyl.

The application provides a compound of Formula I, wherein ═ is a double bond, X is N, $Y^3$ is F, and $Y^4$ is tert-butyl.

The application provides a compound of Formula I, wherein R is —$R^1$—$R^2$—$R^3$, $R^1$ is pyridyl, $R^2$ is —C(═O), and $R^3$ is morpholinyl.

The application provides a compound of Formula I, wherein R is —$R^1$—$R^2$—$R^3$, $R^1$ is pyridyl, $R^2$ is —C(═O), $R^3$ is morpholinyl and $Y^4$ is tert-butyl.

The application provides a compound of Formula I, wherein R is —$R^1$—$R^2$—$R^3$, $R^1$ is pyridyl, $R^2$ is —C(═O), $R^3$ is morpholinyl, ═ is a double bond, X is N, and $Y^4$ is tert-butyl.

The application provides a compound of Formula I, wherein R is —$R^1$—$R^2$—$R^3$, $R^1$ is pyridyl, $R^2$ is —C(═O), $R^3$ is morpholinyl, $Y^3$ is F and $Y^4$ is tert-butyl.

The application provides a compound of Formula I, wherein R is —$R^1$—$R^2$—$R^3$, $R^1$ is pyridyl, $R^2$ is —C(═O), $R^3$ is morpholinyl, ═ is a double bond, X is N, $Y^3$ is F, and $Y^4$ is tert-butyl.

The application provides a compound of Formula I, wherein R is $R^1$ and $R^1$ is 4,5,6,7-tetrahydro-pyrazolo[1,5-a]pyrazin-2-yl, optionally substituted with lower alkyl, heterocycloalkyl, cycloalkyl, or cycloalkyl lower alkyl.

The application provides a compound of Formula I, wherein R is $R^1$ and $R^1$ is 4,5,6,7-tetrahydro-pyrazolo[1,5-a]pyrazin-2-yl, optionally substituted with lower alkyl, heterocycloalkyl, cycloalkyl, or cycloalkyl lower alkyl, and $Y^4$ is tert-butyl.

The application provides a compound of Formula I, wherein R is $R^1$ and $R^1$ is 4,5,6,7-tetrahydro-pyrazolo[1,5-a]pyrazin-2-yl, optionally substituted with lower alkyl, heterocycloalkyl, cycloalkyl, or cycloalkyl lower alkyl, ═ is a double bond, X is N, and $Y^4$ is tert-butyl.

The application provides a compound of Formula I, wherein R is $R^1$ and $R^1$ is 4,5,6,7-tetrahydro-pyrazolo[1,5-a]pyrazin-2-yl, optionally substituted with lower alkyl, heterocycloalkyl, cycloalkyl, or cycloalkyl lower alkyl, $Y^3$ is F, and $Y^4$ is tert-butyl.

The application provides a compound of Formula I, wherein R is $R^1$ and $R^1$ is 4,5,6,7-tetrahydro-pyrazolo[1,5-a]pyrazin-2-yl, optionally substituted with lower alkyl, heterocycloalkyl, cycloalkyl, or cycloalkyl lower alkyl, ═ is a double bond, X is N, $Y^3$ is F, and $Y^4$ is tert-butyl.

The application provides a compound of Formula I, wherein R is —$R^1$—$R^3$, $R^1$ is pyridyl, and $R^3$ is lower alkyl heterocycloalkyl.

The application provides a compound of Formula I, wherein R is —R¹—R³, R¹ is pyridyl, R³ is lower alkyl heterocycloalkyl, and Y⁴ is tert-butyl.

The application provides a compound of Formula I, wherein R is —R¹—R³, R¹ is pyridyl, R³ is lower alkyl heterocycloalkyl, ═ is a double bond, X is N, and Y⁴ is tert-butyl.

The application provides a compound of Formula I, wherein R is —R¹—R³, R¹ is pyridyl, R³ is lower alkyl heterocycloalkyl, Y³ is F and Y⁴ is tert-butyl.

The application provides a compound of Formula I, wherein R is —R¹—R³, R¹ is pyridyl, R³ is lower alkyl heterocycloalkyl, ═ is a double bond, X is N, Y³ is F, and Y⁴ is tert-butyl.

The application provides a compound of Formula I, wherein R is —R¹—R²—R³, R¹ is pyridyl, R² is —O, and R³ is heterocycloalkyl lower alkyl, optionally substituted with one or more halo.

The application provides a compound of Formula I, wherein R is —R¹—R²—R³, R¹ is pyridyl, R² is —O, R³ is heterocycloalkyl lower alkyl, optionally substituted with one or more halo, and Y⁴ is tert-butyl.

The application provides a compound of Formula I, wherein R is —R¹—R²—R³, R¹ is pyridyl, R² is —O, R³ is heterocycloalkyl lower alkyl, optionally substituted with one or more halo, ═ is a double bond, X is N and Y⁴ is tert-butyl.

The application provides a compound of Formula I, wherein R is —R¹—R²—R³, R¹ is pyridyl, R² is —O, R³ is heterocycloalkyl lower alkyl, optionally substituted with one or more halo, Y³ is F and Y⁴ is tert-butyl.

The application provides a compound of Formula I, wherein R is —R¹—R²—R³, R¹ is pyridyl, R² is —O, R³ is heterocycloalkyl lower alkyl, optionally substituted with one or more halo, ═ L is a double bond, X is N, Y³ is F, and Y⁴ is tert-butyl.

The application provides a compound of Formula I, wherein R is —R¹—R²—R³, R¹ is pyridyl, R² is —C(═O), and R³ is dimethylamino.

The application provides a compound of Formula I, wherein R is —R¹—R²—R³, R¹ is pyridyl, R² is —C(═O), R³ is dimethylamino, and Y⁴ is tert-butyl.

The application provides a compound of Formula I, wherein R is —R¹—R²—R³, R¹ is pyridyl, R² is —C(═O), R³ is dimethylamino, ═ is a double bond, X is N and Y⁴ is tert-butyl.

The application provides a compound of Formula I, wherein R is —R¹—R²—R³, R¹ is pyridyl, R² is —C(═O), R³ is dimethylamino, Y³ is F and Y⁴ is tert-butyl.

The application provides a compound of Formula I, wherein R is —R¹—R²—R³, R¹ is pyridyl, R² is —C(═O), R³ is dimethylamino, ═ is a double bond, X is N, Y³ is F, and Y⁴ is tert-butyl.

The application provides a compound of Formula I, wherein R is —R¹—R²—R³, R¹ is pyridyl, R² is —S(═O)₂, and R³ is methyl.

The application provides a compound of Formula I, wherein R is —R¹—R²—R³, R¹ is pyridyl, R² is —S(═O)₂, and R³ is methyl, and Y⁴ is tert-butyl.

The application provides a compound of Formula I, wherein R is —R¹—R²—R³, R¹ is pyridyl, R² is —S(═O)₂, and R³ is methyl, ═ is a double bond, X is N and Y⁴ is tert-butyl.

The application provides a compound of Formula I, wherein R is —R¹—R²—R³, R¹ is pyridyl, R² is —S(═O)₂, and R³ is methyl, Y³ is F and Y⁴ is tert-butyl.

The application provides a compound of Formula I, wherein R is —R¹—R²—R³, R¹ is pyridyl, R² is —S(═O)₂, and R³ is methyl, ═ is a double bond, X is N, Y³ is F, and Y⁴ is tert-butyl.

The application provides a compound of Formula I selected from the group consisting of:

6-tert-Butyl-8-fluoro-2-{3-hydroxymethyl-4-[1-methyl-5-(1'-methyl-1',2',3',4',5',6'-hexahydro-[3,4']bipyridinyl-6-ylamino)-6-oxo-1,6-dihydro-pyridazin-3-yl]-pyridin-2-yl}-2H-phthalazin-1-one;

6-tert-Butyl-8-fluoro-2-(3-hydroxymethyl-4-{1-methyl-5-[5-((S)-1-methyl-pyrrolidin-2-yl)-pyridin-2-ylamino]-6-oxo-1,6-dihydro-pyridazin-3-yl}-pyridin-2-yl)-2H-phthalazin-1-one;

6-tert-Butyl-8-fluoro-2-(3-hydroxymethyl-4-{1-methyl-5-[5-(morpholine-4-carbonyl)-pyridin-2-ylamino]-6-oxo-1,6-dihydro-pyridazin-3-yl}-pyridin-2-yl)-2H-phthalazin-1-one;

6-tert-Butyl-8-fluoro-2-{3-hydroxymethyl-4-[5-(5-methanesulfonyl-pyridin-2-ylamino)-1-methyl-6-oxo-1,6-dihydro-pyridazin-3-yl]-pyridin-2-yl}-2H-phthalazin-1-one;

6-{6-[2-(6-tert-Butyl-8-fluoro-1-oxo-1H-phthalazin-2-yl)-3-hydroxymethyl-pyridin-4-yl]-2-methyl-3-oxo-2,3-dihydro-pyridazin-4-ylamino}-N,N-dimethyl-nicotinamide;

6-6-[2-(6-Cyclopropyl-8-fluoro-1-oxo-1H-isoquinolin-2-yl)-3-hydroxymethyl-pyridin-4-yl]-2-methyl-3-oxo-2,3-dihydro-pyridazin-4-ylamino}-N,N-dimethyl-nicotinamide;

6-tert-Butyl-2-(3-hydroxymethyl-4-{1-methyl-5-[5-(morpholine-4-carbonyl)-pyridin-2-ylamino]-6-oxo-1,6-dihydro-pyridazin-3-yl}-pyridin-2-yl)-2H-phthalazin-1-one;

2'-(6-tert-Butyl-8-fluoro-1-oxo-1H-phthalazin-2-yl)-3'-hydroxymethyl-1-methyl-5-[5-(morpholine-4-carbonyl)-pyridin-2-ylamino]-1H-[3,4']bipyridinyl-6-one;

2'-(6-tert-Butyl-8-fluoro-1-oxo-1H-phthalazin-2-yl)-3'-hydroxymethyl-5-(5-methanesulfonyl-pyridin-2-ylamino)-1-methyl-1H-[3,4']bipyridinyl-6-one;

6-[2'-(6-tert-Butyl-8-fluoro-1-oxo-1H-phthalazin-2-yl)-3'-hydroxymethyl-1-methyl-6-oxo-1,6-dihydro-[3,4']bipyridinyl-5-ylamino]-N,N-dimethyl-nicotinamide;

2'-(6-Cyclopropyl-8-fluoro-1-oxo-H-isoquinolin-2-yl)-3'-hydroxymethyl-1-methyl-5-[5-(morpholine-4-carbonyl)-pyridin-2-ylamino]-1H-[3,4']bipyridinyl-6-one;

6-tert-Butyl-2-(3-hydroxymethyl-4-{1-methyl-5-[5-((S)-1-methyl-pyrrolidin-2-yl)-pyridin-2-ylamino]-6-oxo-1,6-dihydro-pyridazin-3-yl}-pyridin-2-yl)-2H-phthalazin-1-one;

6-tert-Butyl-2-{3-hydroxymethyl-4-[1-methyl-5-(1'-methyl-1',2',3',4',5',6'-hexahydro-[3,4']bipyridinyl-6-ylamino)-6-oxo-1,6-dihydro-pyridazin-3-yl]-pyridin-2-yl}-2H-phthalazin-1-one;

6-tert-Butyl-2-{4-[5-(1'-ethyl-1',2',3',4',5',6'-hexahydro-[3,4']bipyridinyl-6-ylamino)-1-methyl-6-oxo-1,6-dihydro-pyridazin-3-yl]-3-hydroxymethyl-pyridin-2-yl}-8-fluoro-2H-phthalazin-1-one;

2-(4-{5-[5-(2-Azetidin-1-yl-1,1-dimethyl-ethoxy)-pyridin-2-ylamino]-1-methyl-6-oxo-1,6-dihydro-pyridazin-3-yl}-3-hydroxymethyl-pyridin-2-yl)-6-tert-butyl-8-fluoro-2H-phthalazin-1-one;

2-(4-{5-[5-(2-Azetidin-1-yl-1,1-dimethyl-ethoxy)-pyridin-2-ylamino]-1-methyl-6-oxo-1,6-dihydro-pyridazin-3-yl}-

3-hydroxymethyl-pyridin-2-yl)-6-tert-butyl-2H-phthalazin-1-one;

2-{4-[5-(5-Azetidin-1-ylmethyl-1-methyl-1H-pyrazol-3-ylamino)-1-methyl-6-oxo-1,6-dihydro-pyridazin-3-yl]-3-hydroxymethyl-pyridin-2-yl}-6-tert-butyl-8-fluoro-2H-phthalazin-1-one;

6-tert-Butyl-8-fluoro-2-{3-hydroxymethyl-4-[1-methyl-5-(5-methyl-4,5,6,7-tetrahydro-pyrazolo[1,5-α]pyrazin-2-ylamino)-6-oxo-1,6-dihydro-pyridazin-3-yl]-pyridin-2-yl}-2H-phthalazin-1-one;

6-tert-Butyl-2-{3-hydroxymethyl-4-[1-methyl-5-(5-methyl-4,5,6,7-tetrahydro-pyrazolo[1,5-α]pyrazin-2-ylamino)-6-oxo-1,6-dihydro-pyridazin-3-yl]-pyridin-2-yl}-2H-phthalazin-1-one;

6-Cyclopropyl-8-fluoro-2-{3-hydroxymethyl-4-[1-methyl-5-(5-methyl-4,5,6,7-tetrahydro-pyrazolo[1,5-α]pyrazin-2-ylamino)-6-oxo-1,6-dihydro-pyridazin-3-yl]-pyridin-2-yl}-2H-isoquinolin-1-one;

6-tert-Butyl-8-fluoro-2-{3-hydroxymethyl-4-[1-methyl-5-(5-oxetan-3-yl-4,5,6,7-tetrahydro-pyrazolo[1,5-α]pyrazin-2-ylamino)-6-oxo-1,6-dihydro-pyridazin-3-yl]-pyridin-2-yl}-2H-phthalazin-1-one;

6-tert-Butyl-2-{4-[5-(5-ethyl-4,5,6,7-tetrahydro-pyrazolo[1,5-α]pyrazin-2-ylamino)-1-methyl-6-oxo-1,6-dihydro-pyridazin-3-yl]-3-hydroxymethyl-pyridin-2-yl}-8-fluoro-2H-phthalazin-1-one;

6-tert-Butyl-8-fluoro-2-{3-hydroxymethyl-4-[1-methyl-5-(5-methyl-4,5,6,7-tetrahydro-pyrazolo[1,5-α]pyrazin-2-ylamino)-6-oxo-1,6-dihydro-pyridazin-3-yl]-pyridin-2-yl}-2H-isoquinolin-1-one;

6-tert-Butyl-8-fluoro-2-{3-hydroxymethyl-4-[1-methyl-5-(5-oxetan-3-yl-4,5,6,7-tetrahydro-pyrazolo[1,5-α]pyrazin-2-ylamino)-6-oxo-1,6-dihydro-pyridazin-3-yl]-pyridin-2-yl}-2H-isoquinolin-1-one;

6-tert-Butyl-2-{4-[5-(5-ethyl-4,5,6,7-tetrahydro-pyrazolo[1,5-α]pyrazin-2-ylamino)-1-methyl-6-oxo-1,6-dihydro-pyridazin-3-yl]-3-hydroxymethyl-pyridin-2-yl}-8-fluoro-2H-isoquinolin-1-one;

6-tert-Butyl-2-{4-[5-(5-cyclopropylmethyl-4,5,6,7-tetrahydro-pyrazolo[1,5-α]pyrazin-2-ylamino)-1-methyl-6-oxo-1,6-dihydro-pyridazin-3-yl]-3-hydroxymethyl-pyridin-2-yl}-8-fluoro-2H-phthalazin-1-one;

6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-8-fluoro-2H-isoquinolin-1-one;

4-(6-tert-Butyl-8-fluoro-1-oxo-1H-phthalazin-2-yl)-3-hydroxymethyl-1'-methyl-5'-[5-(morpholine-4-carbonyl)-pyridin-2-ylamino]-1'H-[2,3']bipyridinyl-6'-one, 4-(6-tert-Butyl-8-fluoro-1-oxo-1H-phthalazin-2-yl)-3-hydroxymethyl-5'-(5-methanesulfonyl-pyridin-2-ylamino)-1'-methyl-1'H-[2,3']bipyridinyl-6'-one;

6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-8-fluoro-2H-phthalazin-1-one;

2-(8-Fluoro-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-1-oxo-1,2-dihydro-isoquinolin-6-yl)-2-methyl-propionitrile;

2-{2-[4-(5-{5-[2-(3,3-Difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-8-fluoro-1-oxo-1,2-dihydro-isoquinolin-6-yl}-2-methyl-propionitrile;

6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-2H-phthalazin-1-one; and 6-tert-Butyl-8-fluoro-2-{3-hydroxymethyl-4-[1-methyl-5-(5-methyl-5-oxy-4,5,6,7-tetrahydro-pyrazolo[1,5-α]pyrazin-2-ylamino)-6-oxo-1,6-dihydro-pyridazin-3-yl]-pyridin-2-yl}-2H-phthalazin-1-one.

The application provides a method for treating an inflammatory and/or autoimmune condition comprising administering to a patient in need thereof a therapeutically effective amount of the compound of Formula I.

The application provides a method for treating rheumatoid arthritis comprising administering to a patient in need thereof a therapeutically effective amount of the compound of Formula I.

The application provides a method for treating asthma comprising administering to a patient in need thereof a therapeutically effective amount of the compound of Formula I.

The application provides a pharmaceutical composition comprising the compound of Formula I.

The application provides a pharmaceutical composition comprising the compound of Formula I, admixed with at least one pharmaceutically acceptable carrier, excipient or diluent.

The application provides a use of the compound of formula I in the manufacture of a medicament for the treatment of an inflammatory disorder.

The application provides a use of the compound of formula I in the manufacture of a medicament for the treatment of an autoimmune disorder.

The application provides a use of the compound of formula I in the manufacture of a medicament for the treatment of rheumatoid arthritis.

The application provides a use of the compound of formula I in the manufacture of a medicament for the treatment of asthma.

The application provides a compound, method, or composition as described herein.

The application provides a compound, method, or composition as described herein.

Btk Inhibitor Compounds

Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

TABLE I depicts examples of pyridazinone compounds according to generic Formula I:

TABLE I

| Compound | Nomenclature | Structure |
|---|---|---|
| I-1 | 6-tert-Butyl-8-fluoro-2-{3-hydroxymethyl-4-[1-methyl-5-(1'-methyl-1',2',3',4',5',6'-hexahydro-[3,4']bipyridinyl-6-ylamino)-6-oxo-1,6-dihydro-pyridazin-3-yl]-pyridin-2-yl}-2H-phthalazin-1-one | 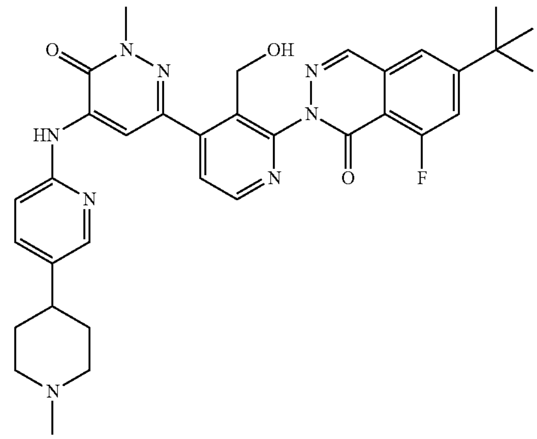 [SMILES: CN1CCC(c2ccc(Nc3cc(-c4ccnc(-n5ncc6cc(C(C)(C)C)cc(F)c6c5=O)c4CO)nn(C)c3=O)nc2)CC1] |
| I-2 | 6-tert-Butyl-8-fluoro-2-(3-hydroxymethyl-4-{1-methyl-5-[5-((S)-1-methyl-pyrrolidin-2-yl)-pyridin-2-ylamino]-6-oxo-1,6-dihydro-pyridazin-3-yl}-pyridin-2-yl)-2H-phthalazin-1-one | 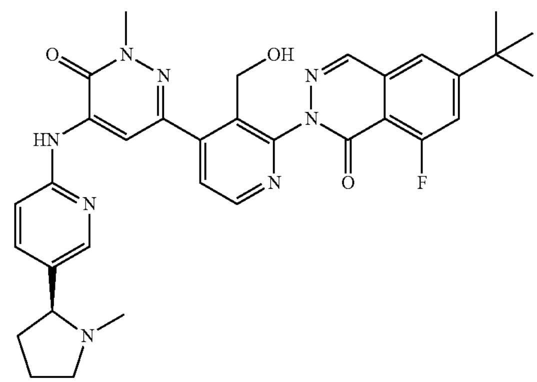 [SMILES: CN1CCC[C@H]1c1ccc(Nc2cc(-c3ccnc(-n4ncc5cc(C(C)(C)C)cc(F)c5c4=O)c3CO)nn(C)c2=O)nc1] |
| I-3 | 6-tert-Butyl-8-fluoro-2-(3-hydroxymethyl-4-{1-methyl-5-[5-(morpholine-4-carbonyl)-pyridin-2-ylamino]-6-oxo-1,6-dihydro-pyridazin-3-yl}-pyridin-2-yl)-2H-phthalazin-1-one | 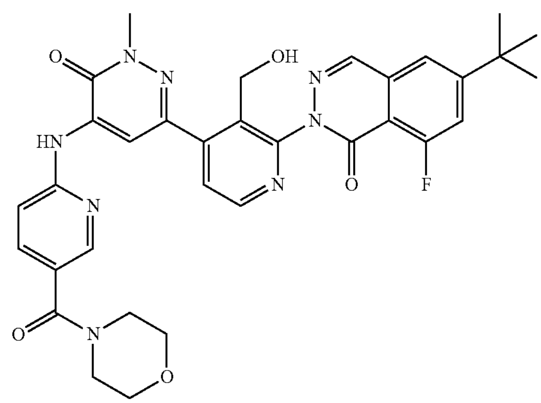 [SMILES: Cn1nc(-c2ccnc(-n3ncc4cc(C(C)(C)C)cc(F)c4c3=O)c2CO)cc(Nc2ccc(C(=O)N3CCOCC3)cn2)c1=O] |
| I-4 | 6-tert-Butyl-8-fluoro-2-{3-hydroxymethyl-4-[5-(5-methanesulfonyl-pyridin-2-ylamino)-1-methyl-6-oxo-1,6-dihydro-pyridazin-3-yl]-pyridin-2-yl}-2H-phthalazin-1-one | 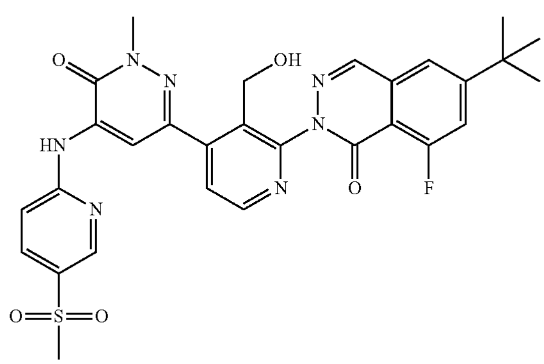 |

TABLE I-continued

| Compound | Nomenclature | Structure |
|---|---|---|
| I-5 | 6-{6-[2-(6-tert-Butyl-8-fluoro-1-oxo-1H-phthalazin-2-yl)-3-hydroxymethyl-pyridin-4-yl]-2-methyl-3-oxo-2,3-dihydro-pyridazin-4-ylamino}-N,N-dimethyl-nicotinamide | 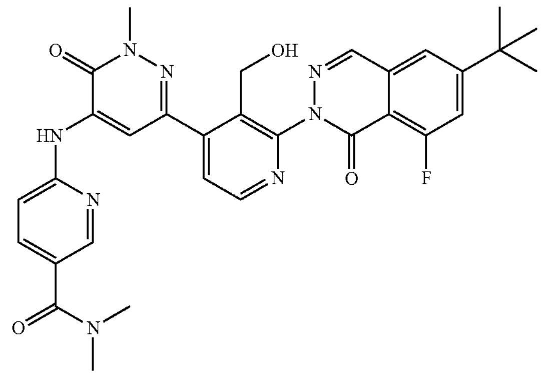 [SMILES: CN(C)C(=O)c1ccc(Nc2cc(-c3ccnc(-n4ncc5cc(C(C)(C)C)cc(F)c5c4=O)c3CO)nn(C)c2=O)nc1] |
| I-6 | 6-{6-[2-(6-Cyclopropyl-8-fluoro-1-oxo-1H-isoquinolin-2-yl)-3-hydroxymethyl-pyridin-4-yl]-2-methyl-3-oxo-2,3-dihydro-pyridazin-4-ylamino}-N,N-dimethyl-nicotinamide | 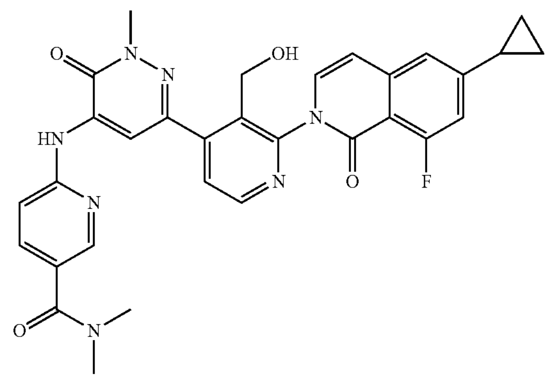 [SMILES: CN(C)C(=O)c1ccc(Nc2cc(-c3ccnc(-n4ccc5cc(C6CC6)cc(F)c5c4=O)c3CO)nn(C)c2=O)nc1] |
| I-7 | 6-tert-Butyl-2-(3-hydroxymethyl-4-{1-methyl-5-[5-(morpholine-4-carbonyl)-pyridin-2-ylamino]-6-oxo-1,6-dihydro-pyridazin-3-yl}-pyridin-2-yl)-2H-phthalazin-1-one | 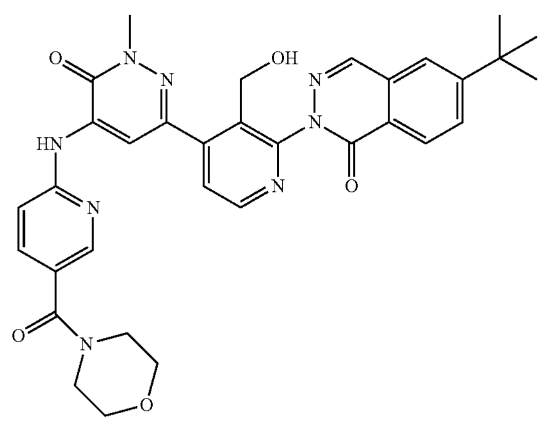 [SMILES: Cn1nc(-c2ccnc(-n3ncc4cc(C(C)(C)C)ccc4c3=O)c2CO)cc(Nc2ccc(C(=O)N3CCOCC3)cn2)c1=O] |
| I-8 | 2'-(6-tert-Butyl-8-fluoro-1-oxo-1H-phthalazin-2-yl)-3'-hydroxymethyl-1-methyl-5-[5-(morpholine-4-carbonyl)-pyridin-2-ylamino]-1H-[3,4']bipyridinyl-6-one | 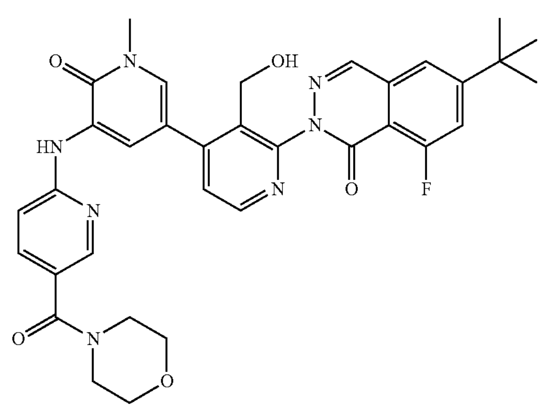 [SMILES: Cn1cc(-c2ccnc(-n3ncc4cc(C(C)(C)C)cc(F)c4c3=O)c2CO)cc(Nc2ccc(C(=O)N3CCOCC3)cn2)c1=O] |

TABLE I-continued

| Compound | Nomenclature | Structure |
|---|---|---|
| I-9 | 2'-(6-tert-Butyl-8-fluoro-1-oxo-1H-phthalazin-2-yl)-3'-hydroxymethyl-5-(5-methanesulfonyl-pyridin-2-ylamino)-1-methyl-1H-[3,4']bipyridinyl-6-one | 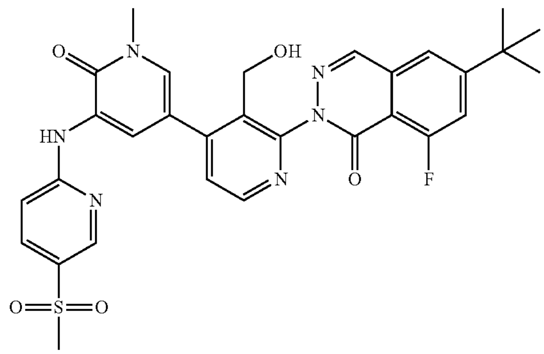 |
| I-10 | 6-[2'-(6-tert-Butyl-8-fluoro-1-oxo-1H-phthalazin-2-yl)-3'-hydroxymethyl-1-methyl-6-oxo-1,6-dihydro-[3,4']bipyridinyl-5-ylamino]-N,N-dimethyl-nicotinamide | 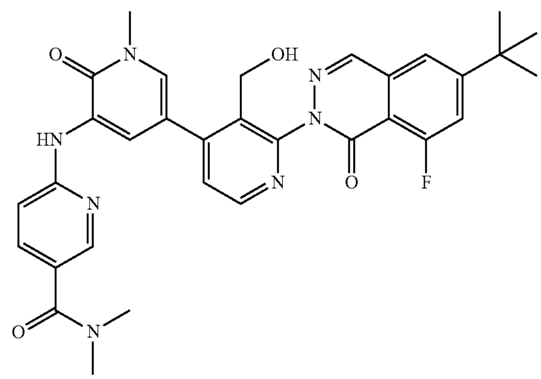 [SMILES: CN(C)C(=O)c1ccc(Nc2cc(-c3ccnc(-n4ncc5cc(C(C)(C)C)cc(F)c5c4=O)c3CO)cn(C)c2=O)nc1] |
| I-11 | 2'-(6-Cyclopropyl-8-fluoro-1-oxo-1H-isoquinolin-2-yl)-3'-hydroxymethyl-1-methyl-5-[5-(morpholine-4-carbonyl)-pyridin-2-ylamino]-1H-[3,4']bipyridinyl-6-one | 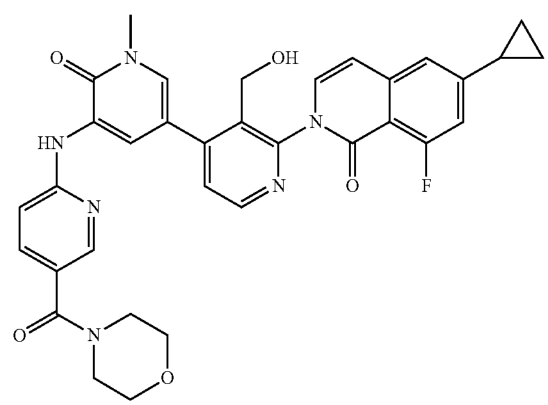 [SMILES: Cn1cc(-c2ccnc(-n3ccc4cc(C5CC5)cc(F)c4c3=O)c2CO)cc(Nc2ccc(C(=O)N3CCOCC3)cn2)c1=O] |
| I-12 | 6-tert-Butyl-2-(3-hydroxymethyl-4-{1-methyl-5-[5-((S)-1-methyl-pyrrolidin-2-yl)-pyridin-2-ylamino]-6-oxo-1,6-dihydro-pyridazin-3-yl}-pyridin-2-yl)-2H-phthalazin-1-one | 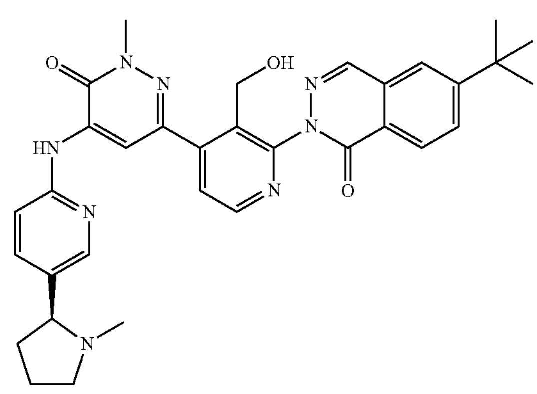 [SMILES: CN1CCC[C@H]1c1ccc(Nc2cc(-c3ccnc(-n4ncc5cc(C(C)(C)C)ccc5c4=O)c3CO)nn(C)c2=O)nc1] |

TABLE I-continued

| Compound | Nomenclature | Structure |
|---|---|---|
| I-13 | 6-tert-Butyl-2-{3-hydroxymethyl-4-[1-methyl-5-(1'-methyl-1',2',3',4',5',6'-hexahydro-[3,4']bipyridinyl-6-ylamino)-6-oxo-1,6-dihydro-pyridazin-3-yl]-pyridin-2-yl}-2H-phthalazin-1-one | 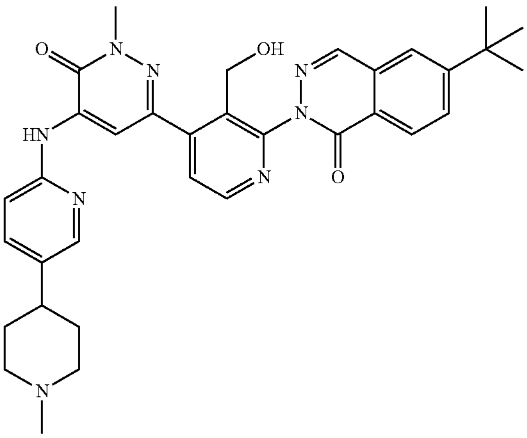 [SMILES: CN1CCC(c2ccc(Nc3cc(-c4ccnc(-n5ncc6cc(C(C)(C)C)ccc6c5=O)c4CO)nn(C)c3=O)nc2)CC1] |
| I-14 | 6-tert-Butyl-2-{4-[5-(1'-ethyl-1',2',3',4',5',6'-hexahydro-[3,4']bipyridinyl-6-ylamino)-1-methyl-6-oxo-1,6-dihydro-pyridazin-3-yl]-3-hydroxymethyl-pyridin-2-yl}-8-fluoro-2H-phthalazin-1-one | 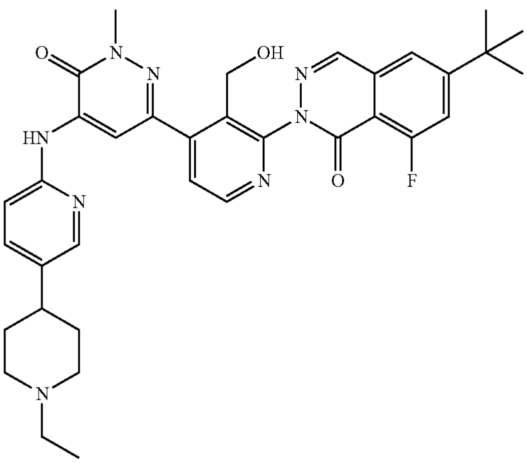 [SMILES: CCN1CCC(c2ccc(Nc3cc(-c4ccnc(-n5ncc6cc(C(C)(C)C)cc(F)c6c5=O)c4CO)nn(C)c3=O)nc2)CC1] |
| I-15 | 2-(4-{5-[5-(2-Azetidin-1-yl-1,1-dimethyl-ethoxy)-pyridin-2-ylamino]-1-methyl-6-oxo-1,6-dihydro-pyridazin-3-yl}-3-hydroxymethyl-pyridin-2-yl)-6-tert-butyl-8-fluoro-2H-phthalazin-1-one | 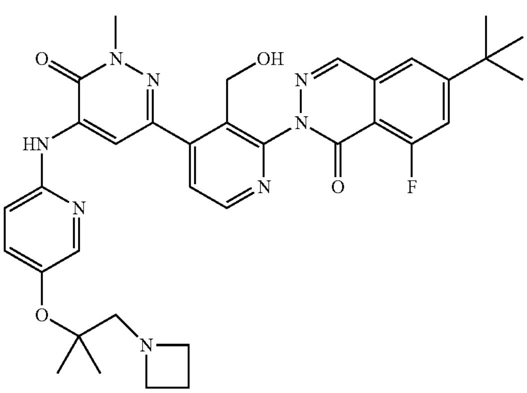 [SMILES: Cn1nc(-c2ccnc(-n3ncc4cc(C(C)(C)C)cc(F)c4c3=O)c2CO)cc(Nc2ccc(OC(C)(C)CN3CCC3)cn2)c1=O] |

TABLE I-continued

| Compound | Nomenclature | Structure |
|---|---|---|
| I-16 | 2-(4-{5-[5-(2-Azetidin-1-yl-1,1-dimethyl-ethoxy)-pyridin-2-ylamino]-1-methyl-6-oxo-1,6-dihydro-pyridazin-3-yl}-3-hydroxymethyl-pyridin-2-yl)-6-tert-butyl-2H-phthalazin-1-one | 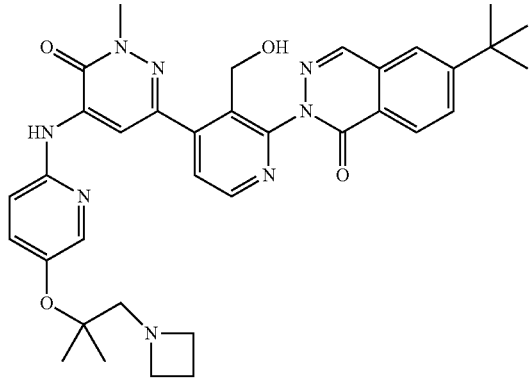 [SMILES: Cn1nc(-c2ccnc(-n3ncc4cc(C(C)(C)C)ccc4c3=O)c2CO)cc(Nc2ccc(OC(C)(C)CN3CCC3)cn2)c1=O] |
| I-17 | 2-{4-[5-(5-Azetidin-1-ylmethyl-1-methyl-1H-pyrazol-3-ylamino)-1-methyl-6-oxo-1,6-dihydro-pyridazin-3-yl]-3-hydroxymethyl-pyridin-2-yl}-6-tert-butyl-8-fluoro-2H-phthalazin-1-one | 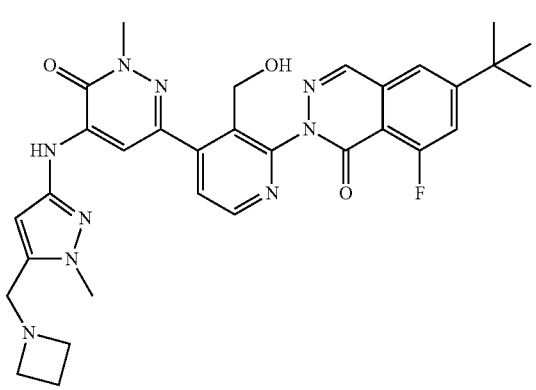 [SMILES: Cn1nc(Nc2cc(-c3ccnc(-n4ncc5cc(C(C)(C)C)cc(F)c5c4=O)c3CO)nn(C)c2=O)cc1CN1CCC1] |
| I-18 | 6-tert-Butyl-8-fluoro-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-2H-phthalazin-1-one | 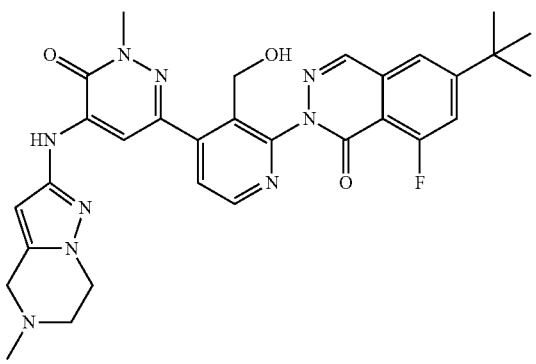 [SMILES: CN1CCn2nc(Nc3cc(-c4ccnc(-n5ncc6cc(C(C)(C)C)cc(F)c6c5=O)c4CO)nn(C)c3=O)cc2C1] |
| I-19 | 6-tert-Butyl-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-2H-phthalazin-1-one | 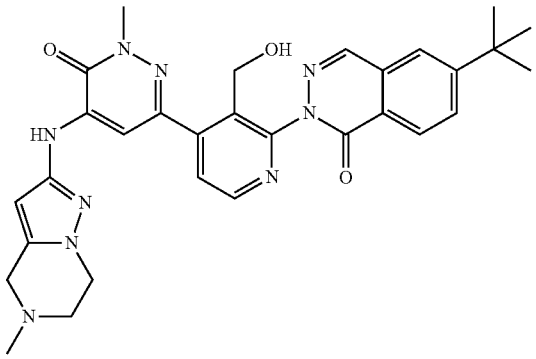 [SMILES: CN1CCn2nc(Nc3cc(-c4ccnc(-n5ncc6cc(C(C)(C)C)ccc6c5=O)c4CO)nn(C)c3=O)cc2C1] |

TABLE I-continued

| Compound | Nomenclature | Structure |
|---|---|---|
| I-20 | 6-Cyclopropyl-8-fluoro-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-2H-isoquinolin-1-one | 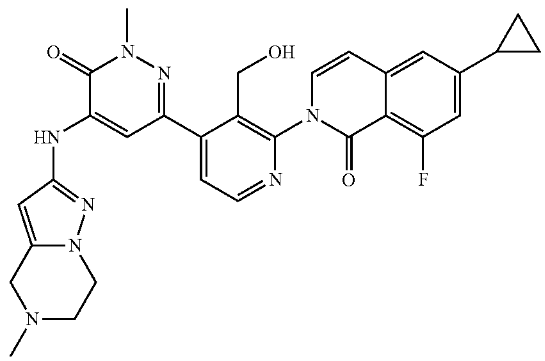 [SMILES: CN1CCn2nc(Nc3cc(-c4ccnc(-n5ccc6cc(C7CC7)cc(F)c6c5=O)c4CO)nn(C)c3=O)cc2C1] |
| I-21 | 6-tert-Butyl-8-fluoro-2-{3-hydroxymethyl-4-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-pyridin-2-yl}-2H-phthalazin-1-one | 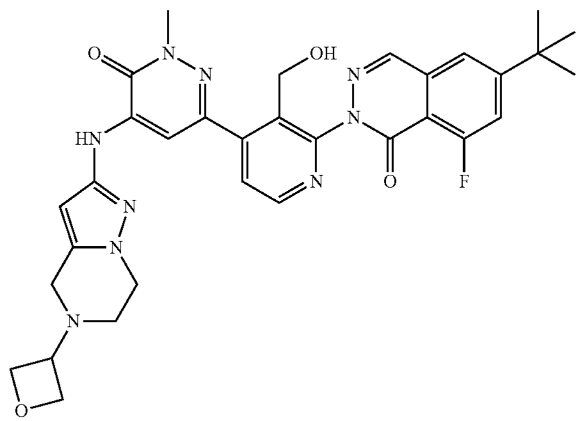 [SMILES: Cn1nc(-c2ccnc(-n3ncc4cc(C(C)(C)C)cc(F)c4c3=O)c2CO)cc(Nc2cc3n(n2)CCN(C2COC2)C3)c1=O] |
| I-22 | 6-tert-Butyl-2-{4-[5-(5-ethyl-4,5,6,7-tetrahydro-pyrazolo[1,5-a]pyrazin-2-ylamino)-1-methyl-6-oxo-1,6-dihydro-pyridazin-3-yl]-3-hydroxymethyl-pyridin-2-yl}-8-fluoro-2H-phthalazin-1-one | 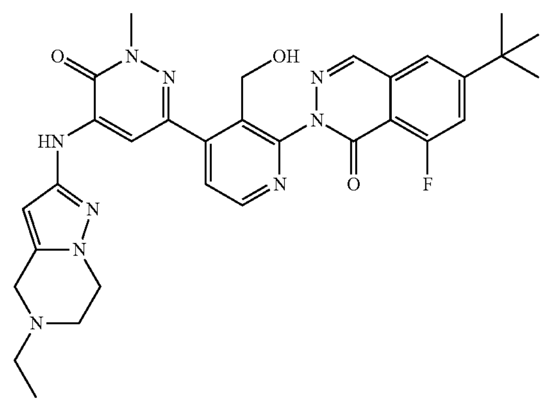 [SMILES: CCN1CCn2nc(Nc3cc(-c4ccnc(-n5ncc6cc(C(C)(C)C)cc(F)c6c5=O)c4CO)nn(C)c3=O)cc2C1] |
| I-23 | 6-tert-Butyl-8-fluoro-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-2H-isoquinolin-1-one | 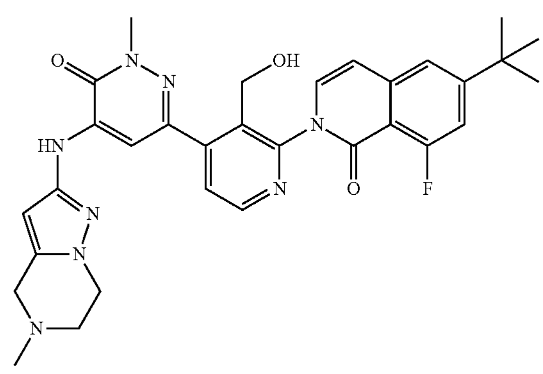 [SMILES: CN1CCn2nc(Nc3cc(-c4ccnc(-n5ccc6cc(C(C)(C)C)cc(F)c6c5=O)c4CO)nn(C)c3=O)cc2C1] |

TABLE I-continued

| Compound | Nomenclature | Structure |
|---|---|---|
| I-24 | 6-tert-Butyl-8-fluoro-2-{3-hydroxymethyl-4-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-pyridin-2-yl}-2H-isoquinolin-1-one | 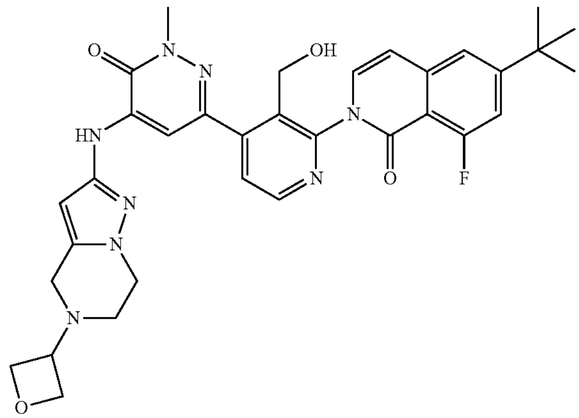 [SMILES: Cn1nc(-c2ccnc(-n3ccc4cc(C(C)(C)C)cc(F)c4c3=O)c2CO)cc(Nc2cc3n(n2)CCN(C2COC2)C3)c1=O] |
| I-25 | 6-tert-Butyl-2-{4-[5-(5-ethyl-4,5,6,7-tetrahydro-pyrazolo[1,5-a]pyrazin-2-ylamino)-1-methyl-6-oxo-1,6-dihydro-pyridazin-3-yl]-3-hydroxymethyl-pyridin-2-yl}-8-fluoro-2H-isoquinolin-1-one | 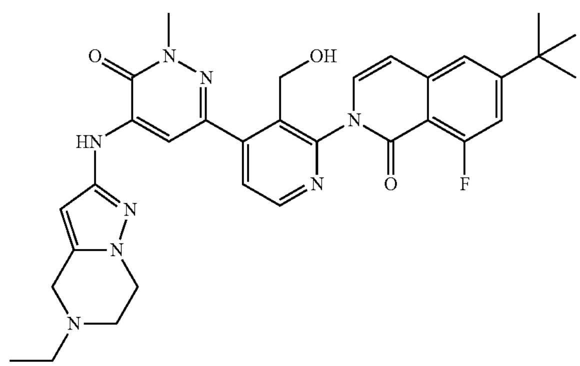 [SMILES: CCN1CCn2nc(Nc3cc(-c4ccnc(-n5ccc6cc(C(C)(C)C)cc(F)c6c5=O)c4CO)nn(C)c3=O)cc2C1] |
| I-26 | 6-tert-Butyl-2-{4-[5-(5-cyclopropylmethyl-4,5,6,7-tetrahydro-pyrazolo[1,5-a]pyrazin-2-ylamino)-1-methyl-6-oxo-1,6-dihydro-pyridazin-3-yl]-3-hydroxymethyl-pyridin-2-yl}-8-fluoro-2H-phthalazin-1-one | 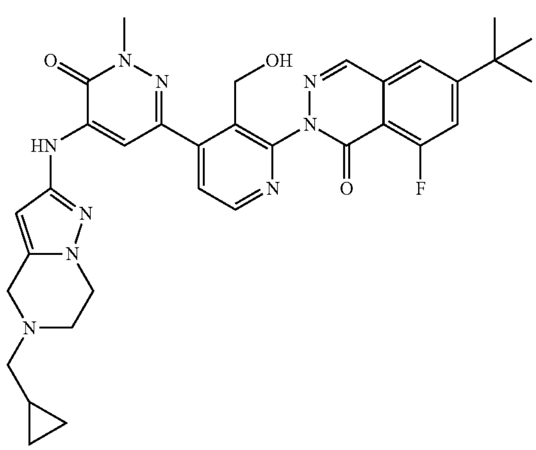 [SMILES: Cn1nc(-c2ccnc(-n3ncc4cc(C(C)(C)C)cc(F)c4c3=O)c2CO)cc(Nc2cc3n(n2)CCN(CC2CC2)C3)c1=O] |

TABLE I-continued

| Compound | Nomenclature |
|---|---|
| I-27 | 6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-8-fluoro-2H-isoquinolin-1-one |
| I-28 | 4-(6-tert-Butyl-8-fluoro-1-oxo-1H-phthalazin-2-yl)-3-hydroxymethyl-1'-methyl-5'-[5-(morpholine-4-carbonyl)-pyridin-2-ylamino]-1'H-[2,3']bipyridinyl-6'-one |
| I-29 | 4-(6-tert-Butyl-8-fluoro-1-oxo-1H-phthalazin-2-yl)-3-hydroxymethyl-5'-(5-methanesulfonyl-pyridin-2-ylamino)-1'-methyl-1'H-[2,3']bipyridinyl-6'-one |
| I-30 | 6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-8-fluoro-2H-phthalazin-1-one |

TABLE I-continued

| Compound | Nomenclature | Structure |
|---|---|---|
| I-31 | 2-(8-Fluoro-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-1-oxo-1,2-dihydro-isoquinolin-6-yl)-2-methyl-propionitrile | 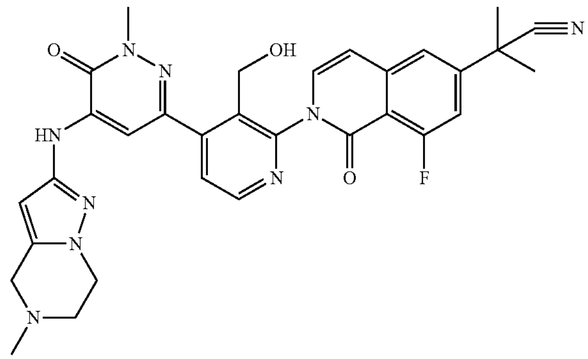 [SMILES: CN1CCn2nc(Nc3cc(-c4ccnc(-n5ccc6cc(C(C)(C)C#N)cc(F)c6c5=O)c4CO)nn(C)c3=O)cc2C1] |
| I-32 | 2-{2-[4-(5-{5-[2-(3,3-Difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-8-fluoro-1-oxo-1,2-dihydro-isoquinolin-6-yl}-2-methyl-propionitrile | 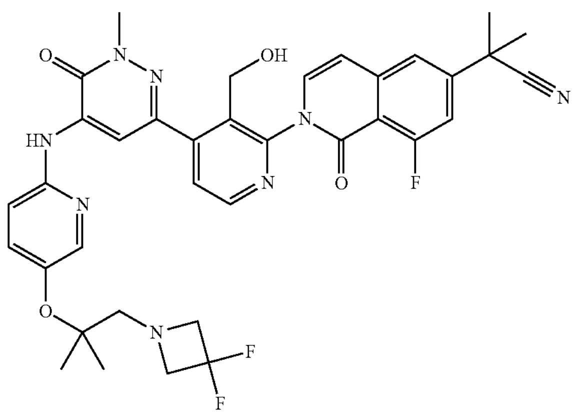 [SMILES: Cn1nc(-c2ccnc(-n3ccc4cc(C(C)(C)C#N)cc(F)c4c3=O)c2CO)cc(Nc2ccc(OC(C)(C)CN3CC(F)(F)C3)cn2)c1=O] |
| I-33 | 6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-2H-phthalazin-1-one | 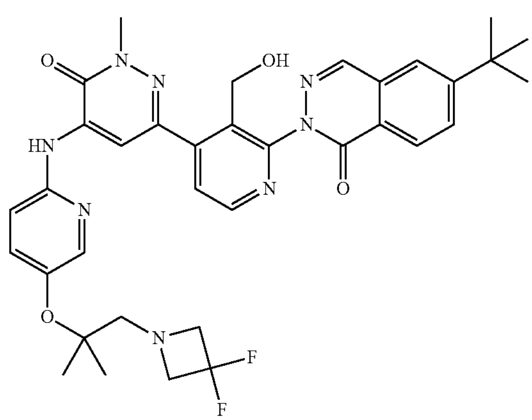 [SMILES: Cn1nc(-c2ccnc(-n3ncc4cc(C(C)(C)C)ccc4c3=O)c2CO)cc(Nc2ccc(OC(C)(C)CN3CC(F)(F)C3)cn2)c1=O] |

TABLE I-continued

| Compound | Nomenclature | Structure |
|---|---|---|
| I-34 | 6-tert-Butyl-8-fluoro-2-{3-hydroxymethyl-4-[1-methyl-5-(5-methyl-5-oxy-4,5,6,7-tetrahydro-pyrazolo[1,5-a]pyrazin-2-ylamino)-6-oxo-1,6-dihydro-pyridazin-3-yl]-pyridin-2-yl}-2H-phthalazin-1-one | 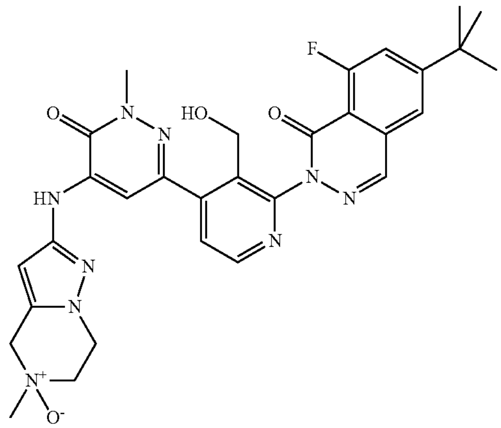 [SMILES: Cn1nc(-c2ccnc(-n3ncc4cc(C(C)(C)C)cc(F)c4c3=O)c2CO)cc(Nc2cc3n(n2)CC[N+](C)([O-])C3)c1=O] |

Synthesis
General Synthetic Schemes

In the general schemes below, $Y^3$ can be H or F, $Y^4$ can be $Y^{4a}$, $Y^{4b}$, $Y^{4c}$, or $Y^{4d}$; $Y^{4a}$ can be H or halogen; $Y^{4b}$ can be lower alkyl, optionally substituted with one or more substituents selected from the group consisting of lower haloalkyl, halogen, hydroxy, amino, cyano, and lower alkoxy; $Y^{4c}$ can be lower cycloalkyl, optionally substituted with one or more substituents selected from the group consisting of lower alkyl, lower haloalkyl, halogen, hydroxy, amino, cyano, and lower alkoxy; and $Y^{4d}$ can be amino, optionally substituted with one or more lower alkyl, alkoxy lower alkyl, or hydroxy lower alkyl. Wherein X can be CH or N, R can be H, —$R^1$, —$R^1$—$R^2$—$R^3$, —$R^1$—$R^3$, or —$R^2$—$R^3$; $R^1$ can be aryl, heteroaryl, bicyclic heteroaryl, cycloalkyl, or heterocycloalkyl, each of which can be optionally substituted with one or more lower alkyl, hydroxy, hydroxy lower alkyl, lower alkoxy, halo, nitro, amino, amido, cyano, oxo, or lower haloalkyl; $R^2$ can be —C(=O), —C(=O)O, —C(=O)NR$^{2'}$, —NHC(=O)O, —C($R^{2'}$)$_2$, —O, —S, —C(=NH)NR$^{2'}$, or —S(=O)$_2$; each $R^{2'}$ can be independently H or lower alkyl; $R^3$ can be H or $R^4$; $R^4$ can be lower alkyl, lower haloalkyl, lower alkoxy, amino, lower alkyl amino, cycloalkyl amino, lower dialkyl amino, aryl, arylalkyl, alkylaryl, heteroaryl, alkyl heteroaryl, heteroaryl alkyl, cycloalkyl, alkyl cycloalkyl, cycloalkyl alkyl, heterocycloalkyl, alkyl heterocycloalkyl, heterocycloalkyl alkyl, bicyclic cycloalkyl, bicyclic heterocycloalkyl, spirocycloalkyl, spiroheterocycloalkyl, or bicyclic spiroheterocycloalkyl each of which can be optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxylamino, carboxy, carbamoyl, carbamate, halo lower alkoxy, heterocycloalkyl, or halo lower alkyl, wherein two lower alkyl groups may together form a ring; R' can be H, lower alkyl, cycloalkyl, cycloalkyl lower alkyl, or heterocycloalkyl or lower haloalkyl; $R^{3'}$ can be H, lower alkyl, or come together to form spiro cycloalkyl; and $R^{4'}$ can be H, lower alkyl, or come together to form heterocycloalkyl, optionally substituted with halogen.

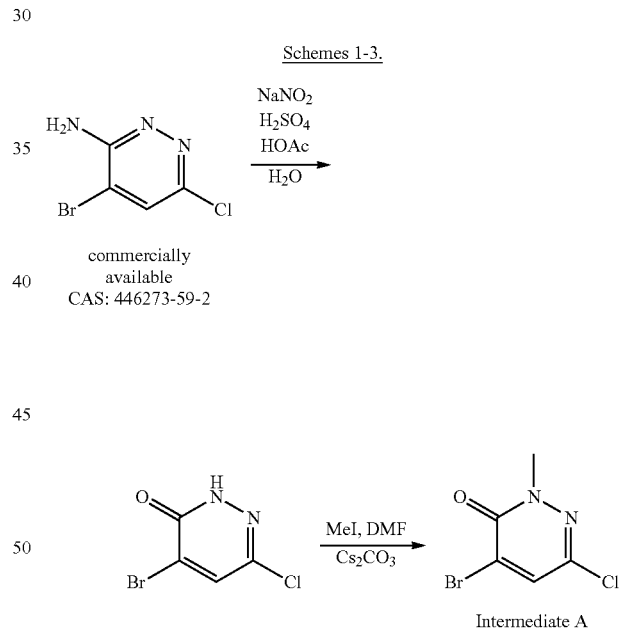

Schemes 1-3.

Scheme 2.

35
-continued
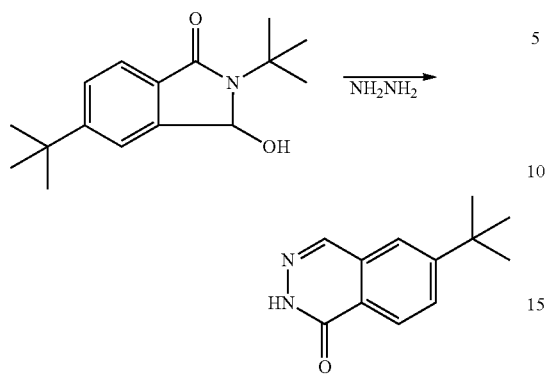
Scheme 3a-3b.
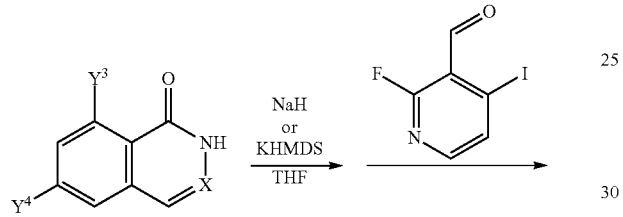
36
-continued
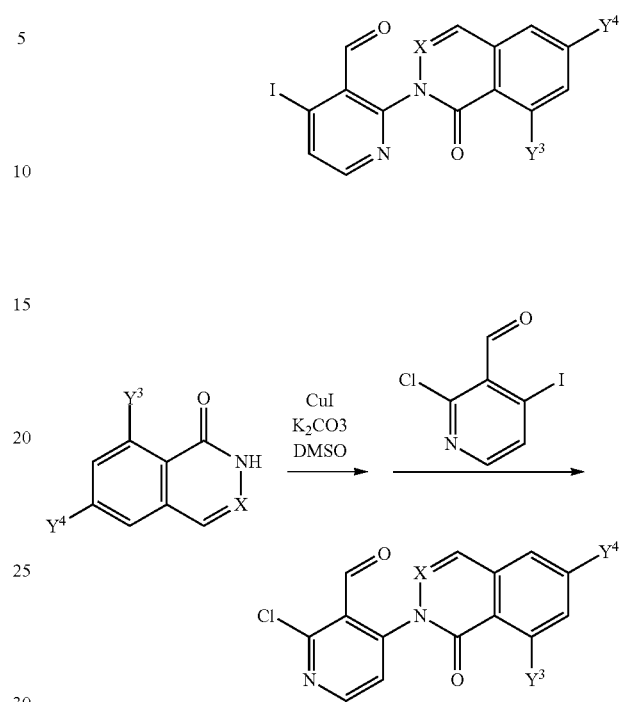
Scheme 4.
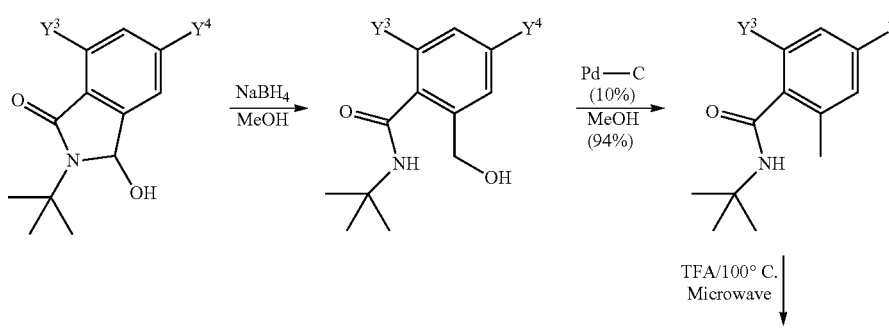
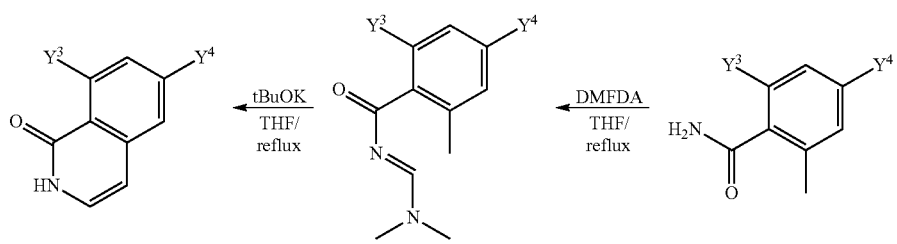

Scheme 5.
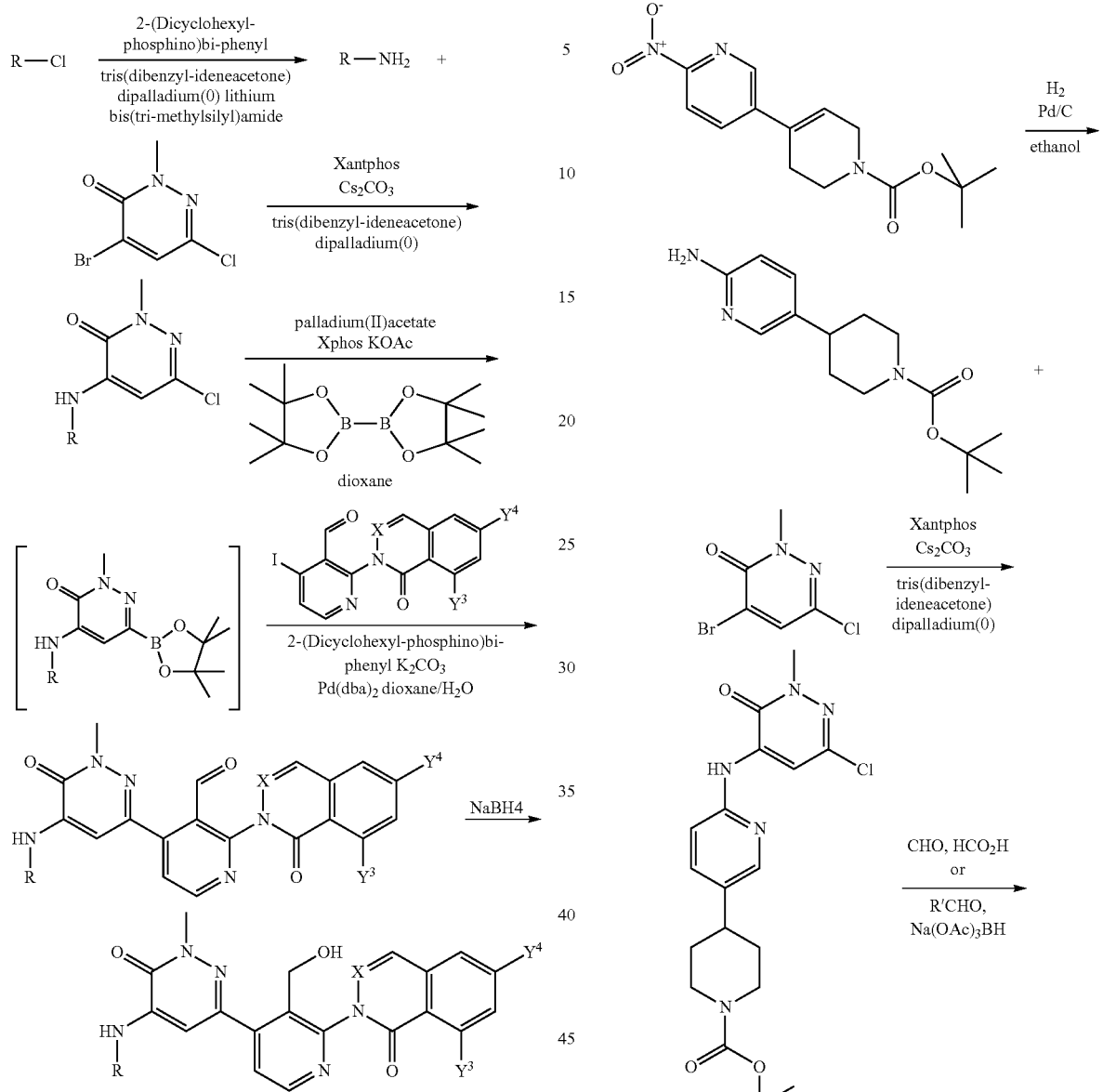
Scheme 6.
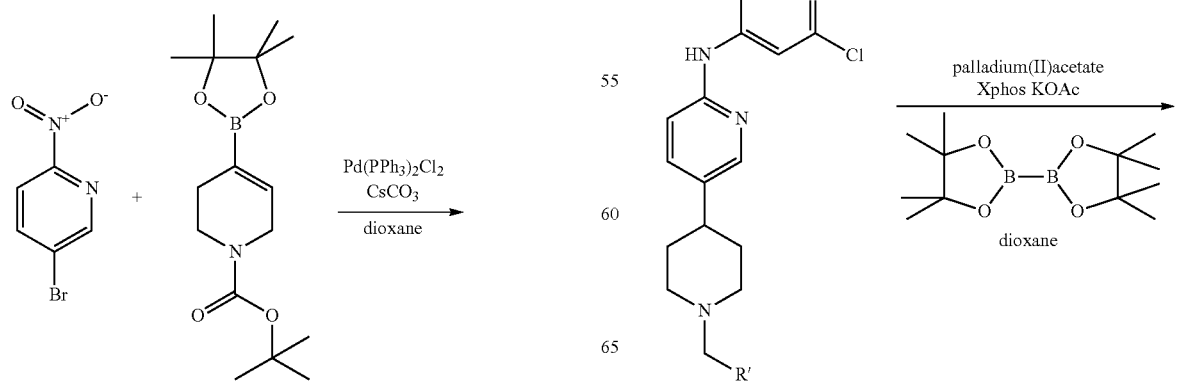

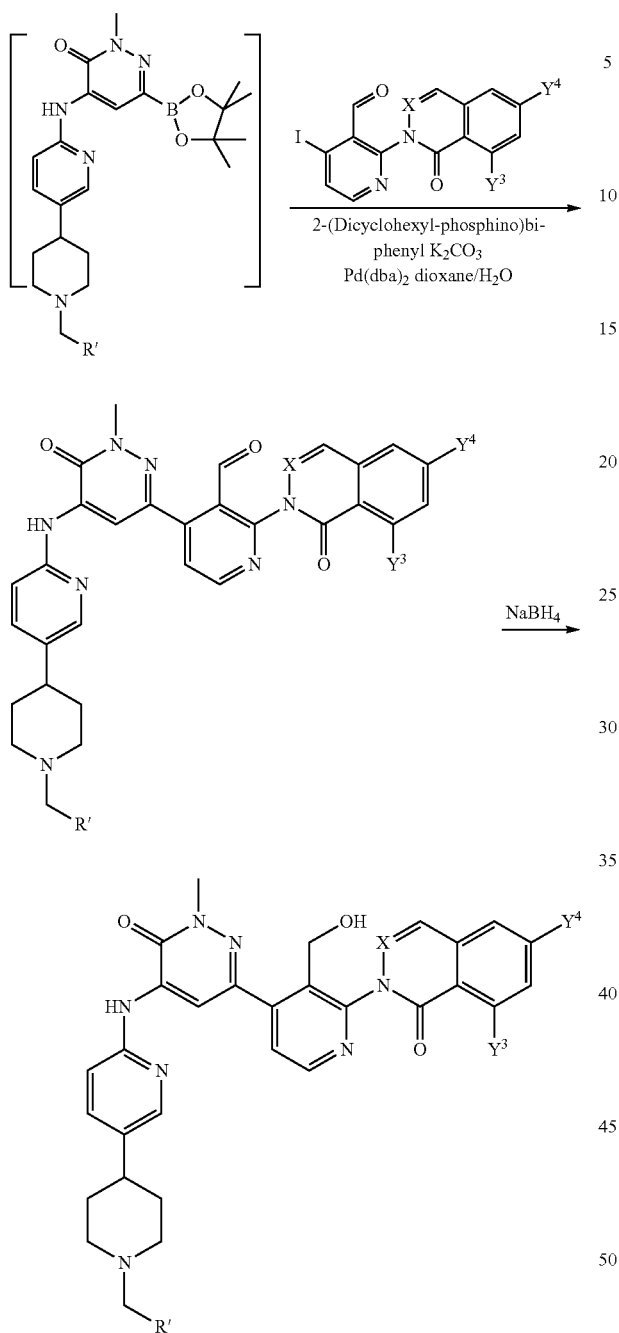
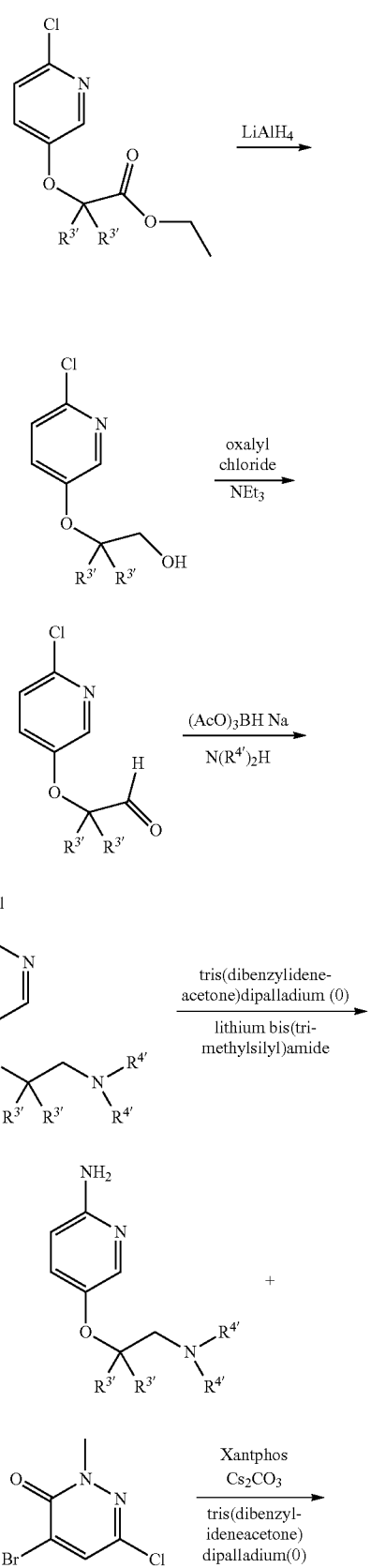
Scheme 7.
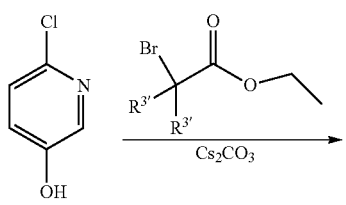
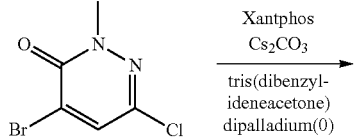

41
-continued
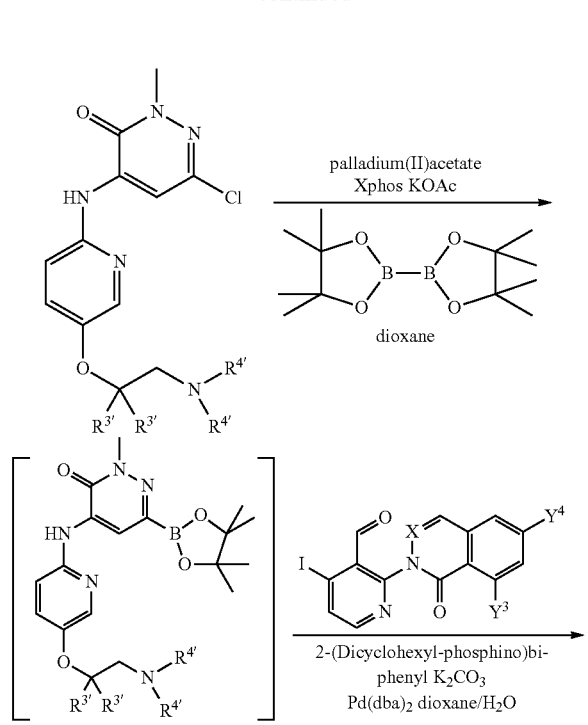
42
-continued
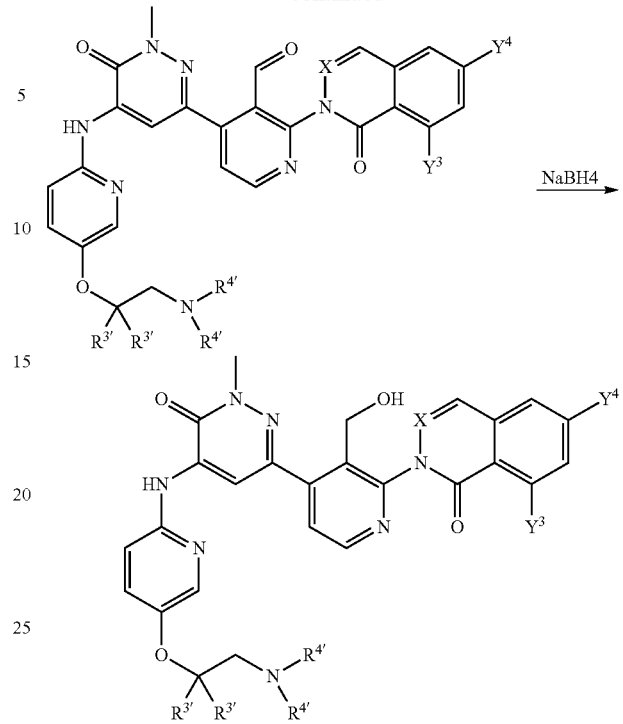
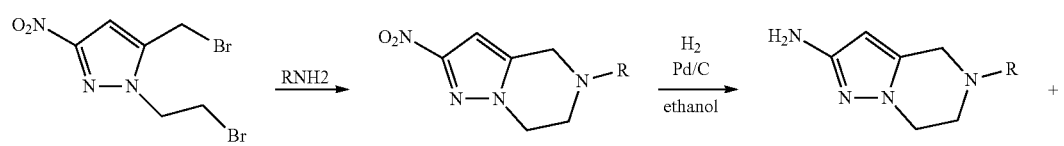
Scheme 8.
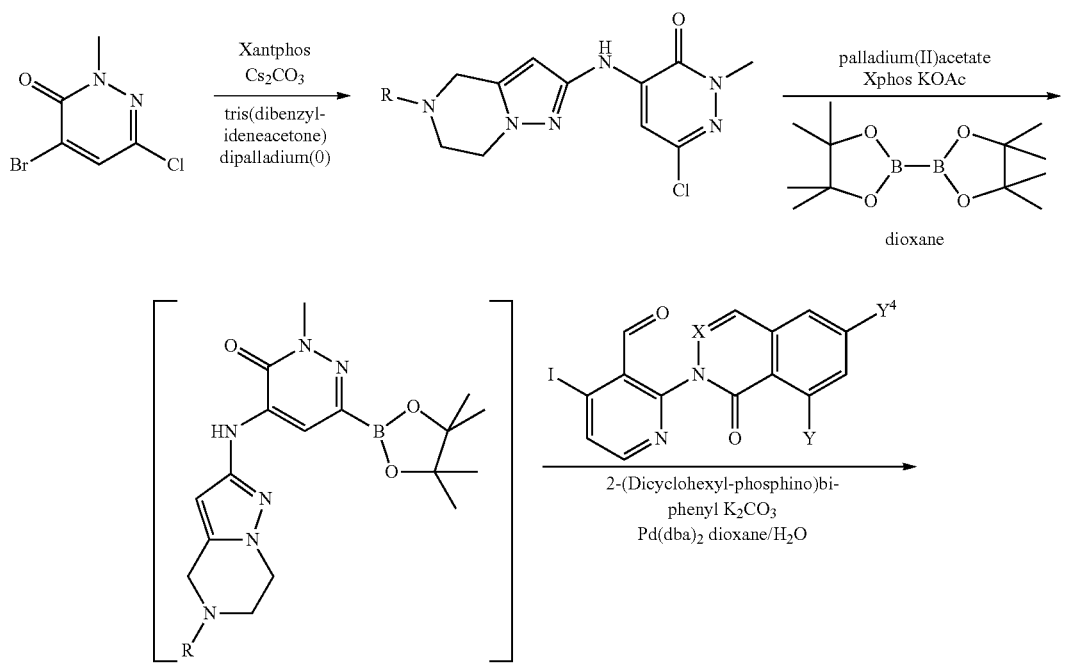

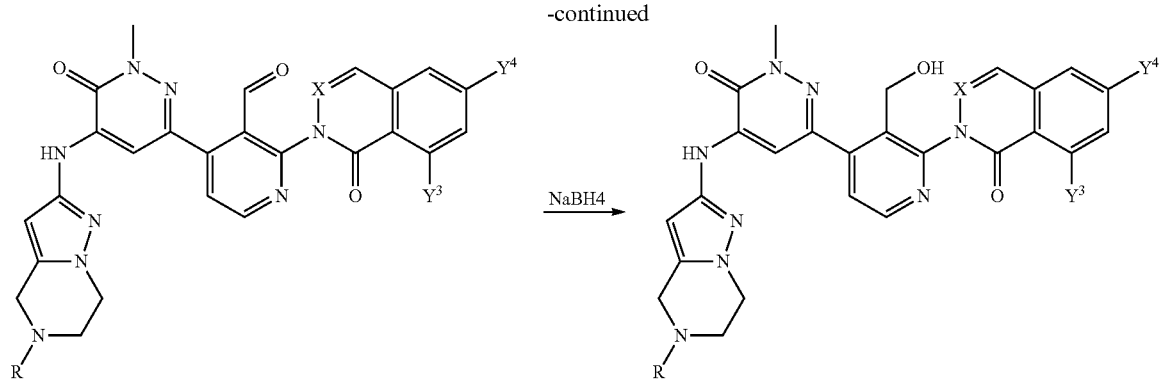
Wherein R can be H, lower alkyl, cycloalkyl, cycloalkyl lower alkyl, or heterocycloalkyl or lower haloalkyl.
Scheme 9.
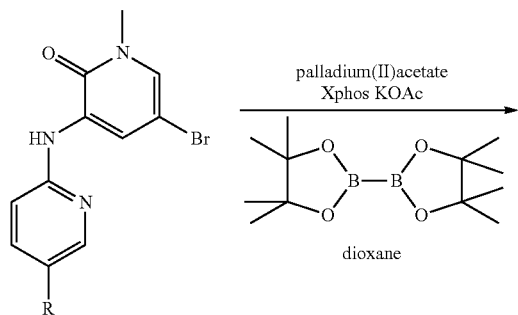
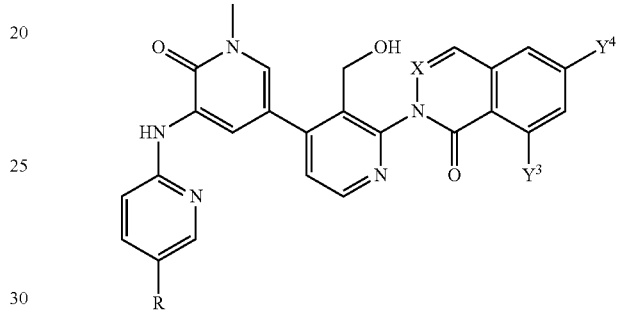
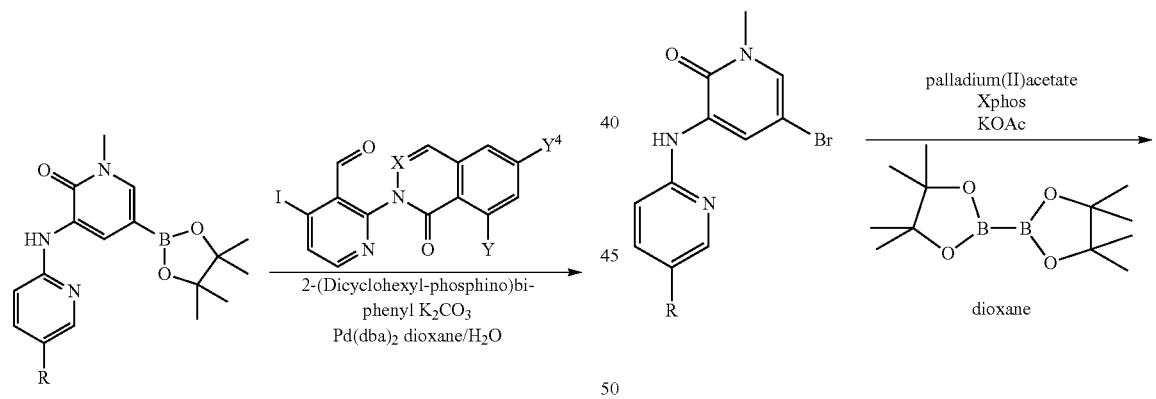
Scheme 10.
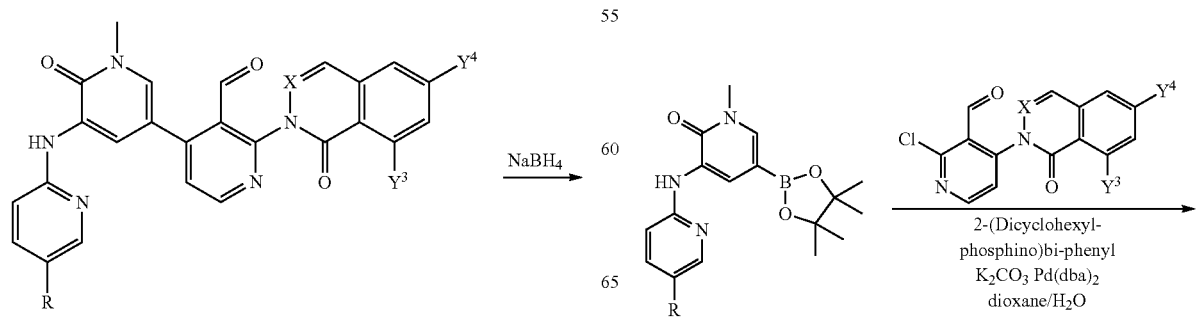

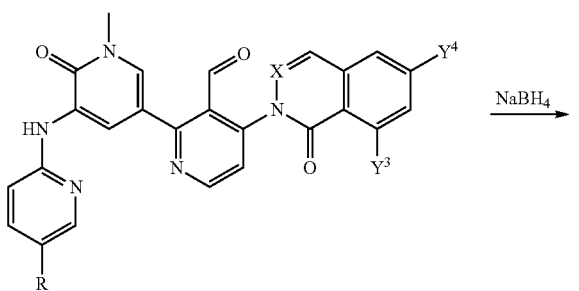
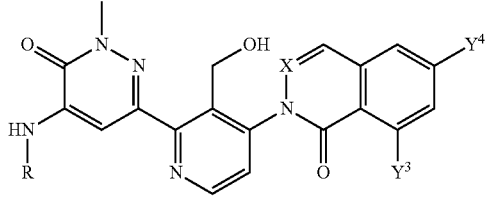
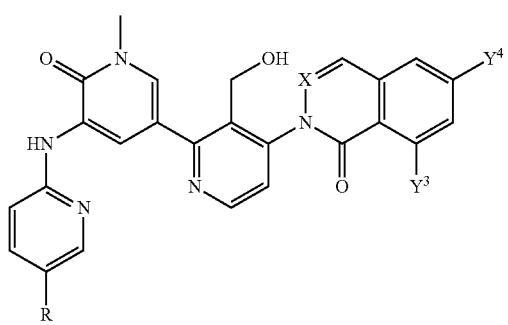
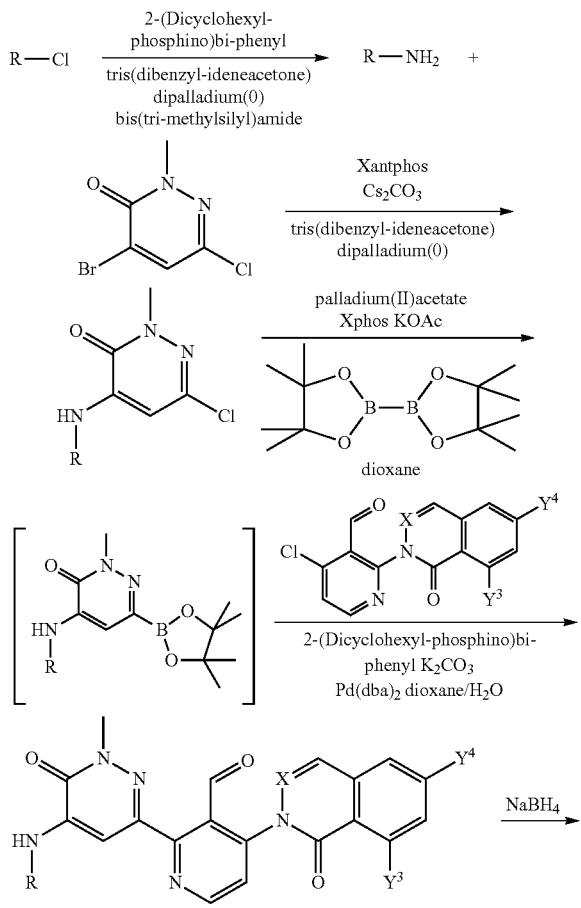

PHARMACEUTICAL COMPOSITIONS AND ADMINISTRATION

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

INDICATIONS AND METHODS OF TREATMENT

The pyridazinone derivatives described herein are kinase inhibitors, in particular Btk inhibitors. These inhibitors can be useful for treating one or more diseases responsive to kinase inhibition, including diseases responsive to Btk inhibition and/or inhibition of B-cell proliferation, in mammals. Without wishing to be bound to any particular theory, it is believed that the interaction of the compounds of the invention with Btk results in the inhibition of Btk activity and thus in the pharmaceutical utility of these compounds. Accordingly, the invention includes a method of treating a mammal, for instance a human, having a disease responsive to inhibition of Btk activity, and/or inhibiting B-cell proliferation, comprising administrating to the mammal having such a disease, an effective amount of at least one chemical entity provided herein. An effective concentration may be ascertained experimentally, for example by assaying blood concentration of the compound, or theoretically, by calculating bioavailability. Other kinases that may be affected in addition to Btk include, but are not limited to, other tyrosine kinases and serine/threonine kinases.

Kinases play notable roles in signaling pathways controlling fundamental cellular processes such as proliferation, differentiation, and death (apoptosis). Abnormal kinase activity has been implicated in a wide range of diseases, including multiple cancers, autoimmune and/or inflammatory diseases, and acute inflammatory reactions. The multifaceted role of kinases in key cell signaling pathways provides a significant opportunity to identify novel drugs targeting kinases and signaling pathways.

An embodiment includes a method of treating a patient having an autoimmune and/or inflammatory disease, or an acute inflammatory reaction responsive to inhibition of Btk activity and/or B-cell proliferation.

Autoimmune and/or inflammatory diseases that can be affected using compounds and compositions according to the invention include, but are not limited to: psoriasis, allergy, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, and myasthenia gravis.

Included herein are methods of treatment in which at least one chemical entity provided herein is administered in combination with an anti-inflammatory agent. Anti-inflammatory agents include but are not limited to NSAIDs, non-specific and COX-2 specific cyclooxygenase enzyme inhibitors, gold compounds, corticosteroids, methotrexate, tumor necrosis factor receptor (TNF) receptors antagonists, immunosuppressants and methotrexate.

Examples of NSAIDs include, but are not limited to, ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors such as celecoxib, valdecoxib, lumiracoxib and/or etoricoxib.

In some embodiments, the anti-inflammatory agent is a salicylate. Salicylates include by are not limited to acetylsalicylic acid or aspirin, sodium salicylate, and choline and magnesium salicylates.

The anti-inflammatory agent may also be a corticosteroid. For example, the corticosteroid may be cortisone, dexamethasone, methylprednisolone, prednisolone, prednisolone sodium phosphate, or prednisone.

In additional embodiments the anti-inflammatory agent is a gold compound such as gold sodium thiomalate or auranofin.

The invention also includes embodiments in which the anti-inflammatory agent is a metabolic inhibitor such as a dihydrofolate reductase inhibitor, such as methotrexate or a dihydroorotate dehydrogenase inhibitor, such as leflunomide.

Other embodiments of the invention pertain to combinations in which at least one anti-inflammatory compound is an anti-C5 monoclonal antibody (such as eculizumab or pexelizumab), a TNF antagonist, such as entanercept, or infliximab, which is an anti-TNF alpha monoclonal antibody.

Still other embodiments of the invention pertain to combinations in which at least one active agent is an immunosuppressant compound such as an immunosuppressant compound chosen from methotrexate, leflunomide, cyclosporine, tacrolimus, azathioprine, and mycophenolate mofetil.

B-cells and B-cell precursors expressing BTK have been implicated in the pathology of B-cell malignancies, including, but not limited to, B-cell lymphoma, lymphoma (including Hodgkin's and non-Hodgkin's lymphoma), hairy cell lymphoma, multiple myeloma, chronic and acute myelogenous leukemia and chronic and acute lymphocytic leukemia.

BTK has been shown to be an inhibitor of the Fas/APO-1 (CD-95) death inducing signaling complex (DISC) in B-lineage lymphoid cells: The fate of leukemia/lymphoma cells may reside in the balance between the opposing proapoptotic effects of caspases activated by DISC and an upstream anti-apoptotic regulatory mechanism involving BTK and/or its substrates (Vassilev et al., *J. Biol. Chem.* 1998, 274, 1646-1656).

It has also been discovered that BTK inhibitors are useful as chemosensitizing agents, and, thus, are useful in combination with other chemotherapeutic drugs, in particular, drugs that induce apoptosis. Examples of other chemotherapeutic drugs that can be used in combination with chemosensitizing BTK inhibitors include topoisomerase I inhibitors (camptothecin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

Btk activity has also been associated with some leukemias expressing the bcr-abl fusion gene resulting from translocation of parts of chromosome 9 and 22. This abnormality is commonly observed in chronic myelogenous leukemia. Btk is constitutively phosphorylated by the bcr-abl kinase which initiates downstream survival signals which circumvents apoptosis in bcr-abl cells. (N. Feldhahn et al. *J. Exp. Med.* 2005 201(11):1837-1852)

EXAMPLES

Commonly used abbreviations include: acetyl (Ac), azo-bis-isobutyrylnitrile (AIBN), atmospheres (Atm), 9-borabicyclo[3.3.1]nonane (9-BBN or BBN), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,4-diazabicyclo[2.2.2]octane (DABCO), diethylaminosulfur trifluoride (DAST), dibenzylideneacetone (dba), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), 2,3-Dichloro-5,6-dicyano-1,4-benzoquinone (DDQ), diethyl azodicarboxylate (DEAD), di-iso-propylazodicarboxylate (DIAD), di-iso-butylaluminumhydride (DIBAL or DIBAL-H), di-iso-propyl-ethylamine (DIPEA), N,N-dimethyl acetamide (DMA), 4-N, N-dimethylaminopyridine (DMAP), N,N-dimethylformamide (DMF), dimethyl sulfoxide (DMSO), 1,1'-bis-(diphenylphosphino)ethane (dppe), 1,1'-bis-(diphenylphosphino)ferrocene (dppf), 1-(3-dimethylaminopropyl)-3-ethylcarbodiimide hydrochloride (EDCI), 2-ethoxy-1-ethoxycarbonyl-1,2-dihydroquinoline (EEDQ), ethyl (Et), ethyl acetate (EtOAc), ethanol (EtOH), 2-ethoxy-2H-quinoline-1-carboxylic acid ethyl ester (EEDQ), diethyl ether ($Et_2O$), ethyl isopropyl ether (EtOiPr), O-(7-azabenzotriazole-1-yl)-N, N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), isopropylmagnesium chloride (iPrMgC1), hexamethyl disilazane (HMDS), liquid chromatography mass spectrometry (LCMS), lithium hexamethyl disilazane (LiHMDS), meta-chloroperoxybenzoic acid (m-CPBA), methanol (MeOH), melting point (mp), $MeSO_2$— (mesyl or Ms), methyl (Me), acetonitrile (MeCN), m-chloroperbenzoic acid (MCPBA), mass spectrum (ms), methyl t-butyl ether (MTBE), methyl tetrahydrofuran (MeTHF), N-bromosuccinimide (NBS), n-Butyllithium (nBuLi), N-carboxyanhydride (NCA), N-chlorosuccinimide (NCS), N-methylmorpholine (NMM), N-methylpyrrolidone (NMP), pyridinium chlorochromate (PCC), Dichloro-((bis-diphenylphosphino)ferrocenyl)palladium(II) ($Pd(dppf)Cl_2$), palladium(II) acetate ($Pd(OAc)_2$), tris(dibenzylideneacetone)dipalladium(0) ($Pd_2(dba)_3$), pyridinium dichromate (PDC), phenyl (Ph), propyl (Pr), iso-propyl (i-Pr), pounds per square inch (psi), pyridine (pyr), 1,2,3,4,5-Pentaphenyl-1'-(di-tert-butylphosphino)ferrocene (Q-Phos), room temperature (ambient temperature, rt or RT), sec-Butyllithium (sBuLi), tert-butyldimethylsilyl or t-BuMe$_2$Si (TBDMS), tetra-n-butylammonium fluoride (TBAF), triethylamine (TEA or $Et_3$ N), 2,2,6,6-tetramethylpiperidine 1-oxyl (TEMPO), triflate or $CF_3$ $SO_2$— (Tf), trifluoroacetic acid (TFA), 1,1'-bis-2,2,6,6-tetramethylheptane-2,6-dione (TMHD), O-benzotriazol-1-yl-N,N,N',N'-tetramethyluronium tetrafluoroborate (TBTU), thin layer chromatography (TLC), tetrahydrofuran (THF), trimethylsilyl or Me$_3$ Si (TMS), p-toluenesulfonic acid monohydrate (TsOH or pTsOH), 4-Me-C$_6$H$_4$SO$_2$— or tosyl (Ts), N-urethane-N-carboxyanhydride (UNCA), and 2-Dicyclohexylphosphino-2',4',6'-triisopropylbiphenyl (XPHOS). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry, IUPAC* 1979 Pergamon Press, Oxford.).

Preparation of I-1

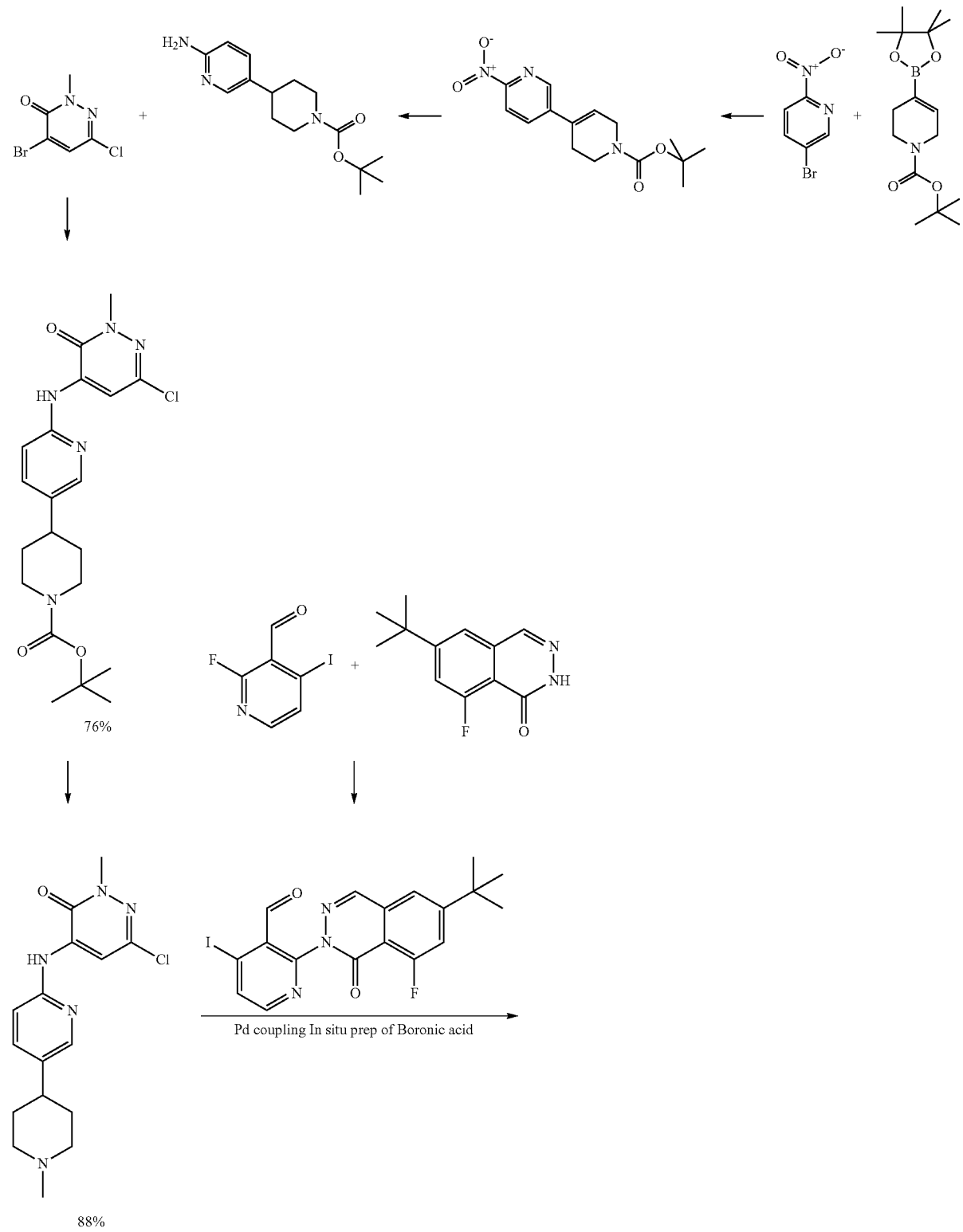

Scheme A

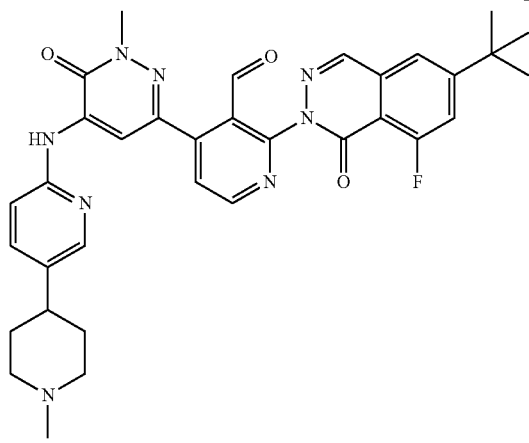
62%

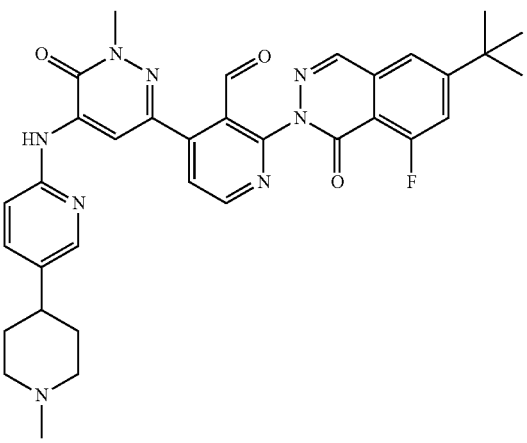
54%

Step 1. Preparation of 6-Nitro-3',6'-dihydro-2'H-[3,4']bipyridinyl-1'-carboxylic acid tert-butyl ester

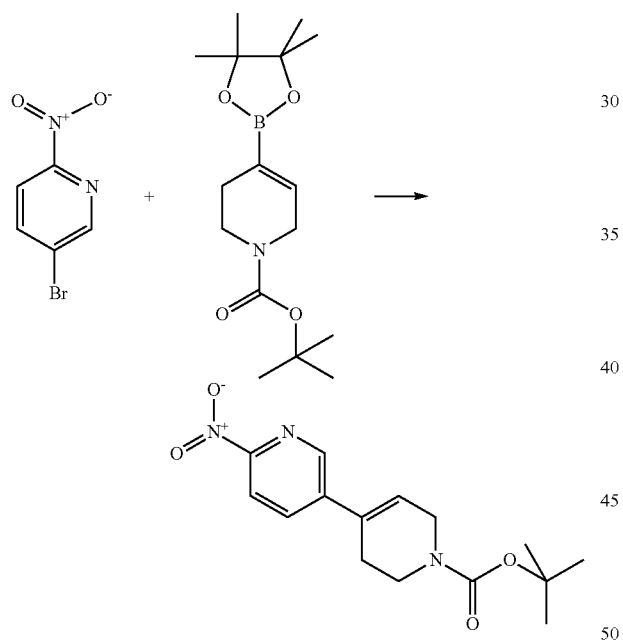

In a 500 mL round-bottomed flask, 5-bromo-2-nitropyridine (6.56 g, 32.3 mmol, Eq: 1) and tert-butyl 4-(4,4,5,5-tetramethyl-1,3,2-dioxaborolan-2-yl)-5,6-dihydropyridine-1(2H)-carboxylate (10 g, 32.3 mmol, Eq: 1.00) were combined with dioxane (160 ml) to give a light yellow solution. $Cs_2 CO_3$ (21.1 g, 64.7 mmol, Eq: 2) and water (6 ml) were added. The reaction mixture was degassed with argon before bis(triphenylphosphine)palladium(II) dichloride (2.27 g, 3.23 mmol, Eq: 0.1) was added. The reaction mixture was heated to 80° C. and stirred for 15 h. The reaction mixture was poured into 500 mL $H_2O$ and extracted with EtOAc (3×200 mL). The combined extracts were washed with brine, dried over $MgSO_4$, filtered and concentrated in vacuo. The crude material was purified by flash chromatography (silica gel, 220 g, 10% to 40% EtOAc in hexanes) to afford a pink solid. The resulting solid was triturated with ether to afford the desired product as a solid (4.8 g). The filtrate from the trituration and mixed fractions from the first chromatography were combined and purified by flash chromatography (silica gel, 220 g, 20% to 40% EtOAc in hexanes) affording additional product (2.2 g). $^1$H NMR (400 MHz, CHLOROFORM-d) δ ppm 1.52 (s, 9 H) 2.59 (d, J=1.52 Hz, 2 H) 3.72 (t, J=5.56 Hz, 2 H) 4.19 (d, J=3.03 Hz, 2 H) 6.35 (br. s., 1 H) 7.97 (dd, J=8.46, 2.40 Hz, 1 H) 8.27 (d, J=8.34 Hz, 1 H) 8.67 (d, J=2.27 Hz, 1 H).

Step 2. Preparation of 6-Amino-3',4',5',6'-tetrahydro-2'H-[3,4']bipyridinyl-1'-carboxylic Acid tert-butyl ester

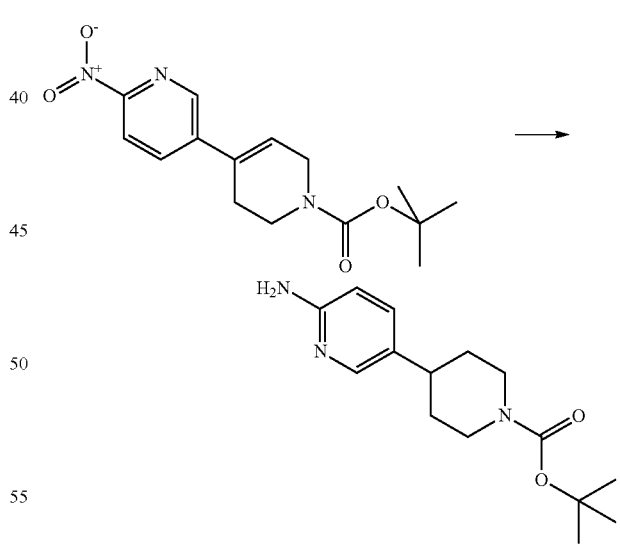

In a 500 mL round-bottomed flask, tert-butyl 4-(6-nitropyridin-3-yl)-5,6-dihydropyridine-1(2H)-carboxylate (4.9 g, 16.0 mmol, Eq: 1.00) in EtOH (300 ml) and ethyl acetate (75 ml) was combined with palladium on carbon (1.32 g, 1.24 mmol, Eq: 0.0773). The reaction mixture was evacuated twice with hydrogen and then stirred with a hydrogen-filled balloon overnight. LC/MS analysis showed that the reaction was complete. The reaction mixture was purged with nitrogen and filtered through celite. The celite cake was washed several times with EtOAc. To the colorless combined filtrate and washes was added $CH_2Cl_2$ and the solution was evaporated to dryness. $CH_2Cl_2$ was added again and the solution was concentrated in vacuo to afford quantitative yield of the desired product. $(M+H)^+=278$ m/e.

Step 3. Preparation of 6-(6-Chloro-2-methyl-3-oxo-2,3-dihydro-pyridazin-4-ylamino)-3',4',5',6'-tetrahydro-2'H-[3,4']bipyridinyl-1'-carboxylic acid tert-butyl ester

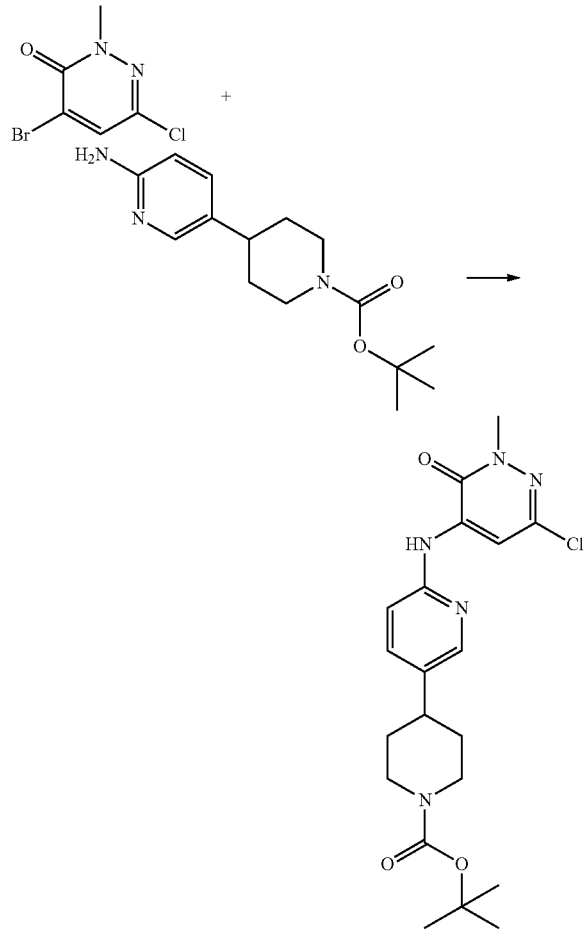

4-Bromo-6-chloro-2-methylpyridazin-3(2H)-one (3.59 g, 16.0 mmol, Eq: 1.00), tert-butyl 4-(6-aminopyridin-3-yl)piperidine-1-carboxylate (4.45 g, 16.0 mmol, Eq: 1.00), 4,5-bis(diphenylphosphino)-9,9-dimethylxanthene (696 mg, 1.2 mmol, Eq: 0.075) and cesium carbonate (18.3 g, 56.2 mmol, Eq: 3.5) were suspended in dioxane (150 ml) under an argon atmosphere. Finally tris(dibenzylideneacetone)dipalladium (0) (551 mg, 602 µmol, Eq: 0.0375) was added. The reaction mixture was heated at 90° C. overnight. The reaction mixture was filtered over celite, and the celite cake was washed with dioxane several times. The combined filtrate and washes were concentrated in vacuo and the resultant solid was triturated with EtOAc, washed with ether and dried in a vacuum oven overnight at 50° C. to afford 4.57 g of the desired product as a white solid. The combined filtrate and washes were evaporated to dryness and dissolved in $CH_2Cl_2$ (4 ml) and the crude material was purified by flash chromatography (silica gel, 120 g Analogix column, 20% to 50% EtOAc in hexanes over 20 min) to afford and additional 582 mg. Total yield (5.15 g, 12.3 mmol, 76.4% yield). $(M+H)^+=420$ m/e; $^1$H NMR (400 MHz, CHLOROFORM-d) δ ppm 1.50 (s, 9 H) 1.54-1.69 (m, 3 H) 1.83 (d, J=13.64 Hz, 2 H) 2.67 (tt, J=12.38, 3.66 Hz, 1 H) 2.83 (t, J=13.14 Hz, 2 H) 3.82 (s, 3 H) 6.89 (d, J=8.59 Hz, 1 H) 7.51 (dd, J=8.46, 2.40 Hz, 1 H) 8.25 (d, J=2.27 Hz, 1 H) 8.27 (br. s., 1 H) 8.30 (s, 1 H).

Step 4a. Preparation of 6-Chloro-2-methyl-4-(1'-methyl-1',2',3',4',5',6'-hexahydro-[3,4']bipyridinyl-6-ylamino)-2H-pyridazin-3-one

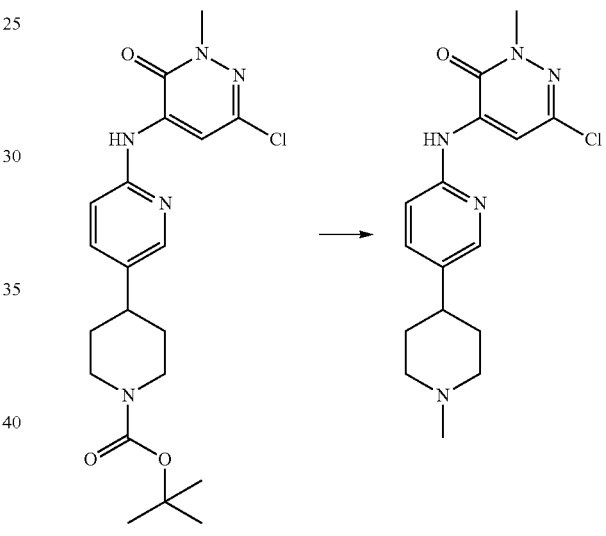

The tert-butyl 4-(6-(6-chloro-2-methyl-3-oxo-2,3-dihydropyridazin-4-ylamino)pyridin-3-yl)piperidine-1-carboxylate (2.0 g, 4.76 mmol, Eq: 1.00) was dissolved in the solvent mixture of formic acid (40.0 ml) and formaldehyde, 37% (80.0 ml). The reaction mixture was stirred at 70° C. overnight until reaction was complete as determined by LCMS analysis, then cooled to ambient temperature. Water was added and the resultant aqueous mixture was washed with $CH_2Cl_2$ and the $CH_2Cl_2$ layer was discarded. The pH of the aqueous layer was adjusted to pH=12 carefully with solid $K_2CO_3$, which resulted in precipitation of a solid. The solid was collected by filtration, washed with water and dried in vacuum oven at 50° C. over 72 h to afford 1.4 g of the desired product. $(M+H)^+=334$ m/e. $^1$H NMR (300 MHz, CHLOROFORM-d) δ ppm 1.84 (dd, J=8.31, 3.02 Hz, 4 H) 1.99-2.19 (m, 2 H) 2.35 (s, 3 H) 2.42-2.68 (m, 1 H) 3.02 (d, J=12.09 Hz, 2 H) 3.81 (s, 3 H) 6.86 (d, J=8.31 Hz, 1 H) 7.52 (dd, J=8.50, 2.46 Hz, 1 H) 8.16-8.33 (m, 3 H).

Step 4b. Preparation of 2-(6-tert-Butyl-8-fluoro-1-oxo-1H-phthalazin-2-yl)-4-iodo-pyridine-3-carbaldehyde

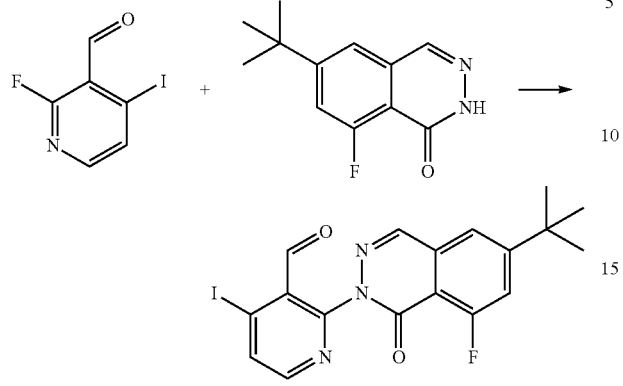

In a 1 L round-bottomed flask, 6-tert-butyl-8-fluorophthalazin-1(2H)-one (5.6 g, 25.4 mmol, Eq: 1.00) was combined with THF (300 ml) to give a colorless solution. Sodium hydride (1.12 g, 28.0 mmol, Eq: 1.1) was added. The reaction mixture was stirred at ambient temperature for 10 min. 2-Fluoro-4-iodonicotinaldehyde (7.02 g, 28.0 mmol, Eq: 1.1) was added and the reaction mixture was stirred at ambient temperature for 1 h. The reaction was complete as determined by LCMS analysis. The reaction mixture was quenched with saturated NH$_4$Cl. The reaction mixture was poured into 200 mL H$_2$O and extracted 3× with CH$_2$Cl$_2$. The organic layers were washed with brine, then dried over Na$_2$SO$_4$ and concentrated in vacuo. The resultant bright yellow solid was transferred into a filter funnel and the flask washed twice with a small volume of EtOAc to ensure complete transfer of the solid into the funnel. The liquid was filtered through. The solid was triturated twice with Et$_2$O and dried under vacuum to afford the desired product as a cream-colored solid (8.09 g, 17.9 mmol, 70.5% yield). (M+H)$^+$=452 m/e. $^1$H NMR (400 MHz, CHLOROFORM-d) δ ppm 1.44 (s, 9 H) 7.49-7.54 (m, 1 H) 7.54 (d, J=1.77 Hz, 1 H) 8.03 (d, J=5.31 Hz, 1 H) 8.30 (d, J=2.53 Hz, 1 H) 8.37 (d, J=5.31 Hz, 1 H) 9.98 (s, 1 H).

Step 5. 2-(6-tert-Butyl-8-fluoro-1-oxo-1H-phthalazin-2-yl)-4-[1-methyl-5-(1'-methyl-1',2',3',4',5',6'-hexahydro-[3,4']bipyridinyl-6-ylamino)-6-oxo-1,6-dihydro-pyridazin-3-yl]-pyridine-3-carbaldehyde

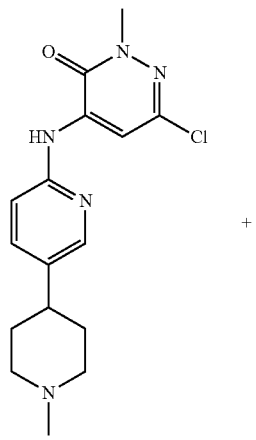

+

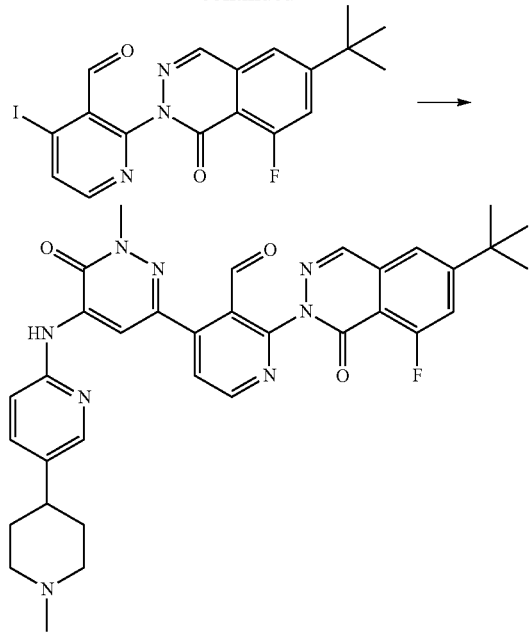

6-Chloro-2-methyl-4-(5-(1-methylpiperidin-4-yl)pyridin-2-ylamino)pyridazin-3(2H)-one (1.4 g, 4.19 mmol, Eq: 1.00), bis(pinacolato)diboron (1.17 g, 4.61 mmol, Eq: 1.1) and potassium acetate (1.23 g, 12.6 mmol, Eq: 3) were suspended in dioxane (60 ml). The reaction mixture was degassed under argon. X-PHOS (300 mg, 629 µmol, Eq: 0.15) and palladium (II) acetate (47.1 mg, 210 µmol, Eq: 0.05) were added and the reaction mixture was stirred at 100° C. (external temperature) for 1 h. under a nitrogen atmosphere. The reaction was monitored closely by LCMS by sampling an aliquot and dissolving it in methanol and looking for disappearance of starting chloride and concurrent appearance of the boronic acid (M+1=344) but being careful to minimize the amount of des-chlorinated side product (M+1=300). The reaction was complete after 1 h. The temperature of the heating bath was turned down to 80° C. and the flask was raised out of the heating bath, but continued stirring. 2-(6-tert-Butyl-8-fluoro-1-oxophthalazin-2(1H)-yl)-4-iodonicotinaldehyde (1.89 g, 4.19 mmol, Eq: 1.00) and potassium carbonate (1.74 g, 12.6 mmol, Eq: 3) were added, followed by water (6.00 ml). Tricyclohexylphosphine (118 mg, 419 µmol, Eq: 0.1) and bis(dibenzylideneacetone)palladium (121 mg, 210 µmol, Eq: 0.05) were added. The reaction mixture was heated with vigorous stirring at 80° C. and stirred 2 h and then the reaction mixture was cooled to ambient temperature. The reaction mixture was poured onto water and extracted with gentle shaking into EtOAc (2×). The combined EtOAc extracts were washed with brine. The aqueous phase was extracted 3× with CH$_2$Cl$_2$. The CH$_2$Cl$_2$ and ethyl acetate layers were combined and the combined organic layers were dried over Na$_2$SO$_4$ and concentrated in vacuo. The crude material was slurried in 50 ml CH$_2$Cl$_2$ and 200 ml Et$_2$O was added. The solid was filtered and washed with Et$_2$O. A second batch of solid precipitated out and was collected by filtration and washed with ether. Both batches had similar LCMS and $^1$H-nmr spectra, which were consistent with desired product, and they were combined to afford 1.62 g of product. (M+H)$^+$=623 m/e. $^1$H NMR (300 MHz, CHLOROFORM-d) δ ppm 1.42 (s, 9 H) 1.88 (br. s., 3 H) 2.39 (br. s., 3 H) 2.46-2.64 (m, 1 H) 3.05 (br. s., 2 H) 3.89 (s, 3 H) 6.91 (d, J=8.31 Hz, 1 H) 7.38-7.66 (m, 3 H) 7.76

(d, J=5.29 Hz, 1 H) 8.19-8.38 (m, 3 H) 8.81 (s, 1 H) 8.87 (d, J=5.29 Hz, 1 H) 10.11 (s, 1 H).

Example 1

Step 6. 6-tert-Butyl-8-fluoro-2-{3-hydroxymethyl-4-[1-methyl-5-(1'-methyl-1',2',3',4',5',6'-hexahydro-[3,4']bipyridinyl-6-ylamino)-6-oxo-1,6-dihydro-pyridazin-3-yl]-pyridin-2-yl}-2H-phthalazin-1-one

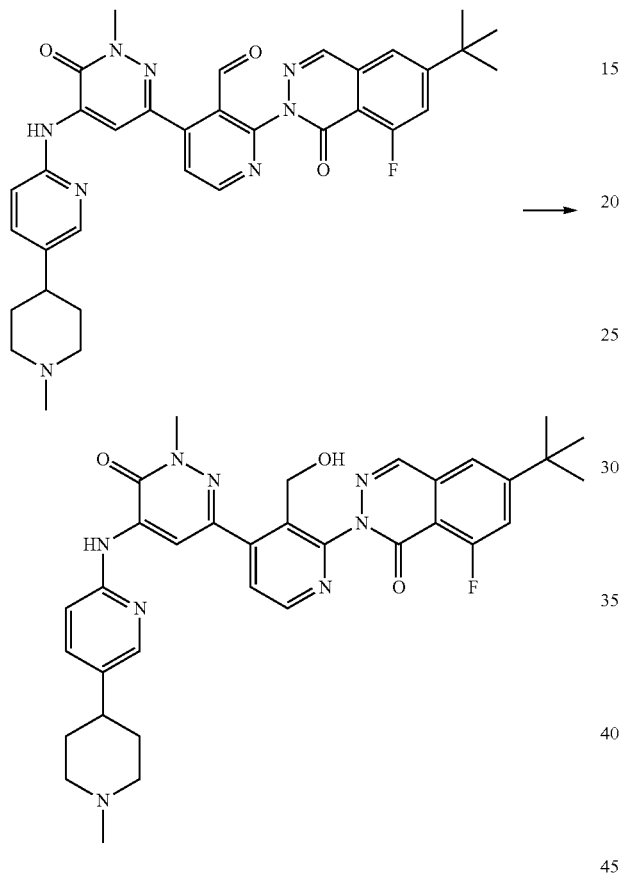

In a 250 mL round-bottomed flask, 2-(6-tert-butyl-8-fluoro-1-oxophthalazin-2(1H)-yl)-4-(1-methyl-5-(5-(1-methylpiperidin-4-yl)pyridin-2-ylamino)-6-oxo-1,6-dihydropyridazin-3-yl)nicotinaldehyde (1.62 g, 2.6 mmol, Eq: 1.00) was combined with dry $CH_2Cl_2$ (45 ml) and dry MeOH (20 mL) to give a brown solution. Sodium borohydride (177 mg, 4.68 mmol, Eq: 1.8) was added and the reaction was stirred at ambient temperature for 1 h before being quenched with sat'd $NH_4Cl$. The reaction mixture was diluted with 50 mL $H_2O$ and extracted with $CH_2Cl_2$ (3×150 mL). The organic layers were dried over $Na_2SO_4$ and concentrated in vacuo. The crude material was purified by flash chromatography [silica gel, 80 g, 0% to 50% (60:10:1 $CH_2Cl_2$:MeOH: $NH_{40}H$) in $CH_2Cl_2$] to afford a slightly impure foam. The foam was slurried in ml $Et_2O$ and 10 ml EtOAc and stirred slowly with a heavy stir bar for 1 h resulting in a white solid. The solid was collected by filtration, dried under vacuum at 50° C. for 48 h. to afford the desired product as a white solid (880 mg). $(M+H)^+$=625 m/e.
$^1H$ NMR (300 MHz, CHLOROFORM-d) δ ppm 1.44 (s, 9 H) 1.87 (br. s., 3 H) 2.15 (br. s., 2 H) 2.39 (br. s., 3 H) 2.52 (t, J=7.74 Hz, 1 H) 3.04 (br. s., 2 H) 3.82-3.91 (m, 1 H) 3.93 (s, 3 H) 4.46-4.63 (m, 2 H) 6.93 (d, J=8.69 Hz, 1 H) 7.42-7.59 (m, 3 H) 7.64 (d, J=4.91 Hz, 1 H) 8.15-8.39 (m, 3 H) 8.70 (s, 1 H) 8.73 (d, J=4.91 Hz, 1 H)

Preparation of I-2

Scheme B

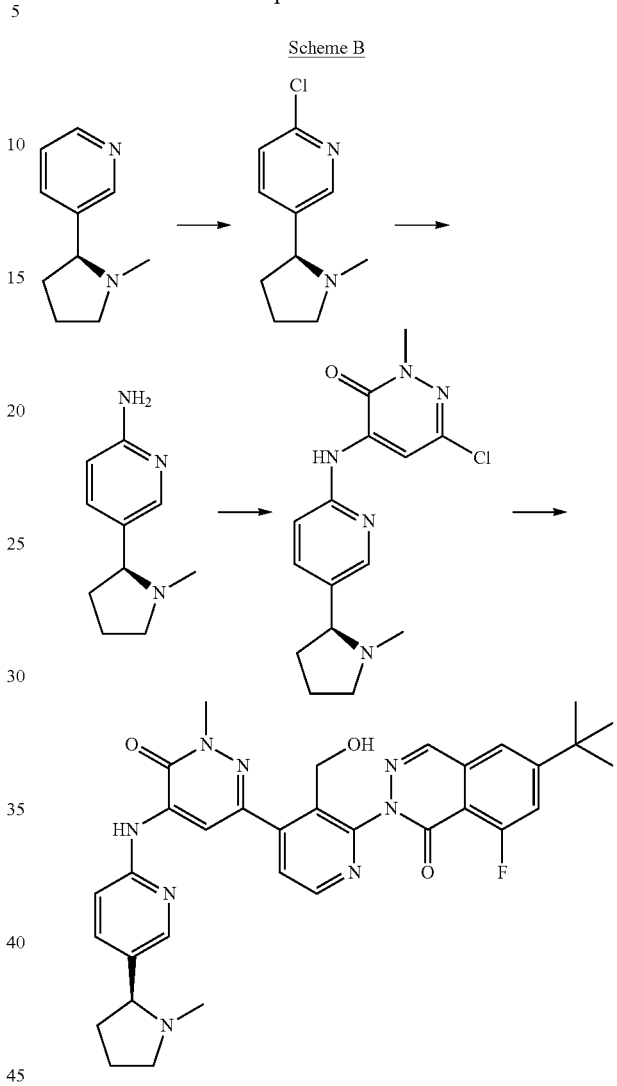

Step 1. Preparation of. 2-Chloro-5-((S)-1-methyl-pyrrolidin-2-yl)-pyridine

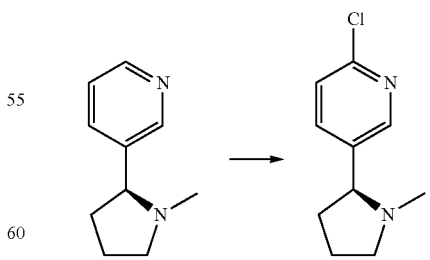

A 100 mL round-bottomed flask was placed under an argon atmosphere and degassed with argon by vacuum. The solvents (hexanes (4 ml) and toluene 12 ml)) were added to the flask. N,N-dimethylethanolamine (1.07 g, 1.21 ml, 12.0 mmol) was added. The reaction mixture was cooled to 0° C.

N-Butyl lithium (8.66 ml of 2.5M in hexanes, 21.6 mmol) was added. The reaction mixture was stirred at 0° C. for 30 min. The reaction mixture was cooled to −20° C. (S)-3-(1-methylpyrrolidin-2-yl)pyridine (650 mg, 0.64 ml, 4.01 mmol) was added. The reaction mixture was stirred −20° C. for 1 h. The reaction mixture was cooled to −78° C. and hexachloroethane (3.8 g, 16.0 mmol) was added in toluene (8 ml). The reaction mixture was stirred at −78° C. for 1 h. The reaction was quenched cold with satd. NaHCO₃ (4 mL). LCMS showed that the reaction gave the desired regioisomer in a 6:1 ratio over the undesired 6-chloro pyridine product. The reaction mixture was poured into 50 mL H₂O and extracted with CH₂Cl₂ (3×125 mL). The organic layers were dried over Na₂SO₄ and concentrated in vacuo. The crude material was purified by flash chromatography (silica gel, 40 g, 0% to 55% EtOAc in hexanes) to afford the desired product (467 mg, 59%). ¹H NMR (300 MHz, CHLOROFORM-d) δ ppm 1.56-2.05 (m, 3 H) 2.16-2.40 (m and overlapping s, 5 H) 3.09 (t, J=8.31 Hz, 1 H) 3.17-3.29 (m, 1 H) 7.23-7.32 (m, 1 H) 7.68 (dd, J=8.12, 2.45 Hz, 1 H) 8.30 (d, J=2.27 Hz, 1 H)

Step 2. Preparation o. 5-((S)-1-Methyl-pyrrolidin-2-yl)-pyridin-2-ylamine

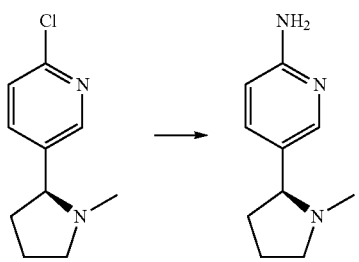

In a 75 mL sealed tube, (S)-2-chloro-5-(1-methylpyrrolidin-2-yl)pyridine (622 mg, 3.16 mmol) and 2-(dicyclohexylphosphino)biphenyl (222 mg, 633 μmol) were combined with THF (15 ml) to give a light yellow solution. The solution was degassed with argon. Tris(dibenzylideneacetone)dipalladium (0) (290 mg, 316 μmol) was added. LiHMDS (9.49 ml of 1M solution in THF, 9.49 mmol) was added. The reaction was placed under an argon atmosphere and sealed. The reaction mixture was heated to 90° C. and stirred for 15 h. The reaction was complete by tlc. The reaction mixture was cooled to room temperature and diluted with EtOAc. The reaction mixture was poured into 150 mL sat NH₄Cl and extracted with EtOAc (4×75 mL). The organic layers were dried over MgSO₄ and concentrated in vacuo. The crude material was purified by flash chromatography with stepwise gradient (silica gel, 40 g, 10% to 50% (60:10:1 CH₂Cl₂: methanol: NH₄OH)/CH₂Cl₂) gradient to afford the desired product (560 mg, 99%). ¹H NMR (300 MHz, CHLOROFORM-d) δ ppm 1.57-2.03 (m, 3 H) 2.04-2.39 (m and overlapping s, 5 H) 2.92 (t, J=8.12 Hz, 1 H) 3.14-3.29 (m, 1 H) 4.40 (br. s., 2 H) 6.51 (d, J=8.69 Hz, 1 H) 7.47 (dd, J=8.31, 2.27 Hz, 1 H) 7.95 (d, J=2.27 Hz, 1 H)

Step 3. Preparation of 6-Chloro-2-methyl-4-[5-((S)-1-methyl-pyrrolidin-2-yl)-pyridin-2-ylamino]-2H-pyridazin-3-one

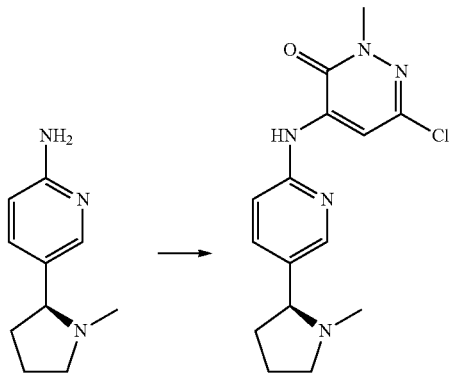 [SMILES: CN1CCC[C@H]1c1ccc(N)nc1 ; CN1CCC[C@H]1c1ccc(Nc2cc(Cl)nn(C)c2=O)nc1]

In a 50 mL round-bottomed flask, 5-((S)-1-methyl-pyrrolidin-2-yl)-pyridin-2-ylamine (560 mg, 3.16 mmol), 4-bromo-6-chloro-2-methylpyridazin-3(2H)-one (847 mg, 3.79 mmol) and cesium carbonate (3.09 g, 9.48 mmol) were combined with dioxane (25 ml) to give a orange suspension. 4,5-Bis(diphenylphosphino)-9,9-dimethylxanthene (274 mg, 474 μmol, Eq: 0.15) was added followed by tris(dibenzylideneacetone)dipalladium(0) (145 mg, 158 μmol, Eq: 0.05). The reaction was degassed with argon for 10 min and heated at 95-105° C. for 4 h. No aniline starting material remained. The reaction mixture was diluted with 200 ml CH₂Cl₂. MgSO₄ was added and the mixture was stirred for 5 min. The reaction was filtered and the filtercake was washed several times with CH₂Cl₂. The combined filtrate and washes were concentrated in vacuo. The crude material was purified by flash chromatography (silica gel, 40 g, 1% to 2% MeOH in CH₂Cl₂) to afford the desired product (522 mg, 52%). (M+H)⁺=320 m/e.

Example 2

Step 4. Preparation of 6-tert-Butyl-8-fluoro-2-(3-hydroxymethyl-4-{1-methyl-5-[5-((S)-1-methyl-pyrrolidin-2-yl)-pyridin-2-ylamino]-6-oxo-1,6-dihydro-pyridazin-3-yl}-pyridin-2-yl)-2H-phthalazin-1-one.

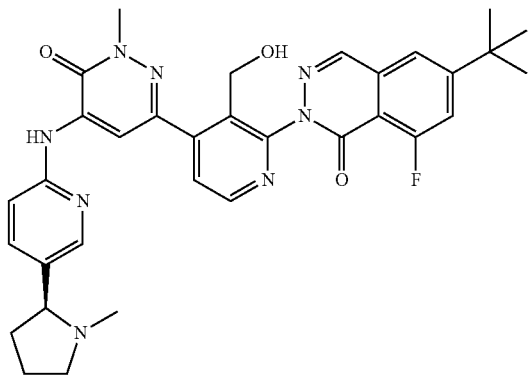 [SMILES: CN1CCC[C@H]1c1ccc(Nc2cc(-c3ccnc(-n4ncc5cc(C(C)(C)C)cc(F)c5c4=O)c3CO)nn(C)c2=O)nc1]

Preparation by a similar procedure to example 1 (Step 5-6), except substituting 6-chloro-2-methyl-4-[5-((S)-1-methylpyrrolidin-2-yl)-pyridin-2-ylamino]-2H-pyridazin-3-one for 6-Chloro-2-methyl-4-(5-(1-methylpiperidin-4-yl)pyridin-2-ylamino)pyridazin-3(2H)-one in step 5 afforded 85 mg of the title compound as a white solid. (M+H)⁺=611 m/e. ¹H NMR ¹H NMR (300 MHz, CHLOROFORM-d) δ ppm 1.41-1.46 (m, 9 H) 2.19 (br. s., 3 H) 2.98-3.34 (m, 1 H) 3.88 (s, 1 H) 3.93 (s, 3 H) 4.46-4.64 (m, 2 H) 6.97 (d, J=8.31 Hz, 1 H) 7.43-7.79 (m, 4 H) 8.21-8.38 (m, 3 H) 8.65-8.84 (m, 2 H) (M+H)⁺=611 m/e.

Preparation of I-3

Step 1. Preparation of 6-Chloro-2-methyl-4-[5-(morpholine-4-carbonyl)-pyridin-2-ylamino]-2H-pyridazin-3-one

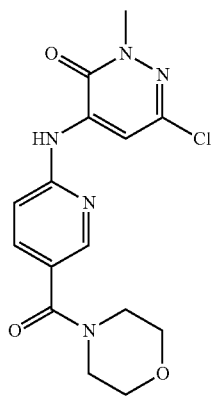 [SMILES: Cn1nc(Cl)cc(Nc2ccc(C(=O)N3CCOCC3)cn2)c1=O]

(6-Aminopyridin-3-yl)(morpholino)methanone (58 g, 280 mmol, Eq: 1.00), 4-bromo-6-chloro-2-methylpyridazin-3 (2H)-one (63.66 g, 285 mmol, Eq: 1.02) and (9,9-dimethyl-9H-xanthene-4,5-diyl)bis(diphenylphosphine) (4.86 g, 8.4 mmol, Eq: 0.03) were dissolved in DMF (1.1 l) under heating. Cesium carbonate (274 g, 840 mmol, Eq: 3) was added. Finally Pd₂(dba)₃ (3.84 g, 4.2 mmol, Eq: 0.015) was added under an argon atmosphere. The reaction mixture was heated to 93° C. (internal temperature) for 3 hr. The warm reaction mixture was poured into water/ice (10 l). A beige precipitate was collected by filtration and washed with water (2 l). The resulting solid was taken up in DCM (5 l) and filtered. The filtrate was concentrated in vacuo to give a solid, which was triturated with isopropanol (700 ml), filtered and dried under vacuum to afford the desired product (70.24 g) as a beige solid. (M+H)⁺=350 m/e. ¹H NMR (300 MHz, CHLOROFORM-d) δ ppm 3.56-3.79 (m, 8 H) 3.83 (s, 3 H) 6.96 (d, J=8.31 Hz, 1 H) 7.77 (dd, J=8.31, 2.27 Hz, 1 H) 8.34-8.42 (m, 2 H) 8.47 (d, J=2.27 Hz, 1 H).

Example 3

Preparation of 6-tert-Butyl-8-fluoro-2-(3-hydroxymethyl-4-{1-methyl-5-[5-(morpholine-4-carbonyl)-pyridin-2-ylamino]-6-oxo-1,6-dihydro-pyridazin-3-yl}-pyridin-2-yl)-2H-phthalazin-1-one

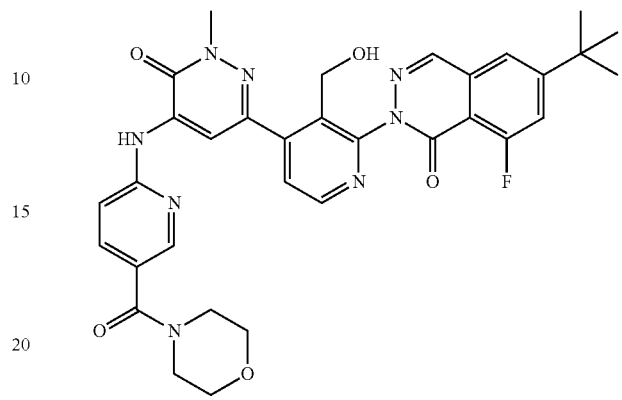

Preparation by a similar procedure to example 1 (Step 5-6), except substituting 6-chloro-2-methyl-4-[5-(morpholine-4-carbonyl)-pyridin-2-ylamino]-2H-pyridazin-3-one for 6-chloro-2-methyl-4-(5-(1-methylpiperidin-4-yl)pyridin-2-ylamino)pyridazin-3(2H)-one in step 5 afforded 165 mg of the title compound as a white solid. (M+H)⁺=641 m/e. ¹H NMR (300 MHz, CHLOROFORM-d) δ ppm 1.44 (s, 9 H) 3.54-3.84 (m, 8 H) 3.94 (s, 3 H) 4.57 (s, 2 H) 7.03 (d, J=8.69 Hz, 1 H) 7.45-7.59 (m, 2 H) 7.64 (d, J=4.91 Hz, 1 H) 7.79 (dd, J=8.69, 2.27 Hz, 1 H) 8.33 (d, J=2.64 Hz, 1 H) 8.41-8.55 (m, 2 H) 8.74 (d, J=4.91 Hz, 1 H) 8.77 (s, 1 H).

Preparation of I-4

Step 1. Preparation of 6-chloro-4-(5-methanesulfonyl-pyridin-2-ylamino)-2-methyl-2H-pyridazin-3-one

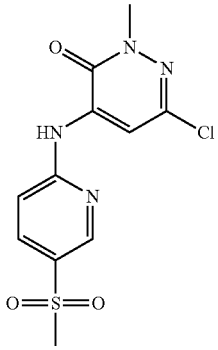 [SMILES: Cn1nc(Cl)cc(Nc2ccc(S(C)(=O)=O)cn2)c1=O]

In a round-bottom flask under argon was placed 1.14 g 95% sodium hydride in oil dispersion and 90 mL of tetrahydrofuran (Aldrich, anhydrous, no inhibitor). The mixture was cooled in an ice bath and 3.10 g 5-(methylsulfonyl)pyridin-2-amine was added one portion. The cooling bath was removed and the mixture stirred at room temperature. After 15 minutes the mixture was cooled in an ice bath and 4.103 g of 4-bromo-6-chloro-2-methylpyridazin-3(2H)-one was added in one portion. The cooling bath was removed and the mixture stirred at room temperature. After 90 minutes, the mixture was cooled in an ice bath and quenched by the dropwise addition of 90 mL of 0.5 M hydrochloric acid (gas evolution at first few drops, color change from red-brown to light tan, 15 minute addition). The cooling bath was removed, the mixture stirred for an additional 15 minutes and the solid collected by suction filtration, washing with water, then ether. The solid was air dried overnight to afford the desired product (5.05 g) as a light yellow solid. $^1$H NMR (300 MHz, DMSO-$d_6$) δ ppm 3.25 (s, 3 H) 3.69 (s, 3 H) 7.73 (d, J=8.69 Hz, 1 H) 8.16 (dd, J=1.00 Hz, 1 H) 8.42 (s, 1 H) 8.83 (d, J=2.27 Hz, 1 H).

Example 4

Preparation of 6-tert-Butyl-8-fluoro-2-{3-hydroxymethyl-4-[5-(5-methanesulfonyl-pyridin-2-ylamino)-1-methyl-6-oxo-1,6-dihydro-pyridazin-3-yl]-pyridin-2-yl}-2H-phthalazin-1-one

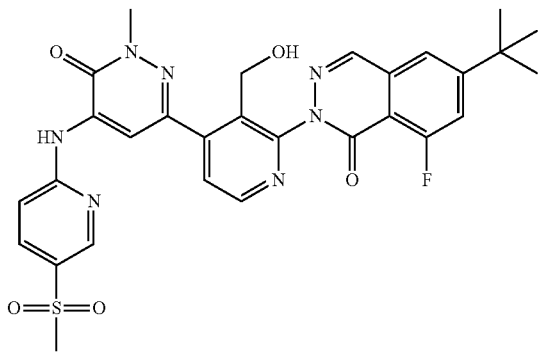 [SMILES: Cn1nc(-c2ccnc(-n3ncc4cc(C(C)(C)C)cc(F)c4c3=O)c2CO)cc(Nc2ccc(S(C)(=O)=O)cn2)c1=O]

Preparation by a similar procedure to example 1 (Step 5-6), except substituting 6-chloro-4-(5-methanesulfonyl-pyridin-2-ylamino)-2-methyl-2H-pyridazin-3-one for 6-chloro-2-methyl-4-(5-(1-methylpiperidin-4-yl)pyridin-2-ylamino)pyridazin-3(2H)-one in step 5 afforded 65 mg of the title compound as a white solid. (M+H)$^+$=606 m/e. $^1$H NMR (300 MHz, CHLOROFORM-d) δ ppm 1.44 (s, 9 H) 3.11 (s, 3 H) 3.96 (s, 3 H) 4.58 (s, 2 H) 7.09 (d, J=9.06 Hz, 1 H) 7.49-7.59 (m, 2 H) 7.64 (d, J=4.91 Hz, 1 H) 8.11 (dd, J=8.69, 2.27 Hz, 1 H) 8.34 (d, J=2.64 Hz, 1 H) 8.64 (s, 1 H) 8.75 (d, J=4.91 Hz, 1H) 8.91 (s, 2 H).

Preparation of I-5

Step 1. Preparation of 6-Chloro-N,N-dimethyl-nicotinamide

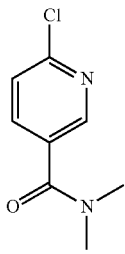

In a 500 mL round-bottomed flask, 6-chloronicotinoyl chloride (8 g, 45.5 mmol, Eq: 1.00) was dissolved in DCM (200 ml) under argon and cooled to 0° C. To this solution, dimethylamine (90.9 ml of 2M in THF, 182 mmol, Eq: 4) was added drop-wise over 15 min maintaining the temperature below 10° C. The ice bath was removed and the reaction was stirred for 3 h.

The reaction mixture was washed with water (100 mL), 20% potassium carbonate (200 mL), and water (100 mL) and dried over Na$_2$SO$_4$. The solvent was removed to give a yellow oil which solidified on standing. $^1$H NMR (300 MHz, CHLOROFORM-d) δ ppm 2.76-3.27 (m, 6 H) 7.38 (d, J=8.31 Hz, 1 H) 7.74 (dd, J=8.12, 2.46 Hz, 1 H) 8.46 (d, J=2.64 Hz, 1 H)

Step 2. Preparation of 6-Azido-N,N-dimethyl-nicotinamide

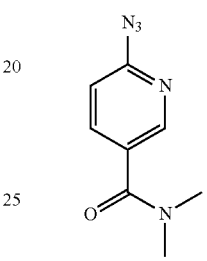

In a 500 mL round-bottomed flask, 6-chloro-N,N-dimethylnicotinamide (8.15 g, 44.1 mmol) was combined with DMF (50.0 ml) to give a brown solution. Sodium azide (3.44 g, 53.0 mmol) was added and the reaction mixture was heated to 120° C. and stirred for 60 h. The reaction mixture was diluted with 100 mL H$_2$O and extracted with EtOAc (2×200 mL). The organic layers were combined, washed with H$_2$O (1×50 mL), sat NaCl (1×100 mL), dried over Na$_2$SO$_4$ and concentrated in vacuo to a yellow oil. MeOH was added and the entire mixture solidified upon concentration. The crude product was dried under vacuum overnight. The pasty solid was recrystallized from EtOAc/Hex. The solid was filtered and washed with a minimal amount of hexane. The white powder was dried under vacuum at 45° C. for 3 hrs to give 2.23 g (26%) of the title compound. $^1$H NMR (300 MHz, CHLOROFORM-d) δ: 8.95 (s, 1H), 8.09 (d, J=9.1 Hz, 1H), 7.75 (dd, J=9.1, 1.5 Hz, 1H), 3.15 (br. s., 6H).

Step 3. Preparation of 6-Amino-N,N-dimethyl-nicotinamide

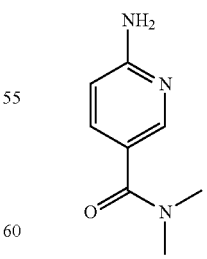

In a 250 mL round-bottomed flask, 6-azido-N,N-dimethylnicotinamide (2.26 g, 11.8 mmol) was combined with ethyl acetate (50 ml) and methanol (30 ml) to give a yellow solution. 10% Pd/C (200 mg, 1.88 mmol) was added and the reaction mixture was evacuated and filled with H$_2$ twice. The reaction mixture was stirred under balloon pressure of H₂ at 25° C. for 17 h. The reaction mixture was filtered through celite and the filter cake was washed with MeOH. The filtrate was concentrated in vacuo and the cream colored solid was dried under vacuum at 45° C. for 3 hrs to give the title compound in quantitative yield. (M+H)⁺=166 m/e. ¹H NMR (300 MHz, CHLOROFORM-d) δ: 8.21 (d, J=2.3 Hz, 1H), 7.59 (dd, J=8.3, 2.3 Hz, 1H), 6.50 (d, J=8.7 Hz, 1H), 4.69 (br. s., 2H), 3.08 (s, 6H).

Example 5

Preparation of 6-{6-[2-(6-tert-Butyl-8-fluoro-1-oxo-1H-phthalazin-2-yl)-3-hydroxymethyl-pyridin-4-yl]-2-methyl-3-oxo-2,3-dihydro-pyridazin-4-ylamino}-N,N-dimethyl-nicotinamide

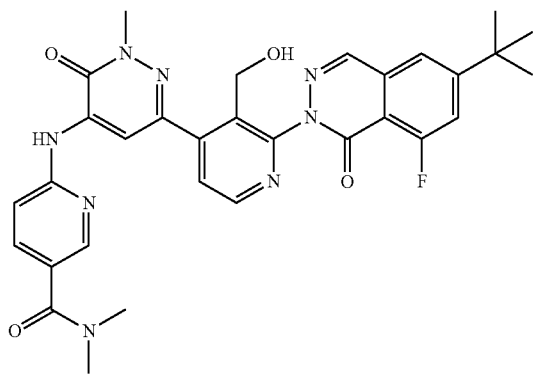

Preparation by a similar procedure to example 3 except substituting 6-amino-N,N-dimethyl-nicotinamide for (6-Aminopyridin-3-yl)(morpholino)methanone afforded 163 mg of the title compound as a white solid. (M+H)⁺=599 m/e. ¹H NMR (300 MHz, CHLOROFORM-d) δ ppm 1.43 (s, 9 H) 3.12 (s, 6 H) 3.94 (s, 3 H) 4.57 (s, 2 H) 7.00 (d, J=8.69 Hz, 1 H) 7.48-7.59 (m, 2 H) 7.64 (d, J=4.91 Hz, 1 H) 7.80 (dd, J=8.50, 2.08 Hz, 1 H) 8.32 (d, J=2.27 Hz, 1 H) 8.42-8.51 (m, 2 H) 8.74 (d, J=5.29 Hz, 1 H) 8.78 (s, 1 H).

Preparation of I-6

Step 1. 2-(6-Cyclopropyl-8-fluoro-1-oxo-1H-isoquinolin-2-yl)-4-iodo-pyridine-3-carbaldehyde

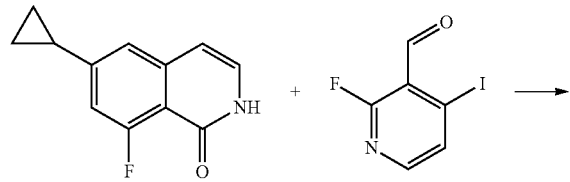 →

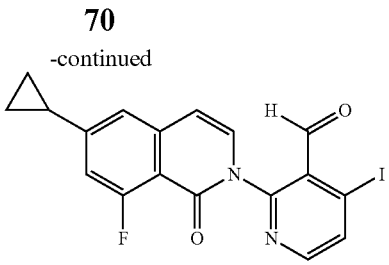

In a 50 mL round-bottomed flask, 6-cyclopropyl-8-fluoroisoquinolin-1(2H)-one¹(364 mg, 1.79 mmol, Eq: 1.00) was combined with THF (13.00 ml) to give a slightly cloudy colorless solution. Lithium bis(trimethylsilyl)amide in THF (2.15 ml of 1M, 2.15 mmol, Eq: 1.2) was added. Stirred at ambient temperature for 20 min. 2-Fluoro-4-iodonicotinaldehyde (629 mg, 2.51 mmol, Eq: 1.4) in 5 mL THF was added. The reaction mixture was heated to 65° C. and stirred for 3 h before being allowed to cool to RT. The reaction was quenched with saturated NH₄Cl, extracted one time with EtOAc and three times with dichloromethane. The combined organic layer was washed with brine, dried over Na₂SO₄ and concentrated in vacuo. The crude material was purified by flash chromatography (silica gel, 80 g, 1% to 2% MeOH in DCM) and then foamed with EtOAc to afford the desired product (90% pure, 423 mg) as a light yellow powder. The product was used as is in the next step. (M+H)⁺=435 m/e. ¹H NMR (300 MHz, CHLOROFORM-d) δ ppm 0.74-0.92 (m, 2 H) 1.03-1.20 (m, 2 H) 1.91-2.05 (m, 1 H) 6.56 (dd, J=7.74, 2.08 Hz, 1 H) 6.78 (dd, J=12.84, 1.51 Hz, 1 H) 7.02 (d, J=1.51 Hz, 1 H) 7.51 (d, J=7.93 Hz, 1 H) 7.89 (d, J=5.29 Hz, 1 H) 8.25 (d, J=5.29 Hz, 1 H) 9.91 (s, 1 H).

Example 6

Step 2. Preparation of 6-{6-[2-(6-Cyclopropyl-8-fluoro-1-oxo-1H-isoquinolin-2-yl)-3-hydroxymethyl-pyridin-4-yl]-2-methyl-3-oxo-2,3-dihydro-pyridazin-4-ylamino}-N,N-dimethyl-nicotinamide Preparation by a similar procedure to example 1 (Step 5-6), except substituting 6-(6-Chloro-2-methyl-3-oxo-2,3-dihydro-pyridazin-4-ylamino)-N,N-dimethyl-nicotinamide for 6-chloro-2-methyl-4-(5-(1-methylpiperidin-4-yl)pyridin-2-ylamino)pyridazin-3(2H)-one and substituting 2-(6-cyclopropyl-8-fluoro-1-oxo-1H-isoquinolin-2-yl)-4-iodo-pyridine-3-carbaldehyde for 2-(6-tert-butyl-8-fluoro-1-oxophthalazin-2(1H)-yl)-4-iodonicotinaldehyde in step 5 afforded 148 mg of the title compound as a white solid. (M+H)⁺=582 m/e. ¹H NMR (300 MHz, CHLOROFORM-d) δ ppm 0.81-0.93 (m, 2 H) 1.06-1.21 (m, 2 H) 1.90-2.14 (m, 1 H) 3.34-3.56 (m, 1 H) 3.94 (s, 3 H) 4.40-4.66 (m, 6 H)

6.51-6.62 (m, 1 H) 6.82 (d, J=12.84 Hz, 1 H) 7.02 (d, J=8.69 Hz, 1 H) 7.07 (s, 1 H) 7.19-7.31 (m, 4 H) 7.61 (d, J=4.91 Hz, 1 H) 7.80 (dd, J=8.31, 2.27 Hz, 1 H) 8.42-8.52 (m, 2 H) 8.69 (dd, J=4.91, 0.76 Hz, 1 H) 8.78 (s, 1 H).

Preparation of I-7 lithium in cyclohexanes (31.4 ml of 1.4 M, 43.9 mmol, Eq: 2.05) was added dropwise slowly and with a stream of $N_2$. A yellow solution resulted. The reaction mixture was warmed to −15° C. for 1 h. A pale yellow suspension resulted. The reaction mixture was cooled back down to −78° C. Dry DMF (3.13 g, 3.32 ml, 42.9 mmol, Eq: 2) was added dropwise. The

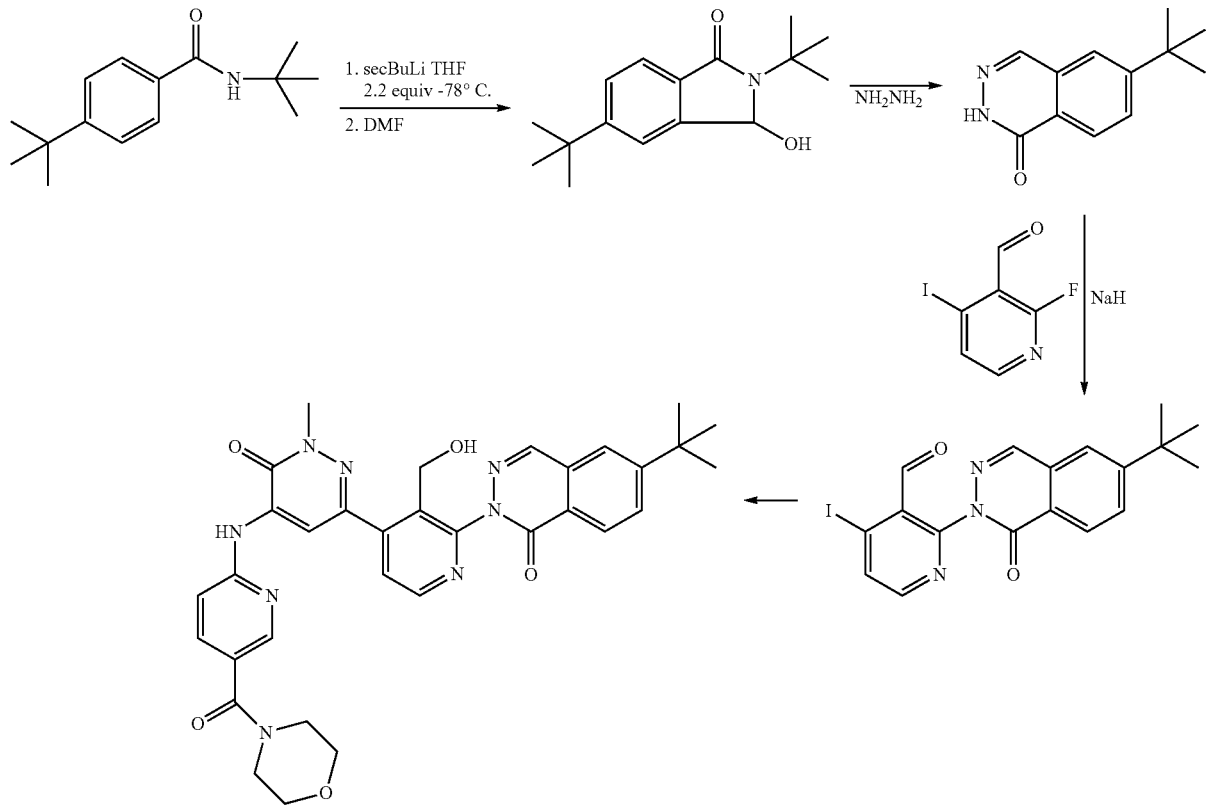

Scheme C

Step 1. Preparation of 2,5-di-tert-butyl-3-hydroxyl-2,3-dihydro-isoindol-1-one

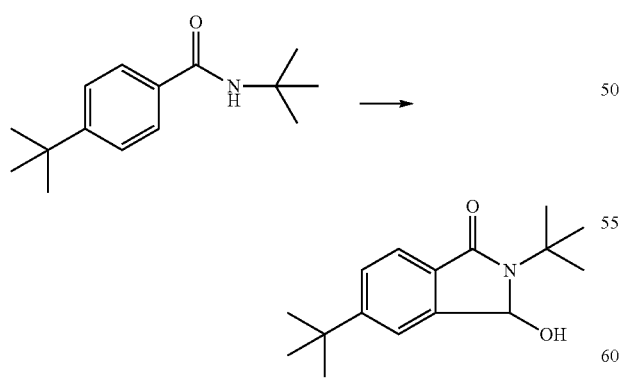

In a 1 L three-necked flask fitted with an addition funnel with line to a bubbler, and a nitrogen inlet, that was purged with $N_2$, N,4-di-tert-butylbenzamide (5 g, 21.4 mmol, Eq: 1.00) was combined with THF (200 ml) to give a light yellow solution. The reaction was cooled to −78° C. The sec-butylreaction mixture was allowed to warm to room temperature. 30 mL of saturated $NH_4Cl$ was added slowly at 0° C. The reaction mixture was poured into 150 mL $H_2O$ and extracted with EtOAc (3×250 mL). The combined organic extracts were washed with brine, dried over $MgSO_4$ and concentrated in vacuo. The crude material was purified by flash chromatography (silica gel, 80 g, 0% to 40% EtOAc in hexanes to afford the desired product (4.9 g, 88% yield). $(M+H)^+=262$ m/e.

Step 2. Preparation of 6-tert-butyl-2H-phthalazin-1-one

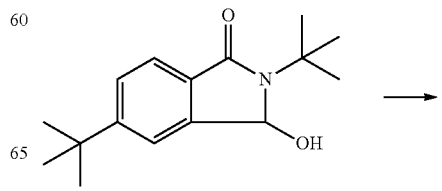

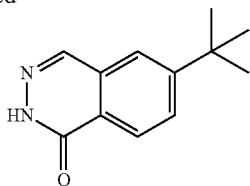

In a 250 mL round-bottomed flask, 2,5-di-tert-butyl-3-hydroxyisoindolin-1-one (4.9 g, 18.7 mmol, Eq: 1.00) was combined with acetic acid (60 ml) to give a colorless solution. The reaction was heated to 90° C. Hydrazine monohydrate (1.61 g, 1.57 ml, 20.6 mmol, Eq: 1.1) was added dropwise. The reaction was stirred at 90° C. for 1 h. The reaction mixture was diluted with 24 mL H$_2$O and slowly cooled to 25° C. over 3 h. The reaction mixture was concentrated but not quite to dryness. The reaction mixture was taken up in dichloromethane. The reaction mixture was poured into 75 mL sat NaHCO$_3$ and extracted with dichloromethane (3×50 mL). The organic layers were dried over Na$_2$SO$_4$ and concentrated in vacuo. to give pure product as a white solid, which was purified by flash chromatography (silica gel, 80 g, 1% to 4% MeOH in DCM) to afford the desired product (3.7 g) as a white solid. (M+H)$^+$=203 m/e. $^1$H NMR (300 MHz, CHLOROFORM-d) δ ppm 0.32 (s, 9 H) 6.58 (d, J=1.89 Hz, 1 H) 6.76 (dd, J=8.31, 1.89 Hz, 1 H) 7.06 (s, 1 H) 7.26 (d, J=8.31 Hz, 1 H) 9.19 (br. s., 1 H).

Step 3. Preparation of 2-(6-tert-Butyl-1-oxo-1H-phthalazin-2-yl)-4-iodo-pyridine-3-carbaldehyde

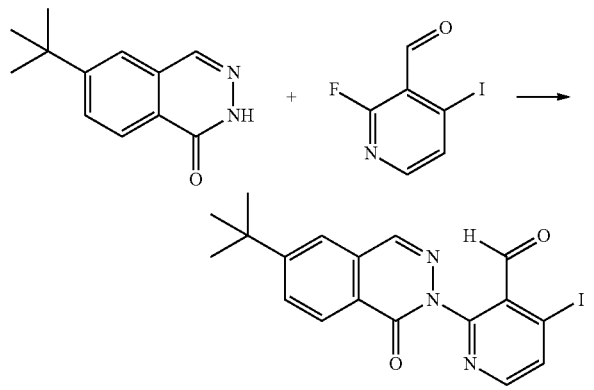

In a 100 mL round-bottomed flask, 6-tert-butylphthalazin-1(2H)-one (700 mg, 3.46 mmol, Eq: 1.00) was combined with THF (30 ml) to give a colorless solution. Sodium hydride (152 mg, 3.81 mmol, Eq: 1.1) was added. The reaction mixture was stirred at ambient temperature for 15 min. A solution of 2-fluoro-4-iodonicotinaldehyde (956 mg, 3.81 mmol, Eq: 1.1) in 10 mL THF was the added to the reaction mixture and it was stirred at ambient temperature for 3.5 h. The reaction was not complete. An additional 50 mg NaH was added. The reaction was stirred for an additional 1.5 h, before addition of saturated NH$_4$Cl. The reaction mixture was poured into 100 mL H$_2$O and extracted with dichloromethane (5×50 mL). The combined organic layers were dried over Na$_2$SO$_4$ and concentrated in vacuo. The crude material was purified by flash chromatography (silica gel, 80 g, 10% to 60% EtOAc in hexanes) to afford slightly impure product. The product was triturated with EtOAc to afford the desired product as a cream solid. The combined filtrate and washes from the trituration were concentrated, re-purified by flash chromatography (silica gel, 80 g, 10% to 60% EtOAc in hexanes) and trituration with EtOAc to afford additional product as a cream solid. The two batches of product were combined to afford 320 mg of the desired product. $^1$H NMR (300 MHz, CHLOROFORM-d) δ ppm 1.44 (s, 9 H) 7.74 (d, J=1.89 Hz, 1 H) 7.89 (dd, J=8.50, 1.70 Hz, 1 H) 8.02 (d, J=5.29 Hz, 1 H) 8.28-8.44 (m, 3 H) 9.92 (s, 1 H) (M+H)$^+$=434 m/e.

Example 7

Preparation of 6-tert-butyl-2-(3-hydroxymethyl-4-{1-methyl-5-[5-(morpholine-4-carbonyl)-pyridin-2-ylamino]-6-oxo-1,6-dihydro-pyridazin-3-yl}-pyridin-2-yl)-2H-phthalazin-1-one

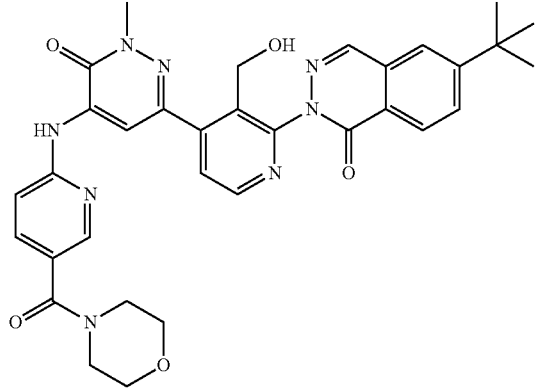 [SMILES: Cn1nc(-c2ccnc(-n3ncc4cc(C(C)(C)C)ccc4c3=O)c2CO)cc(Nc2ccc(C(=O)N3CCOCC3)cn2)c1=O]

Preparation by a similar procedure to example 1 (Step 5-6), except substituting 6-chloro-2-methyl-4-[5-(morpholine-4-carbonyl)-pyridin-2-ylamino]-2H-pyridazin-3-one for 6-chloro-2-methyl-4-(5-(1-methylpiperidin-4-yl)pyridin-2-ylamino)pyridazin-3(2H)-one and substituting 2-(6-tert-Butyl-1-oxo-1H-phthalazin-2-yl)-4-iodo-pyridine-3-carbaldehyde for 2-(6-tert-Butyl-8-fluoro-1-oxophthalazin-2(1H)-yl)-4-iodonicotinaldehyde in step 5 afforded 115 mg of the title compound as a white solid. (M−H)$^+$=621 m/e. $^1$H NMR (400 MHz, CHLOROFORM-d) δ ppm 1.47 (s, 9 H) 3.58-3.87 (m, 6 H) 3.96 (s, 3 H) 4.57 (br. s., 2 H) 7.05 (dd, J=8.53, 0.50 Hz, 1 H) 7.65 (d, J=5.02 Hz, 1 H) 7.80 (td, J=4.27, 2.26 Hz, 2 H) 7.95 (dd, J=8.41, 1.88 Hz, 1 H) 8.41 (s, 1 H) 8.47 (dd, J=5.02, 3.26 Hz, 2 H) 8.50 (s, 1 H) 8.77 (d, J=5.02 Hz, 1 H) 8.81 (s, 1 H).

Example 8

Preparation of 2'-(6-tert-Butyl-8-fluoro-1-oxo-1H-phthalazin-2-yl)-3'-hydroxymethyl-1-methyl-5-[5-(morpholine-4-carbonyl)-pyridin-2-ylamino]-1H-[3,4']bipyridinyl-6-one

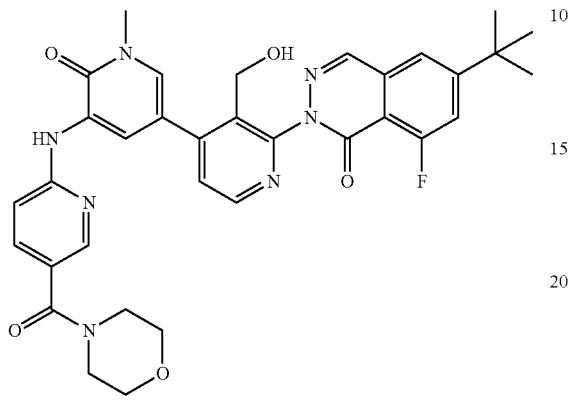

In a 50 mL round-bottomed flask, 2-(6-tert-butyl-8-fluoro-1-oxophthalazin-2(1H)-yl)-4-iodonicotinaldehyde (105 mg, 233 μmol, Eq: 1.00) and 1-methyl-3-(5-(morpholine-4-carbonyl)pyridin-2-ylamino)-5-(4,4,5,5-tetramethyl-1,3,2-dioxaborolan-2-yl)pyridin-2(1H)-one (123 mg, 279 μmol, Eq: 1.20) were combined with dioxane (5 ml) to give a light yellow solution. Water was added (1 mL) and potassium carbonate (74.0 mg, 535 μmol, Eq: 2.3) were added. The reaction was degassed by bubbling argon through the solution for 5 min. Tricyclohexylphosphine (6.53 mg, 23.3 μmol, Eq: 0.1) and bis(dibenzylideneacetone)palladium (6.69 mg, 11.6 μmol, Eq: 0.05) were added. The reaction mixture was heated to 75° C. and stirred for 1 h. The boronic ester consumed with 2-(6-tert-butyl-8-fluoro-1-oxophthalazin-2(1H)-yl)-4-iodonicotinaldehyde still remaining as determined by LCMS analysis. Another 30 mg 1-methyl-3-(5-(morpholine-4-carbonyl)pyridin-2-ylamino)-5-(4,4,5,5-tetramethyl-1,3,2-dioxaborolan-2-yl)pyridin-2(1H)-one and 3 mg ligand and catalyst were added and the reaction mixture was heated to 75° C. and stirred for 1 h.

The reaction mixture was poured into 50 mL H$_2$O and extracted with EtOAc (1×) and DCM with some MeOH (<5%) (3×50 mL). The combined organic layers were dried over MgSO$_4$ and concentrated in vacuo. The crude material was purified by flash chromatography (silica gel, 24 g, 0.5% to 2% MeOH in DCM) to afford 50 mg of 2-(6-tert-butyl-8-fluoro-1-oxophthalazin-2(1H)-yl)-4-(1-methyl-5-(5-(morpholine-4-carbonyl)pyridin-2-ylamino)-6-oxo-1,6-dihydropyridin-3-yl)nicotinaldehyde.

In a 250 mL round-bottomed flask, 2-(6-tert-butyl-8-fluoro-1-oxophthalazin-2(1H)-yl)-4-(1-methyl-5-(5-(morpholine-4-carbonyl)pyridin-2-ylamino)-6-oxo-1,6-dihydropyridin-3-yl)nicotinaldehyde (50 mg, 78.4 μmol, Eq: 1.00) was combined with dichloromethane (6 ml) and 2 mL MeOH to give a yellow solution. Sodium borohydride (3.56 mg, 94.1 μmol, Eq: 1.2) was added. The colorless solution was stirred at ambient temperature for 1 h. 1 mL of saturated NH$_4$Cl was added; followed by 5 mL H$_2$O. Mixture was stirred for 5 min. The reaction mixture was poured into 50 mL H$_2$O and extracted with EtOAc (3×50 mL). The organic layers were dried over Na$_2$SO$_4$ and concentrated in vacuo. The crude material was purified by flash chromatography (silica gel, 24 g, 1% to 3% MeOH in DCM) to afford the desired product (41 mg) as an off-white powder. (M+H)$^+$=640 m/e. $^1$H NMR (400 MHz, CHLOROFORM-d) δ ppm 1.46 (s, 9 H) 3.50-3.85 (s and overlapping m, 11 H) 4.51 (br. s., 2 H) 6.90 (d, J=8.59 Hz, 1 H) 7.51-7.63 (m, 3 H) 7.71 (dd, J=8.59, 2.53 Hz, 1 H) 7.79 (d, J=2.53 Hz, 1 H) 8.26 (br. s., 1 H) 8.37 (d, J=1.52 Hz, 2 H) 8.70 (d, J=5.05 Hz, 1 H) 8.82 (d, J=2.02 Hz, 1 H).

Example 9

Preparation of 2'-(6-tert-Butyl-8-fluoro-1-oxo-1H-phthalazin-2-yl)-3'-hydroxymethyl-5-(5-methanesulfonyl-pyridin-2-ylamino)-1-methyl-1H-[3,4']bipyridinyl-6-one

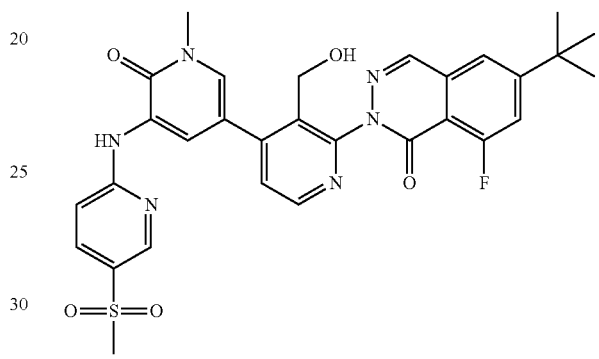

In a 50 mL round-bottomed flask, 2-(6-tert-butyl-8-fluoro-1-oxophthalazin-2(1H)-yl)-4-iodonicotinaldehyde (200 mg, 443 μmol, Eq: 1.00) and 1-methyl-3-(5-(methylsulfonyl)pyridin-2-ylamino)-5-(4,4,5,5-tetramethyl-1,3,2-dioxaborolan-2-yl)pyridin-2(1H)-one$^1$ (234 mg, 576 μmol, Eq: 1.3) were combined in dioxane (5 ml) to give a light yellow solution. Water (1 mL) and potassium carbonate (141 mg, 1.02 mmol, Eq: 2.3) were added. The reaction was degassed by bubbling argon through the solution for 5 min. Tricyclohexylphosphine (12.4 mg, 44.3 μmol, Eq: 0.1) and bis(dibenzylideneacetone)palladium (12.7 mg, 22.2 μmol, Eq: 0.05) were added. The reaction mixture was heated to 70° C. and stirred for 3 h. The resulting reaction mixture was an orange suspension. The reaction mixture was cooled to ambient temperature, diluted with EtOAc and filtered. The resultant solid was washed three times with H$_2$O and three times with small volumes of EtOAc and one time ether to afford 154 mg of 2-(6-tert-butyl-8-fluoro-1-oxophthalazin-2(1H)-yl)-4-(1-methyl-5-(5-(methylsulfonyl)pyridin-2-ylamino)-6-oxo-1,6-dihydropyridin-3-yl)nicotinaldehyde. LCMS showed this to be pure product. (M+H)$^+$=603 m/e.

In a 250 mL round-bottomed flask, 2-(6-tert-butyl-8-fluoro-1-oxophthalazin-2(1H)-yl)-4-(1-methyl-5-(5-(methylsulfonyl)pyridin-2-ylamino)-6-oxo-1,6-dihydropyridin-3-yl)nicotinaldehyde (154 mg, 256 μmol, Eq: 1.00) was combined with dichloromethane (24 ml) and 2 mL MeOH. Sodium borohydride (14.5 mg, 383 μmol, Eq: 1.5) was added and the reaction suspension was stirred at ambient temperature for 1 h. 1 mL of saturated NH$_4$Cl was added; followed by 5 mL H$_2$O. The mixture was stirred for 5 min. The reaction mixture was poured into 50 mL H$_2$O and extracted with dichloromethane (3×50 mL). The organic layers were dried over Na$_2$SO$_4$ and concentrated in vacuo. The crude material was purified by flash chromatography (silica gel, 12 g, 1% to 3% MeOH in DCM) to afford the desired product (90 mg) as a white powder. (M+H)⁺=605 m/e. ¹H NMR (400 MHz, CHLOROFORM-d) δ ppm 1.46 (s, 9 H) 3.10 (s, 3 H) 3.77 (s, 3 H) 4.51 (br. s., 2 H) 6.94 (d, J=8.59 Hz, 1 H) 7.48-7.65 (m, 3 H) 7.88 (d, J=2.53 Hz, 1 H) 8.00 (dd, J=8.59, 2.53 Hz, 1 H) 8.33-8.45 (m, 2 H) 8.71 (d, J=5.05 Hz, 1 H) 8.82 (d, J=2.53 Hz, 1 H) 8.92 (d, J=2.53 Hz, 1 H).

Preparation of I-10

Scheme D

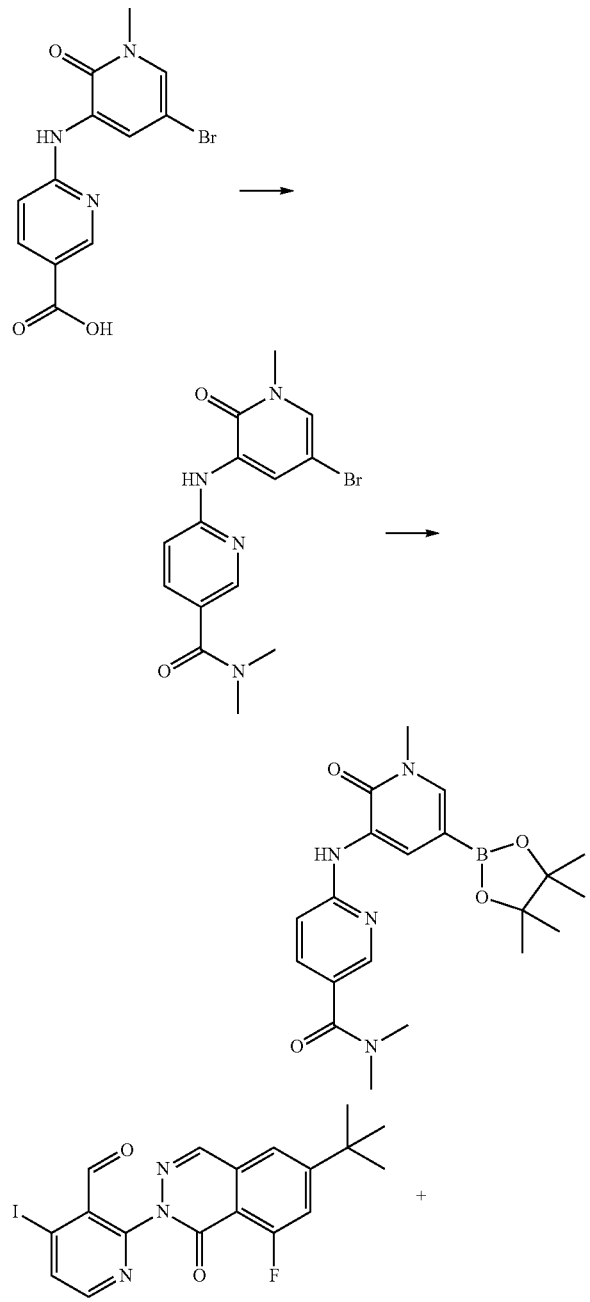

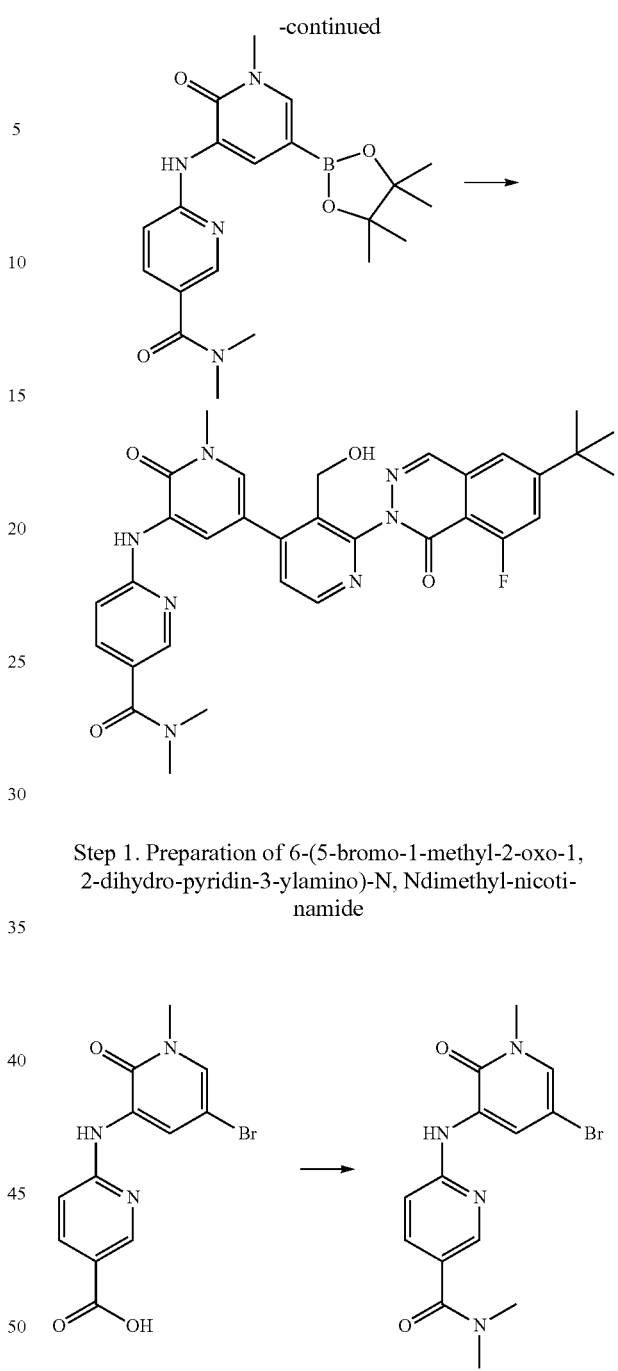

Step 1. Preparation of 6-(5-bromo-1-methyl-2-oxo-1, 2-dihydro-pyridin-3-ylamino)-N, N dimethyl-nicotinamide 6-(5-bromo-1-methyl-2-oxo-1,2-dihydropyridin-3-ylamino)nicotinic acid (prepared from hydrolysis of the methyl ester (3.7 g of 80:20 pure acid: ester, 9.1 mmol, 1 equiv.), DIEA (1.77 g, 13.7 mmol, 1.5 equiv.), dimethylamine (6.85 mL of 2M, 13.7 mmol, 1.5 equiv) and (1H-benzo[d][1, 2,3]triazol-1-yloxy)tris(dimethylamino)phosphonium hexafluorophosphate(V) (6.06 g, 13.7 mmol, 1.5 equiv.) were combined in 200 mL of THF. The reaction mixture was stirred over night, then concentrated to almost dryness. The reaction mixture was diluted with NH₄Cl/water (300 mL) and extracted with EtOAc (3×250 mL). The organic phase was washed with NaHCO₃/water (3×200 mL) and water (3×200 mL). The combined organic phase was then concentrated to give a solid, which was re-crystallized from EtOH/Hex to the desired product (1.7 g). (M+H)⁺=351, 353 m/e. $^1$H NMR (300 MHz, CHLOROFORM-d) δ ppm 3.11 (s, 6 H) 3.61 (s, 3 H) 6.80 (d, J=8.31 Hz, 1 H) 7.03 (d, J=2.27 Hz, 1 H) 7.69 (dd, J=8.69, 2.27 Hz, 1 H) 8.04 (s, 1 H) 8.42 (d, J=2.27 Hz, 1 H) 8.74 (d, J=2.64 Hz, 1 H).

Step 2. Preparation of N,N-dimethyl-6-[1-methyl-2-oxo-5-(4,4,5,5-tetramethyl-[1,3,2]dioxaborolan-2-yl)-1,2-dihydro-pyridin-3-ylamino]-nicotinamide

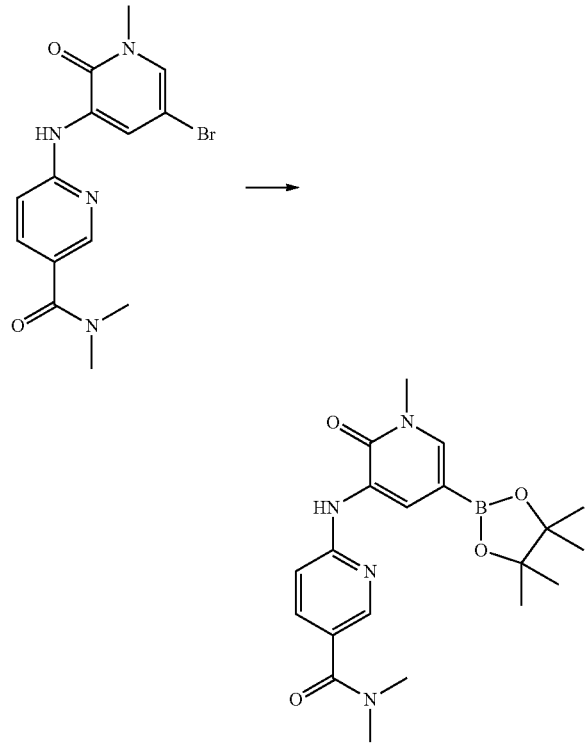

In a 50 mL round bottom flask, 6-(5-bromo-1-methyl-2-oxo-1,2-dihydropyridin-3-ylamino)-N,N-dimethylnicotinamide (1.0 g, 2.85 mmol, Eq: 1.00), and bis(pinacolato)diboron (795 mg, 3.13 mmol, Eq: 1.1) were combined with 1,4-dioxane (10.0 ml) to give a green solution. The reaction mixture was stirred until all dissolved. The mixture was put under argon and then potassium acetate (838 mg, 8.54 mmol, Eq: 3) was added. Palladium(II) acetate (12.8 mg, 56.9 µmol, Eq: 0.02) and X-PHOS (40.7 mg, 85.4 µmol, Eq: 0.03) were added to the reaction mixture. The mixture was placed under an argon atmosphere and the reaction mixture was heated to 75° C. and stirred for 1 h under N₂. The reaction mixture was allowed to cool to 65° C. and then filtered through Celite. The solids were washed with warm dioxanes (10 ml) and cooled to ambient temperature before addition of hexanes (30 ml). The mixture was allowed to sit at ambient temperature for 1 h and then the solid was collected by filtration and washed with hexanes, and dried in vacuum oven at 50° C., over night to afford the desired product (227 mg). $^1$H NMR (400 MHz, CHLOROFORM-d) δ ppm 1.36 (s, 12 H) 3.13 (s, 6 H) 3.66 (s, 3 H) 6.81 (d, J=8.59 Hz, 1 H) 7.43 (d, J=1.52 Hz, 1 H) 7.69 (dd, J=8.59, 2.53 Hz, 1 H) 7.96 (br. s., 1 H) 8.48 (d, J=2.02 Hz, 1 H) 8.67 (d, J=1.52 Hz, 1 H).

Example 10

Preparation of 6-[2'-(6-tert-Butyl-8-fluoro-1-oxo-1H-phthalazin-2-yl)-3'-hydroxymethyl-1-methyl-6-oxo-1,6-dihydro-[3,4']bipyridinyl-5-ylamino]-N,N-dimethyl-nicotinamide

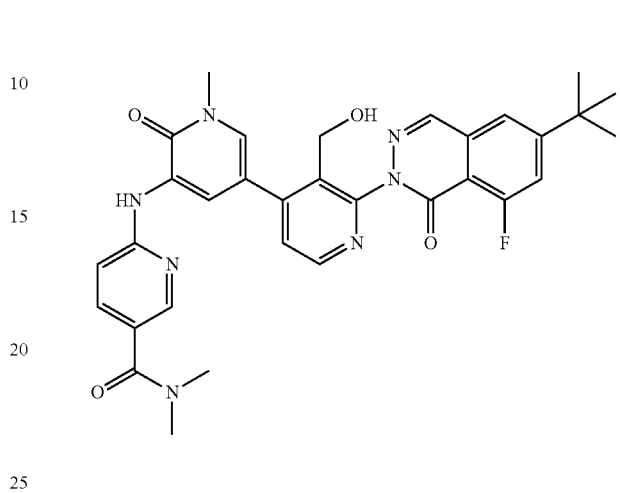

Preparation by a similar procedure to example 8 except substituting N,N-dimethyl-6-[1-methyl-2-oxo-5-(4,4,5,5-tetramethyl-[1,3,2]dioxaborolan-2-yl)-1,2-dihydro-pyridin-3-ylamino]-nicotinamide for 1-methyl-3-(5-(morpholine-4-carbonyl)pyridin-2-ylamino)-5-(4,4,5,5-tetramethyl-1,3,2-dioxaborolan-2-yl)pyridin-2(1H)-one afforded 54 mg of the title compound as an off-white solid. (M+H)⁺=598 m/e. $^1$H NMR (300 MHz, CHLOROFORM-d) δ ppm 1.44 (s, 9 H) 3.11 (s, 6 H) 3.74 (s, 3 H) 4.49 (br. s., 2 H) 6.86 (d, J=8.31 Hz, 1 H) 7.49-7.62 (m, 3 H) 7.70 (dd, J=8.50, 2.45 Hz, 1 H) 7.78 (d, J=2.27 Hz, 1 H) 8.16 (br. s., 1 H) 8.36 (dd, J=8.88, 2.45 Hz, 2 H) 8.68 (d, J=4.91 Hz, 1 H) 8.82 (d, J=2.27 Hz, 1 H).

Example 11

Preparation of 2'-(6-Cyclopropyl-8-fluoro-1-oxo-1H-isoquinolin-2-yl)-3'-hydroxymethyl-1-methyl-5-[5-(morpholine-4-carbonyl)-pyridin-2-ylamino]-1H-[3,4']bipyridinyl-6-one

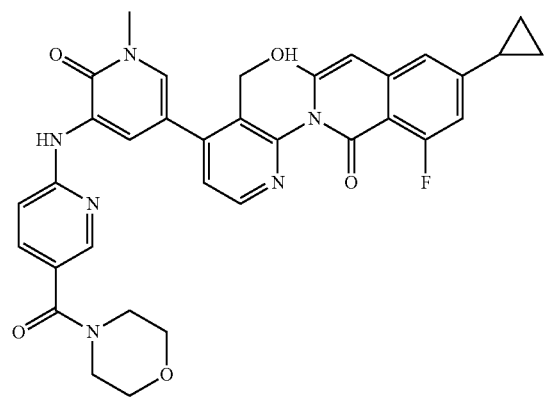

Preparation by a similar procedure to example 8 except substituting 2-(6-cyclopropyl-8-fluoro-1-oxo-1H-isoquinolin-2-yl)-4-iodo-pyridine-3-carbaldehyde for 2-(6-tert-butyl-8-fluoro-1-oxophthalazin-2(1H)-yl)-4-iodonicotinaldehyde afforded 83 mg of the title compound as a white solid. (M+H)⁺=623 m/e. ¹H NMR (300 MHz, CHLOROFORM-d) δ ppm 0.78-0.97 (m, 2 H) 1.09-1.23 (m, 2 H) 1.60 (br. s., 1 H) 1.94-2.10 (m, 1 H) 3.55-3.88 (m and overlapping singlet, 11 H) 4.29-4.62 (m, 2 H) 6.61 (dd, J=7.55, 1.89 Hz, 1 H) 6.79-6.96 (m, 2 H) 7.09 (d, J=1.51 Hz, 1 H) 7.21-7.27 (m, 1 H) 7.53 (d, J=5.29 Hz, 1 H) 7.68 (dd, J=8.69, 2.27 Hz, 1 H) 7.96 (d, J=2.27 Hz, 1 H) 8.26 (br. s., 1 H) 8.35 (d, J=2.27 Hz, 1 H) 8.62 (d, J=4.91 Hz, 1 H) 8.80 (d, J=2.27 Hz, 1 H).

Example 12

Preparation of 6-tert-Butyl-2-(3-hydroxymethyl-4-{1-methyl-5-[5-((S)-1-methyl-pyrrolidin-2-yl)-pyridin-2-ylamino]-6-oxo-1,6-dihydro-pyridazin-3-yl}-pyridin-2-yl)-2H-phthalazin-1-one

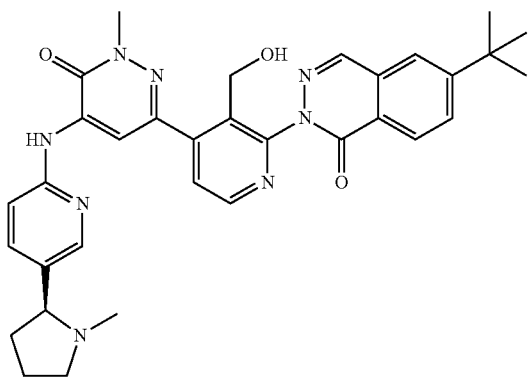 [SMILES: CN1CCC[C@H]1c1ccc(Nc2cc(-c3ccnc(-n4ncc5cc(C(C)(C)C)ccc5c4=O)c3CO)nn(C)c2=O)nc1]

Preparation by a similar procedure to example 1(Step 5-6), except substituting 6-chloro-2-methyl-4-[5-((S)-1-methyl-pyrrolidin-2-yl)-pyridin-2-ylamino]-2H-pyridazin-3-one for 6-chloro-2-methyl-4-(5-(1-methylpiperidin-4-yl)pyridin-2-ylamino)pyridazin-3(2H)-one and substituting 2-(6-tert-Butyl-1-oxo-1H-phthalazin-2-yl)-4-iodo-pyridine-3-carbaldehyde for 2-(6-tert-Butyl-8-fluoro-1-oxophthalazin-2(1H)-yl)-4-iodonicotinaldehyde in step 5 afforded 78 mg of the title compound as a white solid. (M+H)⁺=593 m/e.

¹H NMR (400 MHz, CHLOROFORM-d) δ ppm 1.47 (s, 9H) 1.52-2.49 (m and overlapping singlet, 6 H) 2.99-3.38 (m, 1 H) 3.95 (s, 3 H) 4.01 (t, J=7.03 Hz, 1 H) 4.57 (d, J=6.02 Hz, 2 H) 7.00 (d, J=8.53 Hz, 1 H) 7.66 (d, J=5.02 Hz, 1 H) 7.73 (br. s., 1 H) 7.79 (d, J=1.76 Hz, 1 H) 7.94 (dd, J=8.41, 1.88 Hz, 1 H) 8.26-8.37 (m, 2 H) 8.40 (d, J=0.50 Hz, 1 H) 8.47 (d, J=8.53 Hz, 1 H) 8.72-8.81 (m, 2 H)

Example 13

Preparation of 6-tert-butyl-2-{3-hydroxymethyl-4-[1-methyl-5-(1'-methyl-1',2',3',4',5',6'-hexahydro-[3,4']bipyridinyl-6-ylamino)-6-oxo-1,6-dihydro-pyridazin-3-yl]-pyridin-2-yl}-2H-phthalazin-1-one

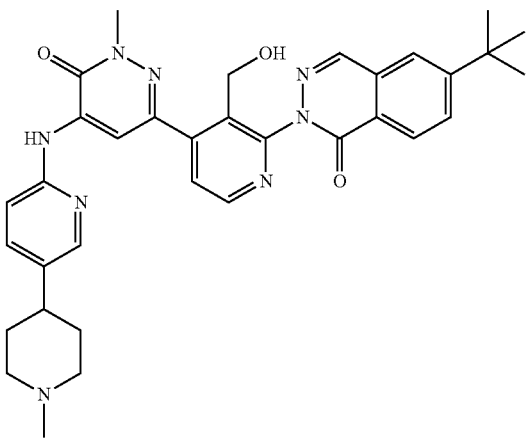 [SMILES: CN1CCC(c2ccc(Nc3cc(-c4ccnc(-n5ncc6cc(C(C)(C)C)ccc6c5=O)c4CO)nn(C)c3=O)nc2)CC1]

Preparation by a similar procedure to example 1(Step 5-6), except substituting 2-(6-tert-Butyl-1-oxo-1H-phthalazin-2-yl)-4-iodo-pyridine-3-carbaldehyde for 2-(6-tert-Butyl-8-fluoro-1-oxophthalazin-2(1H)-yl)-4-iodonicotinaldehyde in step 5 afforded 68 mg of the title compound as a white solid. (M+H)⁺=607 m/e. ¹H NMR (300 MHz, CHLOROFORM-d) δ ppm 1.46 (s, 9 H) 1.75-2.26 (m, 5 H) 2.38 (br. s., 3 H) 2.44-2.61 (m, 1 H) 3.05 (d, J=10.20 Hz, 2 H) 3.93 (s, 3 H) 4.00 (t, J=6.99 Hz, 1 H) 4.55 (d, J=6.42 Hz, 2 H) 6.93 (d, J=8.69 Hz, 1 H) 7.54 (dd, J=8.50, 2.45 Hz, 1 H) 7.64 (d, J=4.91 Hz, 1 H) 7.77 (d, J=1.89 Hz, 1 H) 7.92 (dd, J=8.50, 1.70 Hz, 1 H) 8.20-8.31 (m, 2 H) 8.39 (s, 1 H) 8.45 (d, J=8.31 Hz, 1 H) 8.71 (s, 1 H) 8.74 (d, J=4.91 Hz, 1 H).

Preparation of I-14

Preparation of 6-chloro-4-(1'-ethyl-1',2',3',4',5',6'-hexahydro-[3,4']bipyridinyl-6-ylamino)-2-methyl-2H-pyridazin-3-one

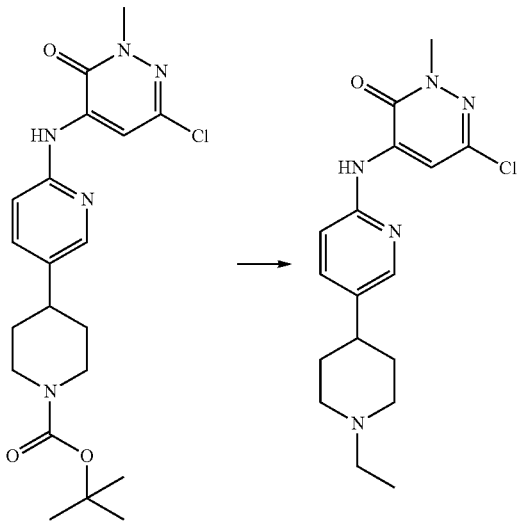 [SMILES: Cn1nc(Cl)cc(Nc2ccc(C3CCN(C(=O)OC(C)(C)C)CC3)cn2)c1=O ; CCN1CCC(c2ccc(Nc3cc(Cl)nn(C)c3=O)nc2)CC1]

In a 250 mL round-bottomed flask, tert-butyl 4-(6-(6-chloro-2-methyl-3-oxo-2,3-dihydropyridazin-4-ylamino)pyridin-3-yl)piperidine-1-carboxylate (620 mg, 1.48 mmol, Eq: 1.00) was combined with dichloromethane (30 ml) to give a yellow solution. TFA (3.37 g, 2.28 ml, 29.5 mmol, Eq: 20) was added. The reaction was stirred at ambient temperature under $N_2$ for 24 h. The reaction mixture was concentrated in vacuo, redissolved in dichloromethane and concentrated in vacuo. The residue was slurried in ether and concentrated in vacuo to afford the TFA salt. (M+H)$^+$=320 m/e. In a 250 mL round-bottomed flask, the resultant TFA salt was combined with DCE (5.0 ml) to give a yellow suspension. 10 mL dichloromethane was added to help most the solid go into solution. Excess acetaldehyde (652 mg, 836 μl, 14.8 mmol, Eq: 10.0) was added. Sodium triacetoxyborohydride (471 mg, 2.22 mmol, Eq: 1.5) was added. The reaction mixture was stirred at ambient temperature for 3 h. Saturated $NaHCO_3$ was added and the reaction mixture was stirred for 5 min, poured onto 10% $NaHCO_3$, extracted five times with dichloromethane. The combined organic extracts were dried over $Na_2SO_4$. The crude material was purified by flash chromatography (silica gel, 24 g, 1% to 6% MeOH in DCM) to afford the desired product (400 mg). (M+H)$^+$=348 m/e. $^1$H NMR (400 MHz, CHLOROFORM-d) δ ppm 1.18 (br. s., 3 H) 1.87 (br. s., 4 H) 2.07 (br. s., 1 H) 2.54 (br. s., 3 H) 3.16 (br. s., 2 H) 3.83 (s, 3 H) 6.88 (d, J=8.34 Hz, 1 H) 7.55 (d, J=8.34 Hz, 1 H) 8.17-8.38 (m, 3 H).

Example 14

Preparation of 6-tert-butyl-2-{4-[5-(1'-ethyl-1',2',3',4',5',6'-hexahydro-[3,4']bipyridinyl-6-ylamino)-1-methyl-6-oxo-1,6-dihydro-pyridazin-3-yl]-3-hydroxymethyl-pyridin-2-yl}-8-fluoro-2H-phthalazin-1-one

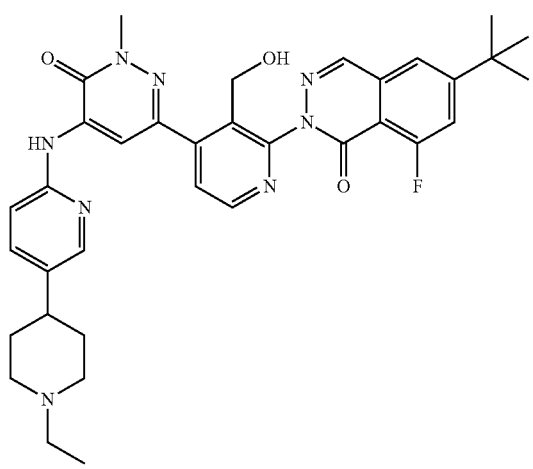 [SMILES: CCN1CCC(c2ccc(Nc3cc(-c4ccnc(-n5ncc6cc(C(C)(C)C)cc(F)c6c5=O)c4CO)nn(C)c3=O)nc2)CC1]

Preparation by a similar procedure to example 1 (Step 5-6), except substituting 6-chloro-4-(1'-ethyl-1',2',3',4',5',6'-hexahydro-[3,4']bipyridinyl-6-ylamino)-2-methyl-2H-pyridazin-3-one for 6-chloro-2-methyl-4-(5-(1-methylpiperidin-4-yl)pyridin-2-ylamino)pyridazin-3(2H)-one in step 5 afforded 61 mg of the title compound as a white solid. (M+H)$^+$=639 m/e. $^1$H NMR (300 MHz, CHLOROFORM-d) δ ppm 1.03-1.24 (m, 3 H) 1.43 (s, 9 H) 1.69-2.20 (m, 6 H) 2.36-2.68 (m, 3 H) 3.12 (d, J=9.82 Hz, 2 H) 3.88 (t, J=7.18 Hz, 1 H) 3.92 (s, 3 H) 4.49-4.63 (m, 2 H) 6.92 (d, J=8.69 Hz, 1 H) 7.46-7.59 (m, 3 H) 7.64 (d, J=5.29 Hz, 1 H) 8.21-8.29 (m, 2 H) 8.32 (d, J=2.27 Hz, 1 H) 8.69 (s, 1 H) 8.73 (d, J=4.91 Hz, 1 H).

Scheme E

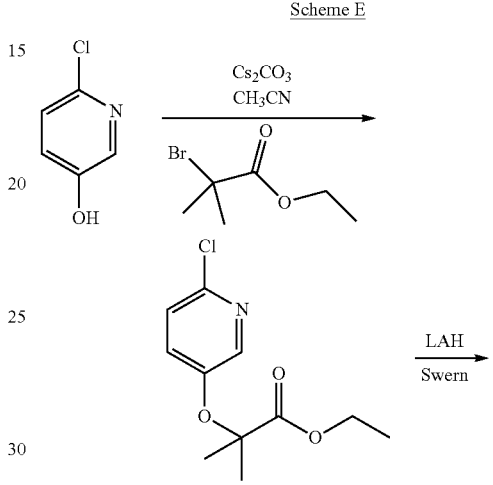

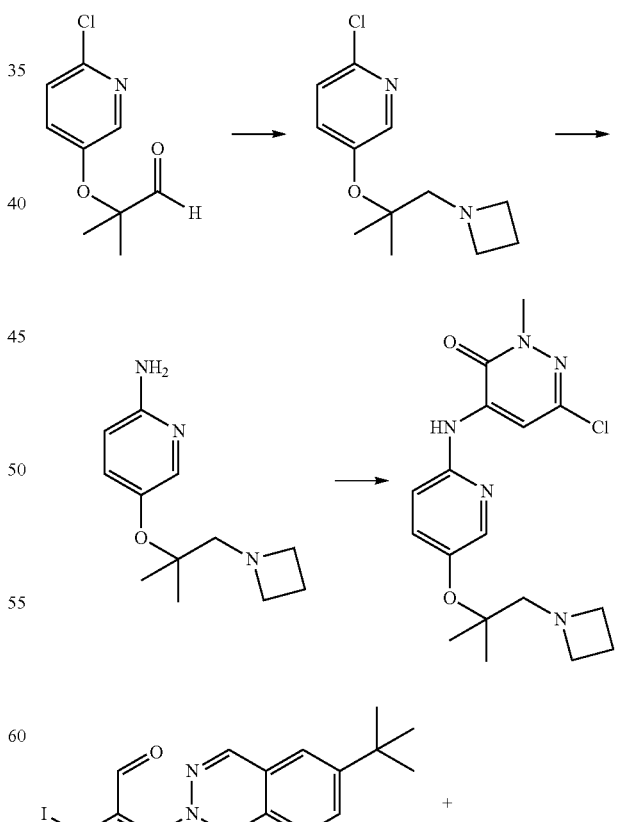

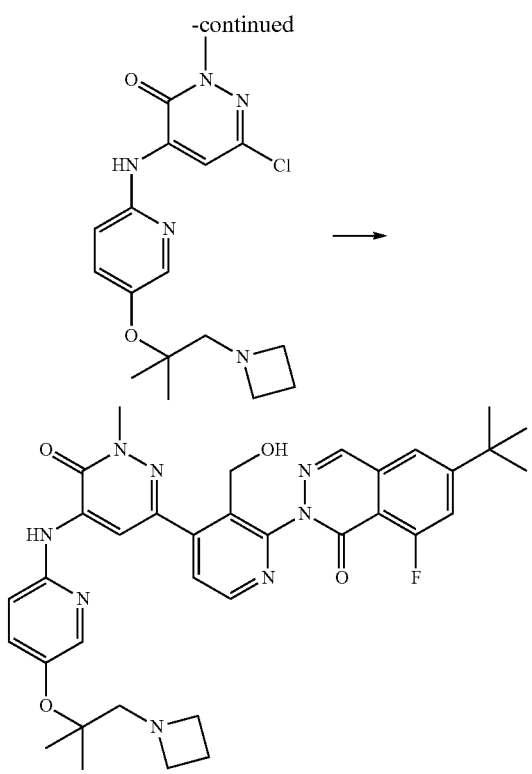

Preparation of I-15

Step 1. Preparation of ethyl 2-(6-chloropyridin-3-yloxy)-2-methylpropanoate

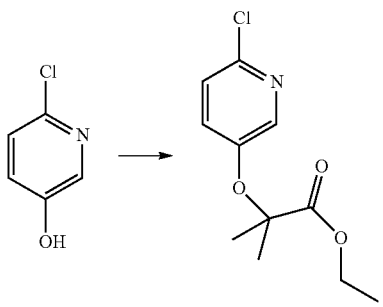 [SMILES: Oc1ccc(Cl)nc1 ; CCOC(=O)C(C)(C)Oc1ccc(Cl)nc1]

To a solution of 6-chloropyridin-3-ol (40 g, 309 mmol, Eq: 1.00) and ethyl 2-bromo-2-methylpropanoate (63.2 g, 48.1 ml, 324 mmol, Eq: 1.05) in 300 ml of $CH_3CN$ was added $Cs_2CO_3$ (216 g, 664 mmol, 309 mmol, Eq: 2.15) and the resulting reaction mixture was stirred under argon atmosphere for 48 h. The reaction mixture was filtered and the filtercake was washed well with EtOAc. The combined filtrate and washes were diluted with water (300 ml) and shaken and the organic phase was collected. The aqueous phase was back-extracted with EtOAc (2×150 ml). The combined organics were dried (MgSO4), filtered and concentrated in vacuo. Purification by passing through a plug of 200 g of silica and elution with 30% EtOAc/Hexanes afforded the desired product (51.1 g) as a light yellow oil. $^1$H NMR (300 MHz, CHLOROFORM-d) δ ppm 1.27 (t, J=7.18 Hz, 3 H) 1.61 (s, 6 H) 4.24 (q, J=7.18 Hz, 2 H) 7.12-7.25 (m, 2 H) 8.01 (d, J=2.64 Hz, 1 H).

Step 2. Preparation of 2-(6-chloropyridin-3-yloxy)-2-methylpropanal

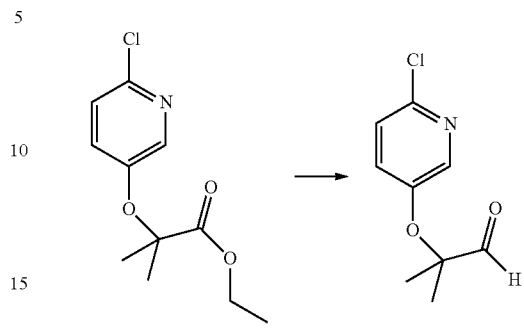

To a solution of ethyl 2-(6-chloropyridin-3-yloxy)-2-methylpropanoate (51.15 g, 210 mmol, Eq: 1.00) in dry THF, cooled to −20 to −30° C. ($CH_3CN/CO_2$) under nitrogen, was added a solution of $LiAlH_4$ (294 mL of 1M in THF, 294 mmol, 1.4 equiv) dropwise over 10 min. The reaction was stirred at −20° C. for 1 h. The reaction was quenched by slow addition of $H_2O$ (6.1 mL) followed by stirring for 10 minutes, 5% NaOH (11.4 ml) followed by stirring for 10 minutes and $H_2O$ (11.4 mL) followed by stirring for 10 minutes. $MgSO_4$ was added to absorb the water and the mixture was filtered filter through a plug of celite. The celite cake was washed well THF (~400 ml).

The solid aluminum salts from filtration were stirred in THF (300 ml) for 10 minutes, filtered and washed well with THF. The combined filtrates and washes were concentrated in vacuo. The resulting residue was dissolved in 150 ml dichloromethane and washed with an equal volume of 50% diluted brine. The aqueous phase was back-extracted (2×100 ml dichloromethane). The combined organic extracts were dried (MgSO4), filtered and concentrated in vacuo to obtain 2-(6-chloro-pyridin-3-yloxy)-2-methyl-propan-1-ol (92% purity, 41.17) g as a light brown oil.

An oven dried flask containing 350 ml dry $CH_2Cl_2$ was cooled to −78° C. under argon. The oxalyl chloride (31.0 g, 20.7 mL, 244 mmol, Eq: 1.30) was added followed by the addition of DMSO (28 mL, 394 mmol, 2.1 equiv) via dropwise addition. The mixture is stirred for 10 minutes and then a solution of 2-(6-chloropyridin-3-yloxy)-2-methylpropan-1-ol (41.17 g of 92% pure material, 188 mmol, Eq: 1.00), dissolved in 60 ml $CH_2Cl_2$, was added via slow dropwise addition. The mixture is stirred for 30 minutes at −78° C. Triethylamine (105 mL, 751 mmol, 4 equiv) was added and the cooling bath was removed and the reaction mixture was allowed to stir for 1 hour with warming to ambient temperature. The reaction mixture was diluted with saturated $NaHCO_3$ (275 mL), shaken and the organic phase collected and washed with an equal volume of brine. The aqueous phase was back-extracted with DCM (2×150 ml). The combined organics phase was dried (MgSO4), filtered and concentrated in vacuo. This resulting residue was purified by Analogix MPLC (SF40-240G column) eluting with 2% to 30% EtOAC/Hex gradient over 60 minutes to afford the desired product (37.1 g) as a light yellow oil. $(M+H)^+$=200 m/e. $^1$H NMR (300 MHz, CHLOROFORM-d) δ ppm 1.44 (s, 6 H) 7.07-7.34 (m, 2 H) 8.05 (d, J=3.02 Hz, 1 H) 9.79 (s, 1 H).

Step 3. Preparation of 5-(2-azetidin-1-yl-1,1-dimethyl-ethoxy)-2-chloro-pyridine

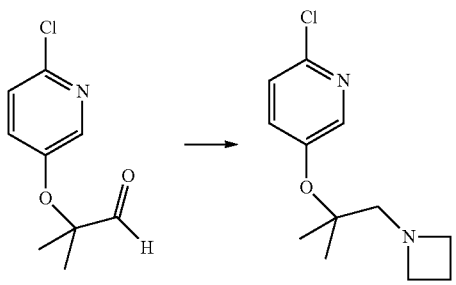 [SMILES: CC(C)(C=O)Oc1ccc(Cl)nc1 ; CC(C)(CN1CCC1)Oc1ccc(Cl)nc1]

In a 100 pressure flask 2-(6-chloropyridin-3-yloxy)-2-methylpropanal (10 g, 50.1 mmol, Eq: 1.00), acetic acid (5.7 mL, 100 mmol) and sodium triacetoxyborohydride (22.3 g, 105 mmol, Eq: 2.1) were dissolved in dichloromethane (58 mL) and cooled to 0° C. To this solution was added azetidine (11.8 mL, 175 mmol, 3.5 equiv) via dropwise addition. The reaction was heated overnight at 55° C., then cooled to ambient temperature. The reaction mixture was diluted with 120 ml saturated NaHCO$_3$ and 80 ml dichloromethane. Mixture was shaken and the dichloromethane layer collected. The organic layer was washed again with 100 ml of 5% NaHCO$_3$ (aq) solution and with an equal volume of 50% diluted brine. The aqueous phase was back-extracted 2×70 ml dichlormethane. The combined organics were dried over Na$_2$SO$_4$, filtered and concentrated in vacuo. The crude product was purified by Analogix MPLC (SF25-60 gram column) eluted with 100% DCM to 5% MeOH/DCM gradient to afford a 70:30 mixture of the desired product: 2-(6-chloro-pyridin-3-yloxy)-2-methyl-propan-1-ol (7.5 g) as a pale yellow oil. Used as is in the next step.

Step 4. Preparation of 5-(1-(azetidin-1-yl)-2-methylpropan-2-yloxy)pyridin-2-amine

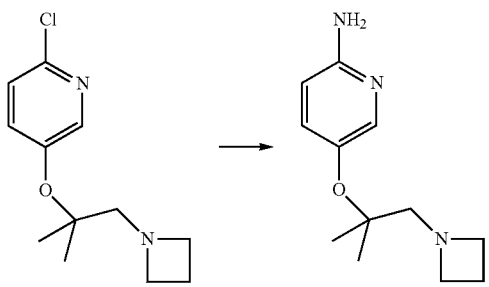 [SMILES: CC(C)(CN1CCC1)Oc1ccc(Cl)nc1 ; CC(C)(CN1CCC1)Oc1ccc(N)nc1]

5-(1-(azetidin-1-yl)-2-methylpropan-2-yloxy)-2-chloropyridine (3.5 g, 14.5 mmol, Eq: 1.00) was dissolved in tetrahydrofuran (78.0 ml). 2-(Dicyclohexylphosphino)biphenyl (1.02 g, 2.91 mmol, Eq: 0.2), then tris(dibenzylideneacetone)dipalladium(0) (1.33 g, 1.45 mmol, Eq: 0.1) were added under an argon atmosphere. Finally 1M lithium bis(trimethylsilyl)amide in THF (43.6 ml, 43.6 mmol, Eq: 3) was added dropwise. The reaction mixture was stirred under argon atmosphere at 75° C. over night. The reaction mixture was poured into 100 ml saturated NH$_4$Cl and extracted with EtOAc (100 ml). The organic phase and washed with 50% diluted brine. The aqueous phase was back extracted with 2×80 ml EtOAc. The combined organic phase was dried (MgSO4), filtered and concentrated in vacuo. The crude material was purified by Analogix MPLC (40 g column (eluted with 1% to 10% MeOH in DCM) to afford the desired product (1.66 g) as a brown viscous oil. $^1$H NMR (300 MHz, CHLOROFORM-d) δ ppm 1.18 (s, 6 H) 2.10 (quin, J=7.08 Hz, 2 H) 2.54 (s, 2 H) 3.33 (t, J=6.99 Hz, 4 H) 4.25 (br. s., 2 H) 6.43 (d, J=8.69 Hz, 1 H) 7.12 (dd, J=8.69, 2.64 Hz, 1 H) 7.79 (d, J=2.64 Hz, 1 H).

Step 5. Preparation of 4-[5-(2-Azetidin-1-yl-1,1-dimethyl-ethoxy)-pyridin-2-ylamino]-6-chloro-2-methyl-2H-pyridazin-3-one

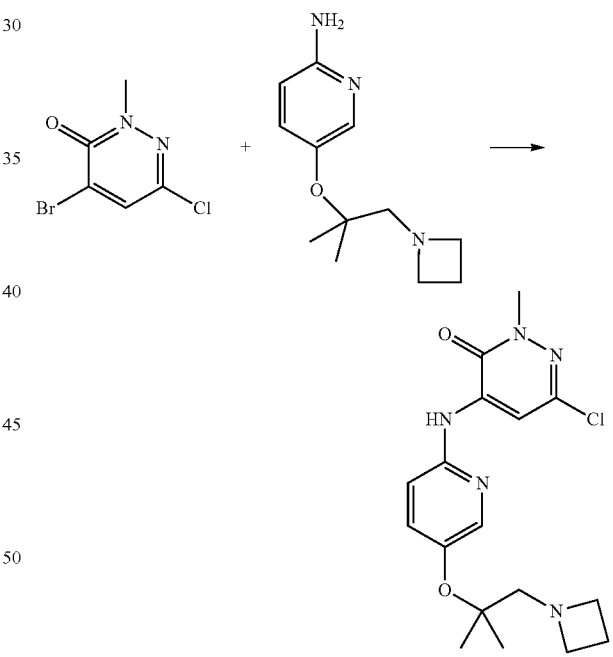

4-Bromo-6-chloro-2-methylpyridazin-3(2H)-one (2.18 g, 9.75 mmol, Eq: 1.30), 5-(1-(azetidin-1-yl)-2-methylpropan-2-yloxy)pyridin-2-amine (1.66 g, 7.5 mmol, Eq: 1.00), Xantphos (651 mg, 1.13 mmol, 0.15 equiv) and Cs2CO3 (8.55 g, 26.3 mmol, 3.5 equiv) were combined in dioxane and the reaction mixture was degassed under vacuum with argon displacement. To the solution was added the Pd2(dba)3 (515 mg, 563 µM, 0.075 equiv) and the mixture was degassed again with argon. The reaction mixture was stirred under argon at 90° C. for 18 hrs before cooling to ambient temperature. The reaction mixture was filtered through a plug of celite. The celite cake was washed with THF and dichloromethane. The combined filtrate and washes were concentrated in vacuo. The crude product was purified by Analogix MPLC (60 g column; elute with 0.5% to 15% MeOH/DCM) to afford the desired product (1.43 g) as a tan solid. (M+H)$^+$=364 m/e. $^1$H NMR (300 MHz, CHLOROFORM-d) δ ppm 1.24 (s, 6 H) 2.12 (quin, J=7.08 Hz, 2 H) 2.59 (s, 2 H) 3.35 (t, J=6.99 Hz, 4 H) 3.81 (s, 3 H) 6.83 (d, J=8.69 Hz, 1 H) 7.32 (dd, J=8.88, 2.83 Hz, 1 H) 8.09 (d, J=3.02 Hz, 1 H) 8.18 (s, 1 H) 8.25 (s, 1 H).

Example 15

Preparation of 2-(4-{5-[5-(2-Azetidin-1-yl-1,1-dimethyl-ethoxy)-pyridin-2-ylamino]-1-methyl-6-oxo-1,6-dihydro-pyridazin-3-yl}-3-hydroxymethyl-pyridin-2-yl)-6-tert-butyl-8-fluoro-2H-phthalazin-1-one

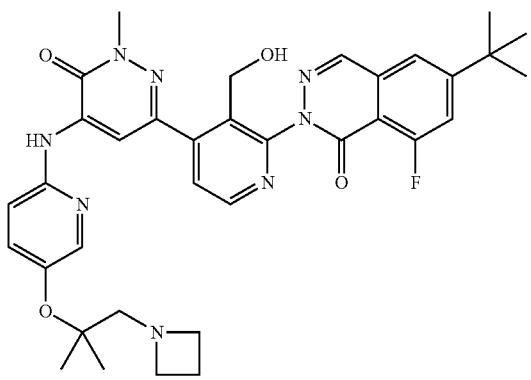 [SMILES: Cn1nc(-c2ccnc(-n3ncc4cc(C(C)(C)C)cc(F)c4c3=O)c2CO)cc(Nc2ccc(OC(C)(C)CN3CCC3)cn2)c1=O]

Preparation by a similar procedure to example 1 (Step 5-6), except substituting 4-[5-(2-azetidin-1-yl-1,1-dimethyl-ethoxy)-pyridin-2-ylamino]-6-chloro-2-methyl-2H-pyridazin-3-one for 6-chloro-2-methyl-4-(5-(1-methylpiperidin-4-yl)pyridin-2-ylamino)pyridazin-3(2H)-one in step 5 afforded 99 mg of the title compound as a white solid. (M+H)$^+$=655 m/e. $^1$H NMR (300 MHz, CHLOROFORM-d) δ ppm 1.25 (s, 6 H) 1.43 (s, 9 H) 2.13 (br. s., 2 H) 2.61 (br. s., 2 H) 3.37 (br. s., 4 H) 3.85 (t, J=6.99 Hz, 1 H) 3.92 (s, 3 H) 4.46-4.63 (m, 2 H) 6.91 (d, J=8.69 Hz, 1 H) 7.34 (dd, J=9.06, 2.64 Hz, 1 H) 7.45-7.58 (m, 2 H) 7.64 (d, J=4.91 Hz, 1 H) 8.09 (d, J=2.64 Hz, 1 H) 8.24-8.37 (m, 2 H) 8.61 (s, 1 H) 8.73 (d, J=4.91 Hz, 1 H).

Example 16

Preparation of 2-(4-{5-[5-(2-Azetidin-1-yl-1,1-dimethyl-ethoxy)-pyridin-2-ylamino]-1-methyl-6-oxo-1,6-dihydro-pyridazin-3-yl}-3-hydroxymethyl-pyridin-2-yl)-6-tert-butyl-2H-phthalazin-1-one

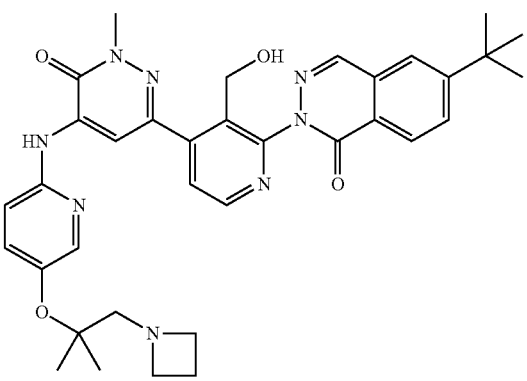 [SMILES: Cn1nc(-c2ccnc(-n3ncc4cc(C(C)(C)C)ccc4c3=O)c2CO)cc(Nc2ccc(OC(C)(C)CN3CCC3)cn2)c1=O]

Preparation by a similar procedure to example 1 (Step 5-6), except substituting 4-[5-(2-azetidin-1-yl-1,1-dimethyl-ethoxy)-pyridin-2-ylamino]-6-chloro-2-methyl-2H-pyridazin-3-one for 6-chloro-2-methyl-4-(5-(1-methylpiperidin-4-yl)pyridin-2-ylamino)pyridazin-3(2H)-one and substituting 2-(6-tert-butyl-1-oxo-1H-phthalazin-2-yl)-4-iodo-pyridine-3-carbaldehyde for 2-(6-tert-butyl-8-fluoro-1-oxophthalazin-2(1H)-yl)-4-iodonicotinaldehyde in step 5 afforded 37 mg of the title compound as a off-white solid. (M+H)$^+$=637 m/e. $^1$H NMR (300 MHz, CHLOROFORM-d) δ ppm 1.27 (br. s., 6 H) 1.46 (s, 9 H) 2.16 (br. s., 2 H) 2.64 (br. s., 2 H) 3.39 (br. s., 4 H) 3.93 (s, 3 H) 3.97 (t, J=7.18 Hz, 1 H) 4.54 (d, J=6.42 Hz, 2 H) 6.91 (d, J=8.69 Hz, 1 H) 7.35 (d, J=7.55 Hz, 1 H) 7.64 (d, J=4.91 Hz, 1 H) 7.77 (d, J=1.51 Hz, 1 H) 7.92 (dd, J=8.50, 1.70 Hz, 1 H) 8.09 (d, J=2.64 Hz, 1 H) 8.28 (s, 1 H) 8.39 (s, 1 H) 8.45 (d, J=8.31 Hz, 1 H) 8.63 (s, 1 H) 8.74 (d, J=4.91 Hz, 1 H).

Preparation of I-17

Scheme F

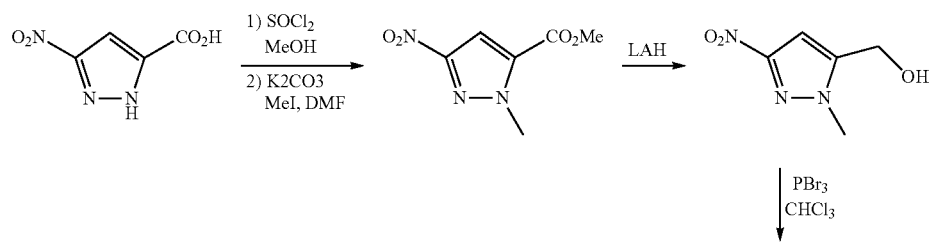

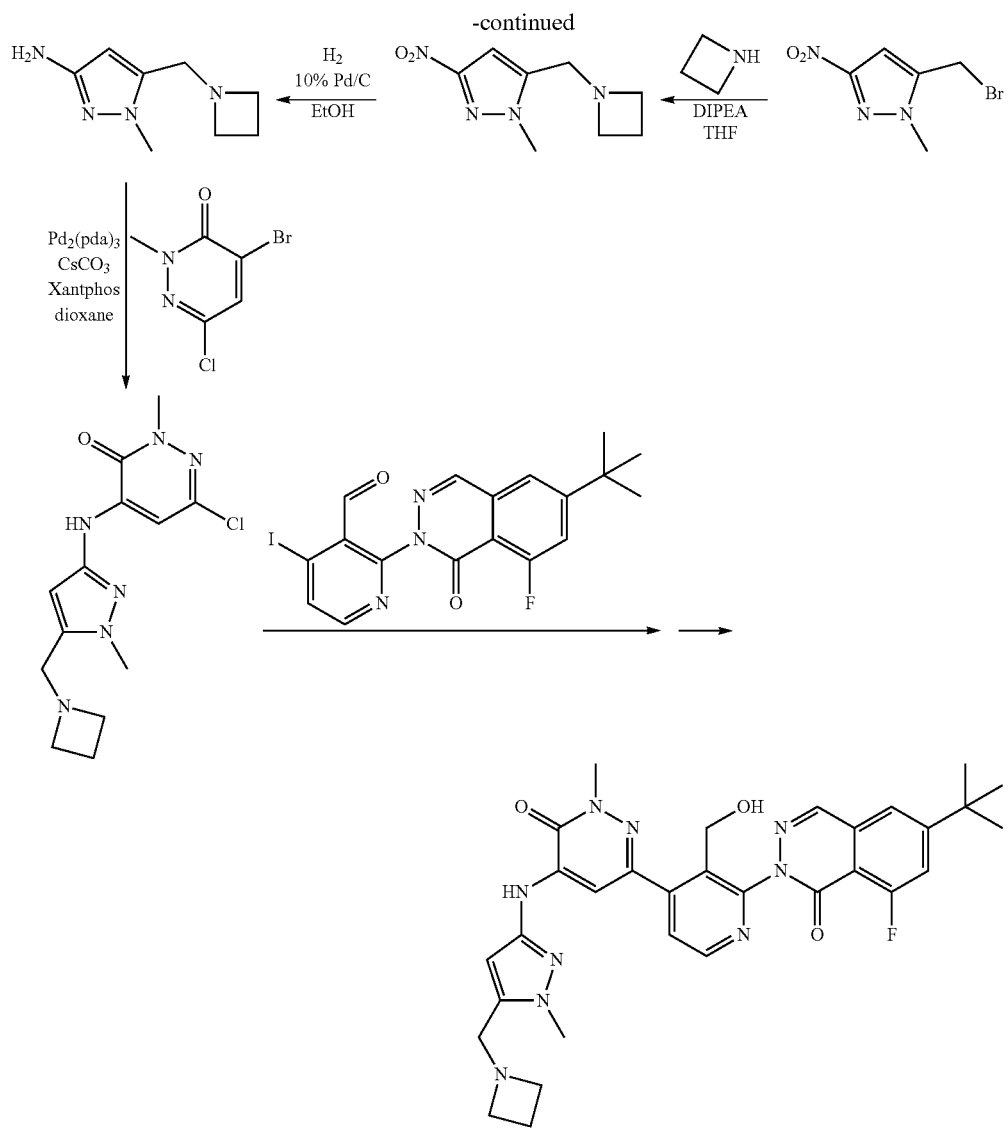

To a solution of 5-nitro-1H-pyrazole-3-carboxylic acid (1.13 g, 7.19 mmol) in anhydrous methanol (20 ml) at to 0° C. was added thionyl chloride (2.23 g, 1.37 ml, 18.7 mmol) dropwise. The resulting solution was heated to reflux for 2 h. The cooled solution was evaporated to dryness to give 5-nitro-2H-pyrazole-3-carboxylic acid methyl ester (1.17 g, 95%) as a white solid.

To a solution of methyl 5-nitro-1H-pyrazole-3-carboxylate (1.87 g, 10.9 mmol) in anhydrous dimethyl formamide (20 mL) was added potassium carbonate (3.02 g, 21.9 mmol) and methyl iodide (2.02 g, 0.89 mL, 14.2 mmol) and the resulting solution stirred at room temperature for 18 h. The resulting mixture was diluted with water (1×150 mL) and extracted with dichloromethane (3×75 mL). The combined organic layers were dried over magnesium sulfate. The mixture was filtered and evaporated and the residue purified by flash chromatography (silica gel, 25 g, 20% to 60% dichloromethane in hexanes) to give a mixture of 2-methyl-5-nitro-2H-pyrazole-3-carboxylic acid methyl ester and 1-methyl-5-nitro-1H-pyrazole-3-carboxylic acid methyl ester (1.64 g, 81%) as a white solid.

To a solution of 2-methyl-5-nitro-2H-pyrazole-3-carboxylic acid methyl ester and 1-methyl-5-nitro-1H-pyrazole-3-carboxylic acid methyl ester (1.18 g, 6.37 mmol) in tetrahydrofuran (20 mL) at 0° C. was added a lithium aluminum hydride solution (1.0M in tetrahydrofuran, 7.65 mL, 7.65 mmol) drop wise. The resulting mixture was stirred at 0° C. for min. To this solution was added ethyl acetate (1 mL) followed by few crystals of sodium sulphate decahydrate. The resulting mixture was stirred for 30 min then filtered, the filter cake washed with ethyl acetate and the filtrate evaporated. The residue was purified by flash chromatography (silica gel, 80 g, 50% to 70% ethyl acetate in hexanes) to give 1-methyl-3-nitro-1H-pyrazol-5-yl)methanol (496 mg, 50%) as a white solid. $^1$H NMR (300 MHz, DMSO-d$_6$) δ ppm 3.90 (s, 3 H) 4.53 (d, J=5.67 Hz, 2 H) 5.55 (t, J=5.48 Hz, 1 H) 6.93 (s, 1 H)

To a solution of (1-methyl-3-nitro-1H-pyrazol-5-yl)methanol (496 mg, 3.16 mmol) in chloroform (10 mL) at 0° C. was added phosphorus tribromide (854 mg, 0.30 mL, 3.16 mmol) drop wise via syringe. The resulting solution was warmed to room temperature and stirred for 1 h. The resulting solution was cooled to 0° C. and diluted with dichloromethane (50 ml). The resulting solution was made basic (pH 8.5) with saturated aqueous sodium bicarbonate (20 mL). The layers were separated, and the aqueous layer was extracted with dichloromethane (3×20 mL). The combined organic layers were dried over magnesium sulfate. The resulting mixture was filtered and concentrated in vacuo and the residue purified by flash chromatography (silica gel, 40 g, 20% to 40% ethyl acetate in hexanes) to give 5-(bromomethyl)-1-methyl-3-nitro-1H-pyrazole (436 mg, 63%) as a white solid. $^1$H NMR (300 MHz, DMSO-$d_6$) δ ppm 3.94 (s, 3 H) 4.85 (s, 2 H) 7.14 (s, 1 H).

To a solution of 5-(bromomethyl)-1-methyl-3-nitro-1H-pyrazole (436 mg, 1.98 mmol) in tetrahydrofuran (10 mL) was added azetidine (141 mg, 0.17 mL, 2.48 mmol) and diisopropylethyl amine (307 mg, 0.42 mL, 2.38 mmol) drop wise and the resulting mixture was stirred at room temperature for 24 h. The solution was concentrated and the residue dissolved in dichloromethane (50 mL), washed with water (50 mL). The aqueous layer was extracted with methylene chloride (2×50 mL) and the organic phases combined and dried over magnesium sulfate. The resulting mixture was filtered and evaporated and the residue purified by flash chromatography (40 g, 1% to 5% methanol in dichloromethane) to give 5-(azetidin-1-ylmethyl)-1-methyl-3-nitro-1H-pyrazole (349 mg, 90%) as a colorless oil. $^1$H NMR (300 MHz, DMSO-$d_6$) δ ppm 1.97 (quin, J=6.99 Hz, 2 H) 3.15 (t, J=6.99 Hz, 4 H) 3.59 (s, 2 H) 3.88 (s, 3 H) 6.89 (s, 1 H).

A solution of 5-(azetidin-1-ylmethyl)-1-methyl-3-nitro-1H-pyrazole (349 mg, 1.78 mmol) in ethanol (20 mL) was treated with palladium on carbon (10%, 50 mg). The resulting mixture was stirred under a hydrogen (1 atm) for 48 h. The reaction mixture was filtered through a celite pad, and the pad washed with ethanol. The filtrate was concentrated in vacuo to give 5-(azetidin-1-ylmethyl)-1-methyl-1H-pyrazol-3-amine (292 mg, 99%) as a light yellow oil. $^1$H NMR (300 MHz, DMSO-$d_6$) δ ppm 1.93 (quin, J=6.89 Hz, 2 H) 3.06 (t, J=6.99 Hz, 4 H) 3.34 (s, 2 H) 3.46 (s, 3 H) 4.36 (s, 2 H) 5.25 (s, 4 H).

A solution of 5-(azetidin-1-ylmethyl)-1-methyl-1H-pyrazol-3-amine (292 mg, 1.76 mmol), 4-bromo-6-chloro-2-methylpyridazin-3(2H)-one (393 mg, 1.76 mmol) cesium carbonate (2.00 g, 6.15 mmol) and 4,5-bis(diphenylphosphino)-9,9-dimethlxanthene (152 mg, 0.26 mmol) in dioxane (10 ml) was flushed with argon before tris(dibenzylideneacetone)dipalladium(0) (121 mg, 0.13 mmol) was added and the resulting solution was heated at 90° C. for 18 h. The mixture was cooled to room temperature and diluted with dichloromethane (50 mL) and water. The layers were separated and the aqueous layer was extracted with dichloromethane (2×25 mL).The organic layers were combined, dried over magnesium sulfate. The resulting mixture was filtered and concentrated in vacuo. The precipitate formed was isolated by filtration, washed with ether and dried under vacuum to give 4-(5-(azetidin-1-ylmethyl)-1-methyl-1H-pyrazol-3-ylamino)-6-chloro-2-methylpyridazin-3(2H)-one (272 mg, 50%) as a light yellow solid. (M+H)$^+$=309 m/e.

$^1$H NMR (300 MHz, DMSO-$d_6$) δ ppm 1.96 (quin, J=6.99 Hz, 2 H) 3.11 (t, J=6.99 Hz, 4 H) 3.31 (s, 2 H) 3.63 (s, 3 H) 3.71 (s, 3 H) 6.07 (s, 1 H) 7.68 (s, 1 H) 9.53 (s, 1 H).

Example 17

Preparation of 2-{4-[5-(5-azetidin-1-ylmethyl-1-methyl-1H-pyrazol-3-ylamino)-1-methyl-6-oxo-1,6-dihydro-pyridazin-3-yl]-3-hydroxymethyl-pyridin-2-yl}-6-tert-butyl-8-fluoro-2H-phthalazin-1-one

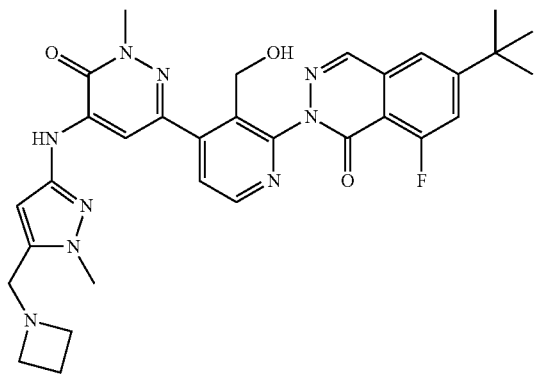 [SMILES: Cn1nc(Nc2cc(-c3ccnc(-n4ncc5cc(C(C)(C)C)cc(F)c5c4=O)c3CO)nn(C)c2=O)cc1CN1CCC1]

Preparation by a similar procedure to example 1 (Step 5-6), except substituting 4-(5-(azetidin-1-ylmethyl)-1-methyl-1H-pyrazol-3-ylamino)-6-chloro-2-methylpyridazin-3(2H)-one for 6-chloro-2-methyl-4-(5-(1-methylpiperidin-4-yl)pyridin-2-ylamino)pyridazin-3(2H)-one in step 5 afforded 70 mg of the title compound as an off-white solid. (M+H)$^+$=600 m/e. $^1$H NMR (300 MHz, CHLOROFORM-d) δ ppm 1.43 (s, 9 H) 2.12 (quin, J=6.99 Hz, 2 H) 3.27 (t, J=6.80 Hz, 4 H) 3.55 (s, 2 H) 3.81 (s, 3 H) 3.90 (s, 3 H) 3.99 (t, J=7.18 Hz, 1 H) 4.54 (d, J=6.04 Hz, 2 H) 5.98 (s, 1 H) 7.42-7.57 (m, 2 H) 7.62 (d, J=4.91 Hz, 1 H) 7.90 (s, 1 H) 7.93 (s, 1 H) 8.31 (d, J=2.64 Hz, 1 H) 8.71 (d, J=5.29 Hz, 1 H).

Preparation of I-18

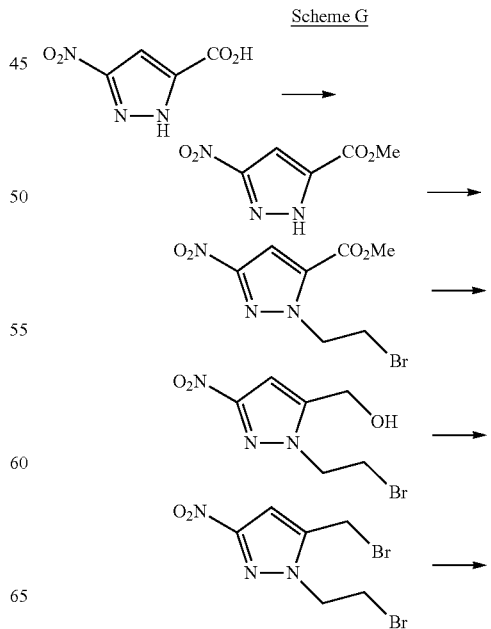

Scheme G

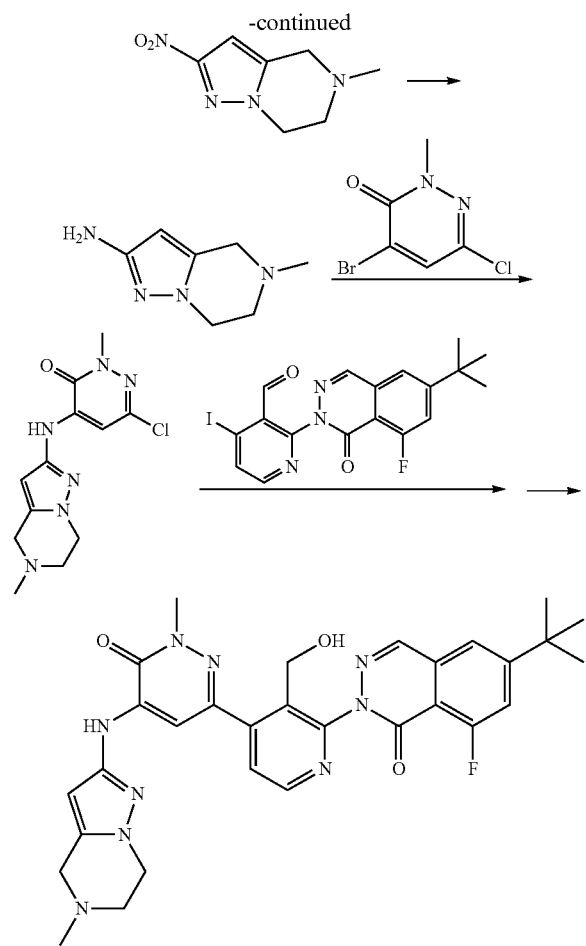

To a solution of methyl 5-nitro-1H-pyrazole-3-carboxylate (5.97 g, 35 mmol) in acetone (100 mL) was added potassium carbonate (24 g, 174 mmol) and 1,2-dibromoethane (19.7 g, 9.02 mL, 105 mmol) and the resulting solution heated to reflux for 2 h. The resulting mixture was allowed to warm to room temperature over night, filtered and concentrated and the residue purified by flash chromatography (silica gel, 400 g, 20% to 70% ethyl acetate in hexanes) to give a 11:2 mixture of methyl 1-(2-bromoethyl)-3-nitro-H-pyrazole-5-carboxylate and 2-(2-Bromo-ethyl)-5-nitro-2H-pyrazole-3-carboxylic acid methyl ester (4.86 g, 50%) as a light yellow solid. Major isomer component $^1$H NMR (300 MHz, DMSO-$d_6$) δ ppm 3.77-4.05 (m, 40 H) 5.02 (t, J=6.04 Hz, 16 H) 7.61 (s, 5.65 H) 7.70 (s, 1 H).

To a suspension of lithium borohydride (755 mg, 34.7 mmol) in tetrahydrofuran (100 mL) at 0° C. was added methyl 1-(2-bromoethyl)-3-nitro-1H-pyrazole-5-carboxylate (4.82 g, 17.3 mmol) in 10 mL of THF slowly. The resulting mixture was allowed to warm to room temperature 2 h. To the resulting mixture was added ethyl acetate (20 ml) and water (20 ml). The biphasic mixture was separated and aqueous layer extracted with ethyl acetate (3×20 mL). The combined organic layers were dried over magnesium sulfate and the resulting mixture was filtered and concentrated in vacuo. to give a crude mixture of 2-(2-Bromo-ethyl)-5-nitro-2H-pyrazol-3-yl]-methanol and (1-(2-bromoethyl)-3-nitro-1H-pyrazol-5-yl)methanol (4.24, 97%) as a light yellow oil, which was used as is in the next reaction To as solution of (1-(2-bromoethyl)-3-nitro-1H-pyrazol-5-yl)methanol (4.24 g, 17 mmol) in chloroform (100 mL), cooled to 0° C., was added phosphorus tribromide (4.59 g, 1.6 mL, 17 mmol) drop wise. The resulting solution was warmed to room temperature and stirred for 2 h. The resulting solution was cooled to 0° C. and diluted with dichloromethane (50 ml). The resulting solution was made basic (pH 8.5) with saturated aqueous sodium bicarbonate was (20 mL). The layers were separated, and the aqueous layer was extracted with dichloromethane (3×50 mL). The combined organic layers were washed with brine (30 mL), dried over magnesium sulfate. The resulting mixture was filtered and concentrated in vacuo. The crude material was purified by flash chromatography (silica gel, SF40-240 g, 15% to 40% EtOAc in hexanes) to give 1-(2-bromoethyl)-5-(bromomethyl)-3-nitro-1H-pyrazole (3.58 g, 67%) as a white solid. $^1$H NMR (300 MHz, DMSO-$d_6$) δ ppm 3.92 (t, J=6.23 Hz, 2 H) 4.69 (t, J=6.23 Hz, 2 H) 4.89 (s, 2 H) 7.19 (s, 1 H).

In a 250 mL round-bottomed flask, 1-(2-bromoethyl)-5-(bromomethyl)-3-nitro-1H-pyrazole (3.58 g, 11.4 mmol, Eq: 1.00) was combined with THF (120 ml) to give a light yellow solution. To this methylamine, 2.0M in THF (40.0 ml, 80.1 mmol, Eq: 7.00) was added dropwise and the reaction mixture was stirred at room temperature for 76 hr. After this time the reaction was concentrated and the resulting solid was stirred with a mixture of EtOAc (50 mL) and 10% aq. K2CO3 (30 mL). The layers were separated and aqueous was back extracted with EtOAc (2×30 mL). The combined organic layers were dried over MgSO$_4$ and concentrated in vacuo to near dryness. The crude material was purified by flash chromatography (silica gel, 240 g, 1% to 10% MeOH in DCM). Fractions that contained product were combined, concentrated and recrystallized from MeOH. Solid was filtered off and washed with ether to afford the desired product (1.6 g) as an off-white solid. $^1$H NMR (300 MHz, DMSO-$d_6$) δ ppm 2.38 (s, 3 H) 2.89 (t, J=5.67 Hz, 2 H) 3.61 (s, 2 H) 4.19 (t, J=5.48 Hz, 2 H) 6.83 (s, 1 H).

A solution of 5-methyl-2-nitro-4,5,6,7-tetrahydro-pyrazolo[1,5-a]pyrazine (1.6 g, 8.7 mmol) in ethanol (20 mL) was treated with palladium on carbon (10%, 300 mg) and flushed with argon. The resulting mixture was stirred under a hydrogen (1 atm) overnight. The reaction mixture was filtered through a celite pad, and the pad washed with ethanol. The filtrate was concentrated in vacuo to give 5-methyl-4,5,6,7-tetrahydropyrazolo[1,5-a]pyrazin-2-amine (1.35 g, quantitative) as a light yellow solid. $^1$H NMR (300 MHz, DMSO-$d_6$) δ ppm 2.30 (s, 3 H) 2.71 (t, J=5.67 Hz, 2 H) 3.37 (s, 2 H) 3.74 (t, J=5.67 Hz, 2 H) 4.46 (s, 2 H) 5.14 (s, 1 H).

A solution of 5-methyl-4,5,6,7-tetrahydropyrazolo[1,5-a]pyrazin-2-amine (342 mg, 2.25 mmol), 4-bromo-6-chloro-2-methylpyridazin-3(2H)-one (527 mg, 2.36 mmol), cesium carbonate (2.2 g, 6.74 mmol) and 4,5-bis(diphenylphosphino)-9,9-dimethlxanthene (195 mg, 0.34 mmol) in dioxane (15 ml) was flushed with argon before tris(dibenzylideneacetone)dipalladium(0) (154 mg, 0.17 mmol) was added and the resulting solution was heated in a sealed tube at 110° C. for 18 h. The mixture was cooled to room temperature and filtered through celite. The cake was washed with dichloromethane. The combined filtrate and washes were diluted with 3M HCl and separated. The DCM layer was back extracted with aqueous HCl and discarded. The combined aqueous HCl extracts were made basic with 3M NaOH. The resulting aqueous phase was extracted 2 times with DCM. The combined DCM extracts were concentrated in vacuo and the resulting solid was triturated with ethyl ether, filtered, and dried to give 6-chloro-2-methyl-4-(5-methyl-4,5,6,7-tetrahydropyrazolo[1,5-a]pyrazin-2-ylamino)pyridazin-3(2H)-one (455 mg, 69%) as an off-white solid. $^1$H NMR (300 MHz, DMSO-d$_6$) δ ppm 2.35 (s, 3 H) 2.81 (t, J=5.48 Hz, 2 H) 3.51 (s, 2 H) 3.63 (s, 3 H) 4.03 (t, J=5.48 Hz, 2 H) 5.98 (s, 1 H) 7.71 (s, 1 H) 9.60 (s, 1 H).

Example 18

Preparation of 6-tert-Butyl-8-fluoro-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-2H-phthalazin-1-one

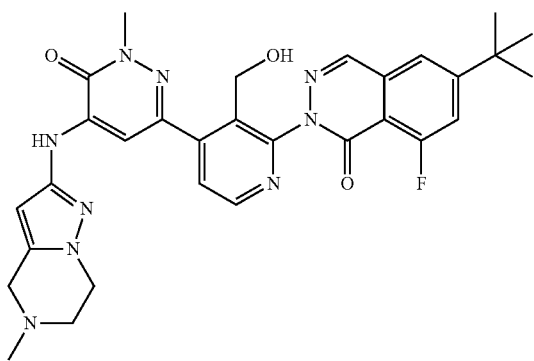

Preparation by a similar procedure to example 1 (Step 5-6), except substituting 6-chloro-2-methyl-4-(5-methyl-4,5,6,7-tetrahydropyrazolo[1,5-a]pyrazin-2-ylamino)pyridazin-3(2H)-one for 6-chloro-2-methyl-4-(5-(1-methylpiperidin-4-yl)pyridin-2-ylamino)pyridazin-3(2H)-one in step 5 afforded 1.02 g of the title compound as an off-white solid. (M+H)$^+$=586 m/e. $^1$H NMR (300 MHz, CHLOROFORM-d) δ ppm 1.43 (s, 9 H) 2.52 (s, 3 H) 2.94 (t, J=5.48 Hz, 2 H) 3.66 (s, 2 H) 3.90 (s, 3 H) 3.97 (t, J=6.99 Hz, 1 H) 4.15 (t, J=5.48 Hz, 2 H) 4.46-4.61 (m, 2 H) 5.84 (s, 1 H) 7.45-7.58 (m, 2 H) 7.62 (d, J=4.91 Hz, 1 H) 7.91 (s, 1 H) 7.97 (s, 1 H) 8.31 (d, J=2.64 Hz, 1 H) 8.71 (d, J=4.91 Hz, 1 H).

Example 19

Preparation of 6-tert-butyl-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-2H-phthalazin-1-one

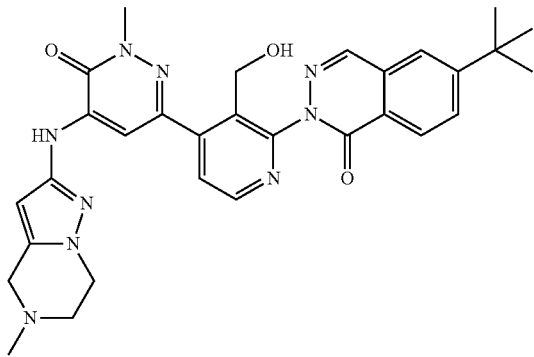 [SMILES: CN1CCn2nc(Nc3cc(-c4ccnc(-n5ncc6cc(C(C)(C)C)ccc6c5=O)c4CO)nn(C)c3=O)cc2C1]

Preparation by a similar procedure to example 1 (Step 5-6), except substituting 6-chloro-2-methyl-4-(5-methyl-4,5,6,7-tetrahydropyrazolo[1,5-a]pyrazin-2-ylamino)pyridazin-3(2H)-one for 6-chloro-2-methyl-4-(5-(1-methylpiperidin-4-yl)pyridin-2-ylamino)pyridazin-3(2H)-one and substituting 2-(6-tert-Butyl-1-oxo-1H-phthalazin-2-yl)-4-iodo-pyridine-3-carbaldehyde for 2-(6-tert-butyl-8-fluoro-1-oxophthalazin-2(1H)-yl)-4-iodonicotinaldehyde in step 5 afforded 72 mg of the title compound as a white solid. (M+H)$^+$=568 m/e. $^1$H NMR (300 MHz, CHLOROFORM-d) δ ppm 1.45 (s, 9 H) 2.54 (s, 3 H) 2.97 (br. s., 2 H) 3.68 (s, 2 H) 3.90 (s, 3 H) 4.08 (t, J=6.99 Hz, 1 H) 4.17 (t, J=5.48 Hz, 2 H) 4.47-4.56 (m, 2 H) 5.86 (s, 1 H) 7.62 (d, J=4.91 Hz, 1 H) 7.77 (d, J=1.89 Hz, 1 H) 7.86-8.01 (m, 3 H) 8.38 (s, 1 H) 8.44 (d, J=8.31 Hz, 1 H) 8.72 (d, J=4.91 Hz, 1 H).

Example 20

Preparation of 6-cyclopropyl-8-fluoro-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-2H-isoquinolin-1-one

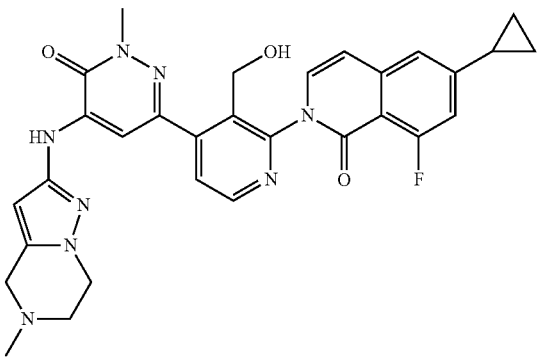 [SMILES: CN1CCn2nc(Nc3cc(-c4ccnc(-n5ccc6cc(C7CC7)cc(F)c6c5=O)c4CO)nn(C)c3=O)cc2C1]

Preparation by a similar procedure to example 1 (Step 5-6), except substituting 6-chloro-2-methyl-4-(5-methyl-4,5,6,7-tetrahydropyrazolo[1,5-a]pyrazin-2-ylamino)pyridazin-3(2H)-one for 6-chloro-2-methyl-4-(5-(1-methylpiperidin-4-yl)pyridin-2-ylamino)pyridazin-3(2H)-one and substituting 2-(6-cyclopropyl-8-fluoro-1-oxo-1H-isoquinolin-2-yl)-4-iodo-pyridine-3-carbaldehyde for 2-(6-tert-butyl-8-fluoro-1-oxophthalazin-2(1H)-yl)-4-iodonicotinaldehyde in step 5 afforded 33 mg of the title compound as an off-white solid. (M+H)$^+$=569 m/e. $^1$H NMR (400 MHz, CHLOROFORM-d) δ ppm 0.81-0.93 (m, 2 H) 1.07-1.22 (m, 2 H) 1.95-2.09 (m, 1 H) 2.54 (s, 3 H) 2.96 (br. s., 2 H) 3.68 (br. s., 2 H) 3.92 (s, 3 H) 4.17 (t, J=5.43 Hz, 2 H) 4.24 (dd, J=10.48, 2.91 Hz, 1 H) 4.45-4.64 (m, 2 H) 5.91 (s, 1 H) 6.57 (dd, J=7.58, 2.02 Hz, 1 H) 6.83 (dd, J=12.63, 1.52 Hz, 1 H) 7.08 (d, J=1.52 Hz, 1 H) 7.26 (d, J=7.33 Hz, 2 H) 7.62 (d, J=5.05 Hz, 1 H) 7.93 (s, 1 H) 8.01 (s, 1 H) 8.68 (d, J=5.05 Hz, 1 H).

Preparation of I-21

Step 1. Preparation of 2-nitro-5-oxetan-3-yl-4,5,6,7-tetrahydro-pyrazolo[1,5-a]pyrazine

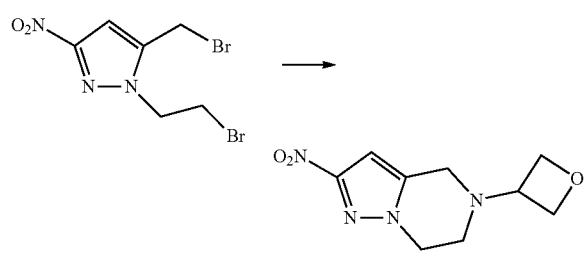

In a 250 mL round-bottomed flask, 1-(2-bromoethyl)-5-(bromomethyl)-3-nitro-1H-pyrazole (1.54 g, 4.92 mmol, Eq: 1.00) was combined with $CH_3CN$ (60 ml) to give a light yellow solution. To this oxetan-3-amine (432 mg, 5.91 mmol, Eq: 1.20) and dropwise DIPEA (1.14 g, 1.55 ml, 8.86 mmol, Eq: 1.80) were added and the reaction mixture was stirred at room temperature for 24 hr.

The mixture was concentrated and the residue was taken up in EtOAc (50 mL) and washed with water (50 mL). The organic layer was dried over $MgSO_4$ and concentrated in vacuo. The crude material was purified by flash chromatography (silica gel, SF25-40 g, 50% EtOAc in Hexanes to 100% EtOAc) to afford the desired product (674 mg). $^1$H NMR (400 MHz, CHLOROFORM-d) δ ppm 2.94-3.01 (m, 2 H) 3.71 (s, 2 H) 3.87 (quin, J=6.32 Hz, 1 H) 4.31-4.39 (m, 2 H) 4.67-4.75 (m, 2 H) 4.77-4.84 (m, 2 H) 6.68 (s, 6 H).

Step 2. Preparation of 5-oxetan-3-yl-4,5,6,7-tetrahydro-pyrazolo[1,5-a]pyrazin-2-ylamine

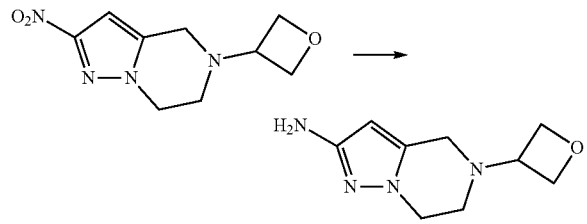

In a 250 mL round-bottomed flask, 2-nitro-5-oxetan-3-yl-4,5,6,7-tetrahydro-pyrazolo[1,5-a]pyrazine (674 mg, 2.99 mmol, Eq: 1.00) was combined with EtOH (50 ml) to give a light yellow suspension. The reaction mixture was vacuum flushed three times with argon then 10% Pd/C (159 mg, 1.5 mmol, Eq: 0.5) was added and the reaction mixture was stirred under hydrogen balloon overnight. The reaction was filtered through a pad of celite. The celite pad was washed with ethanol. The combined filtrate and washes were concentrated in vacuo to afford the desired product (555 mg). $(M+H)^+=195$ m/e.

Step 3. Preparation of 6-chloro-2-methyl-4-(5-oxetan-3-yl-4,5,6,7-tetrahydro-pyrazolo[1,5-a]-pyrazin-2-ylamino)-2H-pyridazin-3-one

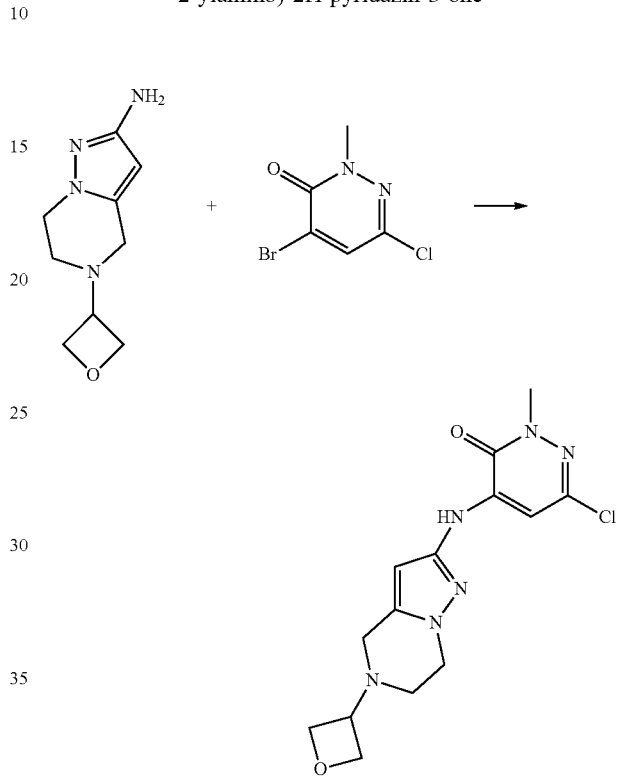

In a 250 mL round-bottomed flask, 5-(oxetan-3-yl)-4,5,6,7-tetrahydropyrazolo[1,5-a]pyrazin-2-amine (555 mg, 2.86 mmol, Eq: 1.00), 4-bromo-6-chloro-2-methylpyridazin-3(2H)-one (638 mg, 2.86 mmol, Eq: 1.00) cesium carbonate (3.26 g, 10.0 mmol, Eq: 3.50) and 4,5-bis(diphenylphosphino)-9,9-dimethylxanthene (248 mg, 429 µmol, Eq: 0.15) were combined with dioxane (40 ml) and the reaction mixture was vacuum flushed 3× with argon. Bis(dibenzylideneacetone)palladium (123 mg, 214 µmol, Eq: 0.075) was added and the reaction was heated at 90° C. for 18 hr. After cooling to room temperature it was diluted with 50 mL dichloromethane and water. The aqueous layer was back-extracted with DCM (2×25 mL). The combined organic layers were dried over $MgSO_4$ and concentrated in vacuo to near dryness. The resulting solid was collected by filtration and washed with ethyl ether. A second crop of solid that formed in the filtrate and washes was collected by filtration and washed with ethyl ether. The combined solids were dried under vacuum to afford the desired product (669 mg) as a solid. $(M+H)^+=337$ m/e. $^1$H NMR (400 MHz, CHLOROFORM-d) δ ppm 3.01 (t, J=5.18 Hz, 2 H) 3.73 (s, 2 H) 3.81 (s, 3 H) 3.92 (t, J=6.44 Hz, 1 H) 4.26 (t, J=5.43 Hz, 2 H) 4.79 (d, J=6.57 Hz, 4 H) 5.77 (s, 1 H) 7.60 (s, 1 H) 7.88 (s, 1 H).

Example 21

Preparation of 6-tert-butyl-8-fluoro-2-{3-hydroxymethyl-4-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-pyridin-2-yl}-2H-phthalazin-1-one

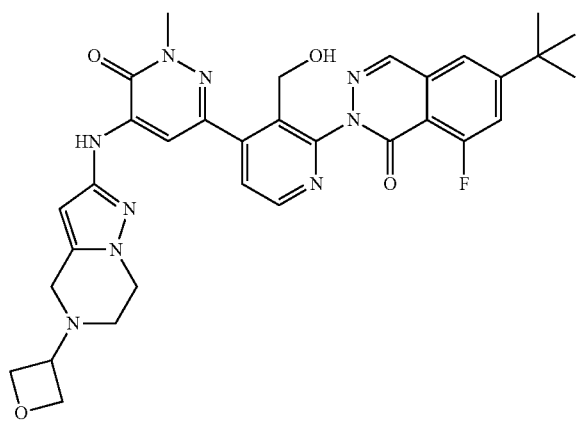

Preparation by a similar procedure to example 1 (Step 5-6), except substituting 6-chloro-2-methyl-4-(5-oxetan-3-yl-4,5,6,7-tetrahydro-pyrazolo[1,5-a]-pyrazin-2-ylamino)-2H-pyridazin-3-one for 6-chloro-2-methyl-4-(5-(1-methylpiperidin-4-yl)pyridin-2-ylamino)pyridazin-3(2H)-one in step 5 afforded 106 mg of the title compound as a white solid. (M+H)$^+$=628 m/e. $^1$H NMR (300 MHz, CHLOROFORM-d) δ ppm 1.44 (s, 9 H) 2.91 (t, J=5.48 Hz, 2 H) 3.65 (s, 2 H) 3.83 (t, J=6.23 Hz, 1 H) 3.91 (s, 3 H) 4.18 (t, J=5.48 Hz, 2 H) 4.54 (s, 2 H) 4.75 (quin, J=6.52 Hz, 4 H) 5.89 (s, 1 H) 7.47-7.58 (m, 2 H) 7.62 (d, J=5.29 Hz, 1 H) 7.91 (s, 1 H) 7.98 (s, 1 H) 8.32 (d, J=2.64 Hz, 1 H) 8.71 (d, J=4.91 Hz, 1 H).

Preparation of I-22

Step 1. Preparation of 5-ethyl-2-nitro-4,5,6,7-tetrahydro-pyrazolo[1,5-a]pyrazine

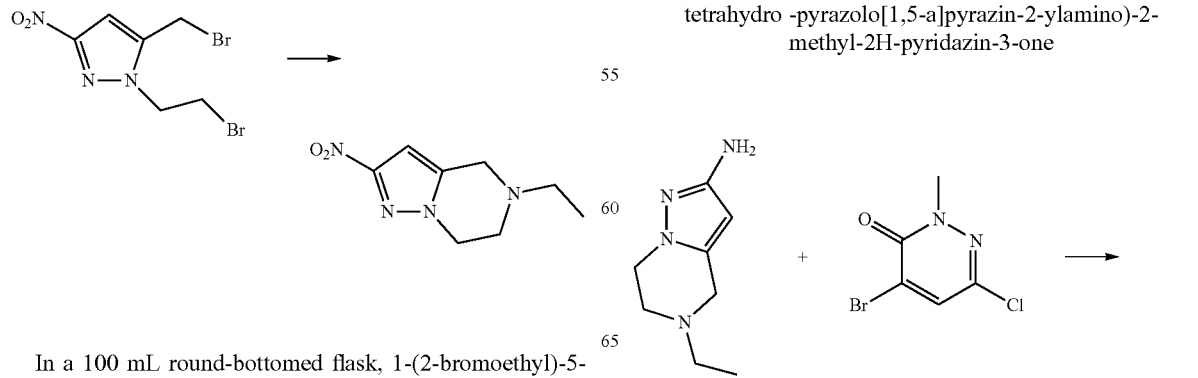

In a 100 mL round-bottomed flask, 1-(2-bromoethyl)-5-(bromomethyl)-3-nitro-1H-pyrazole (0.7 g, 2.24 mmol, Eq: 1.00) was combined with THF (25 ml) to give a light yellow solution. To this ethylamine (7.83 ml of 2M in THF, 15.7 mmol, Eq: 7) was added dropwise and the reaction mixture was stirred at ambient temperature for 12 hr. The reaction mixture was concentrated and the resulting solid was stirred with a mixture of EtOAc (250 mL) and 10% aqueous K$_2$CO$_3$ (200 mL). The layers were separated and aqueous layer was back extracted with EtOAc (2×100 mL). The combined organic layers were dried over MgSO$_4$ and concentrated in vacuo. The crude material was purified by flash chromatography (silica gel, 40 g, 1% to 4% MeOH in DCM). Fractions containing product were combined and concentrated to afford the desired product (427 mg). $^1$H NMR (300 MHz, CHLOROFORM-d) δ ppm 1.20 (t, J=7.18 Hz, 3 H) 2.68 (q, J=7.18 Hz, 2 H) 3.01 (t, J=5.48 Hz, 2 H) 3.72 (s, 2 H) 4.29 (t, J=5.67 Hz, 2 H) 6.64 (s, 1 H).

Step 2. Preparation of 5-ethyl-4,5,6,7-tetrahydro-pyrazolo[1,5-a]pyrazin-2-ylamine

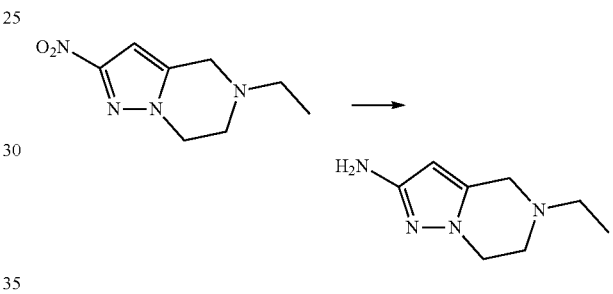

In a 250 mL round-bottomed flask, 5-ethyl-2-nitro-4,5,6,7-tetrahydro-pyrazolo[1,5-a]pyrazine (427 mg, 2.17 mmol, Eq: 1.00) was combined with EtOH (50 ml) to give a light yellow suspension. The reaction mixture was vacuum flushed three times with argon then 10% Pd/C (115 mg, 1.08 mmol, Eq: 0.5) was added and the reaction mixture was stirred under hydrogen balloon overnight. The reaction was filtered through a pad of celite. The celite pad was washed with ethanol. The combined filtrate and washes were concentrated in vacuo to afford the desired product (350 mg). (M+H)$^+$=167 m/e. $^1$H NMR (300 MHz, CHLOROFORM-d) δ ppm 1.16 (t, J=7.18 Hz, 3 H) 2.59 (q, J=7.18 Hz, 2 H) 2.79-3.03 (m, 2 H) 3.57 (overlapping s, 4 H) 3.87-4.12 (m, 2 H) 5.35 (s, 1 H).

Step 3. Preparation of 6-chloro-4-(5-ethyl-4,5,6,7-tetrahydro-pyrazolo[1,5-a]pyrazin-2-ylamino)-2-methyl-2H-pyridazin-3-one

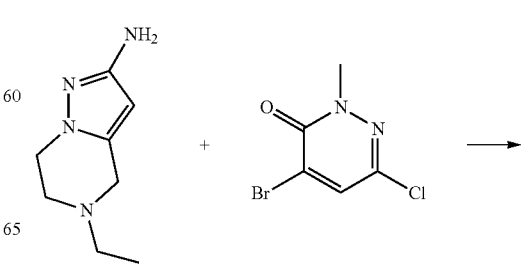

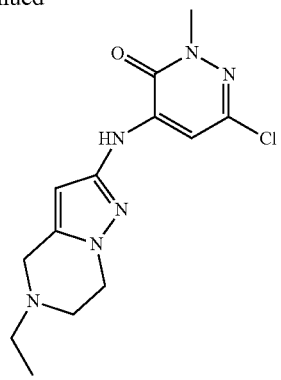

In a 250 mL round-bottomed flask, 5-ethyl-4,5,6,7-tetrahydropyrazolo[1,5-a]pyrazin-2-amine (350 mg, 2.11 mmol, Eq: 1.00), 4-bromo-6-chloro-2-methylpyridazin-3(2H)-one (471 mg, 2.11 mmol, Eq: 1.00), cesium carbonate (2.4 g, 7.37 mmol, Eq: 3.50) and 4,5-bis(diphenylphosphino)-9,9-dimethylxanthene (183 mg, 316 µmol, Eq: 0.15) were combined with dioxane (40 ml) and the reaction mixture was flushed with argon. Then bis(dibenzylideneacetone)palladium (90.8 mg, 158 µmol, Eq: 0.075) was added and the reaction mixture was heated at 90° C. for 18 hr. After cooling to room temperature it was diluted with 50 mL dichloromethane and water. The aqueous layer was back-extracted with DCM (2×25 mL). The combined organic layers were dried over MgSO$_4$ and concentrated in vacuo. The crude material was purified by flash chromatography (silica gel, 40 g, 0% to 3% MeOH in DCM). The pure fractions were triturated with EtOAc. Mixed fractions and filtrate were purified by chromatography to afford pure product, which was combined with the triturated solid to afford the desired product (500 mg). (M+H)$^+$=309 m/e.

$^1$H NMR (300 MHz, CHLOROFORM-d) δ ppm 1.21 (t, J=7.18 Hz, 3 H) 2.67 (d, J=6.80 Hz, 2 H) 2.99 (br. s., 2 H) 3.69 (br. s., 2 H) 3.79 (s, 3 H) 4.16 (d, J=5.29 Hz, 2 H) 5.72 (s, 1 H) 7.56 (s, 1 H) 7.85 (s, 1 H).

Example 22

Preparation of 6-tert-butyl-2-{4-[5-(5-ethyl-4,5,6,7-tetrahydro-pyrazolo[1,5-a]pyrazin-2-ylamino)-1-methyl-6-oxo-1,6-dihydro-pyridazin-3-yl]-3-hydroxymethyl-pyridin-2-yl}-8-fluoro-2H-phthalazin-1-one

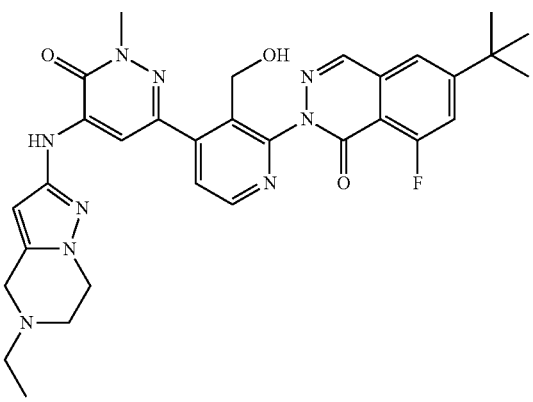 [SMILES: CCN1CCn2nc(Nc3cc(-c4ccnc(-n5ncc6cc(C(C)(C)C)cc(F)c6c5=O)c4CO)nn(C)c3=O)cc2C1]

Preparation by a similar procedure to example 1 (Step 5-6), except substituting 6-chloro-4-(5-ethyl-4,5,6,7-tetrahydro-pyrazolo[1,5-a]pyrazin-2-ylamino)-2-methyl-2H-pyridazin-3-one for 6-chloro-2-methyl-4-(5-(1-methylpiperidin-4-yl)pyridin-2-ylamino)pyridazin-3(2H)-one in step 5 afforded 196 mg of the title compound as an off-white solid. (M+H)$^+$=600 m/e.

$^1$H NMR (300 MHz, CHLOROFORM-d) δ ppm 1.21 (td, J=6.99, 2.27 Hz, 3 H) 1.43 (s, 9 H) 2.66 (d, J=6.80 Hz, 2 H) 2.98 (br. s., 2 H) 3.69 (br. s., 2 H) 3.90 (s, 3 H) 3.97 (t, J=6.99 Hz, 1 H) 4.15 (t, J=4.53 Hz, 2 H) 4.47-4.60 (m, 2 H) 5.85 (s, 1 H) 7.46-7.57 (m, 2 H) 7.62 (d, J=4.91 Hz, 1 H) 7.89 (s, 1 H) 7.97 (s, 1 H) 8.31 (d, J=2.64 Hz, 1 H) 8.71 (d, J=4.91 Hz, 1 H).

Preparation of I-23

Scheme H

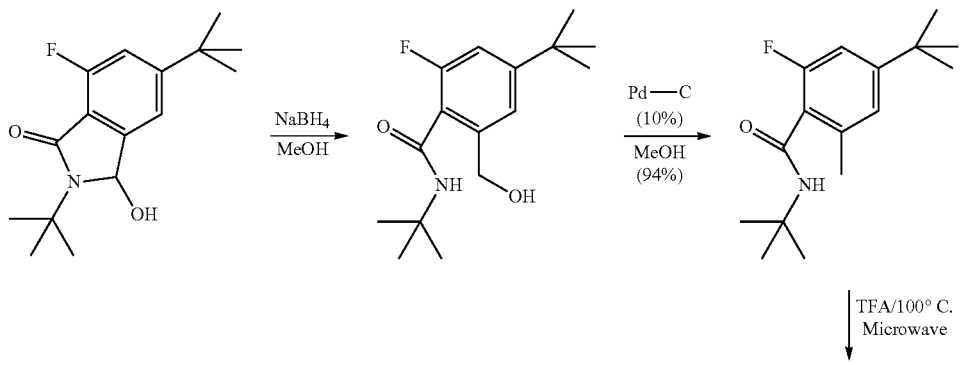

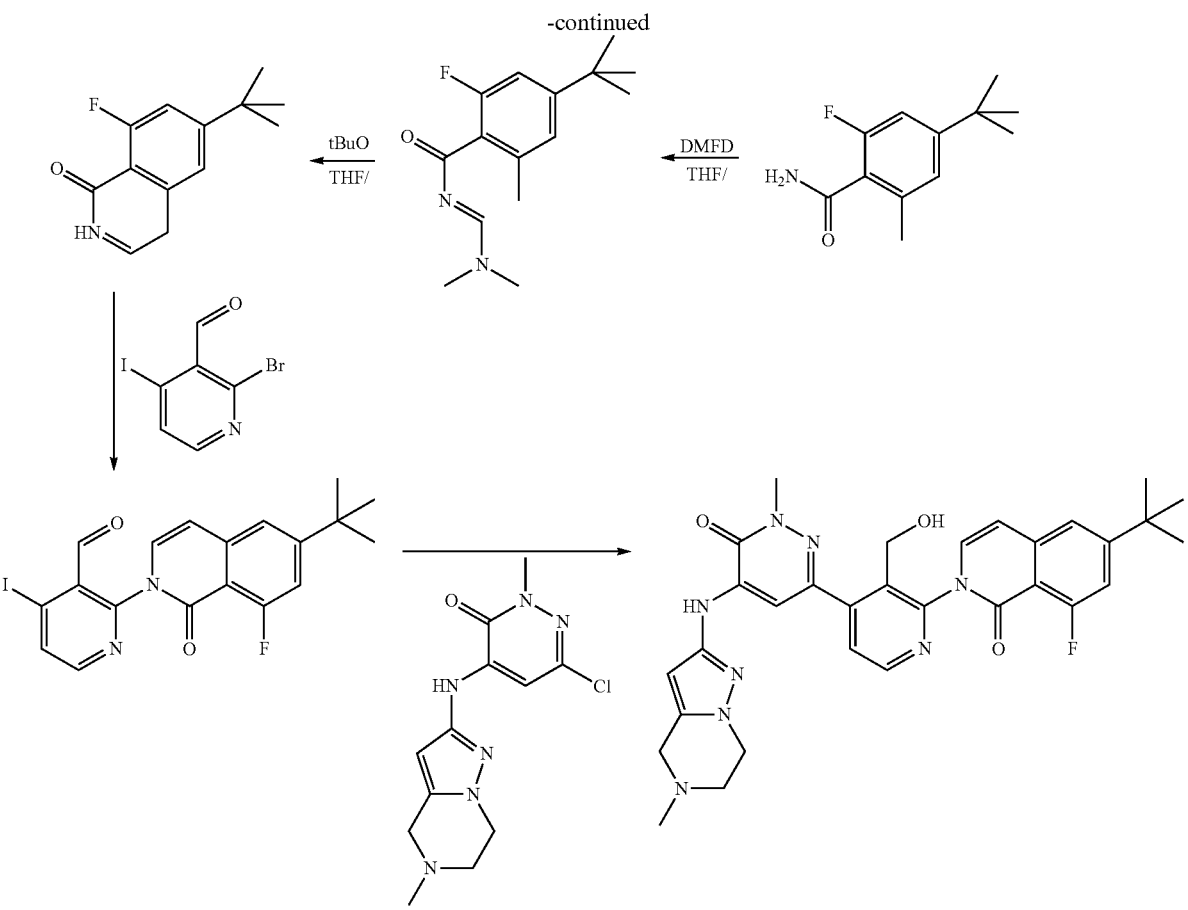

Step 1. Preparation of 4,N-Di-tert-butyl-2-fluoro-6-hydroxy-ymethyl -benzamide To a solution of 2,5-di-tert-butyl-7-fluoro-3-hydroxyisoindolin-1-one (4.3 g, 15.4 mmol, Eq: 1.00) in a mixture of MeOH (100 ml) and CH$_2$Cl$_2$ (150 ml) was added sodium borohydride (582 mg, 15.4 mmol, Eq: 1.00) at room temperature. The reaction mixture was stirred for 1 h at the same temperature. Then sodium borohydride (582 mg, 15.4 mmol, Eq: 1.00) was added again and the reaction mixture was stirred for an additional 1 h. After this time sodium borohydride (582 mg, 15.4 mmol, Eq: 1.00) was added one more time and reaction mixture stirred for 1 h. Reaction mixture was poured (carefully) into an aqueous HCl solution (10%, 100 mL). Product was extracted with CH$_2$Cl$_2$ (2×100 mL). The organic extracts were combined, dried (Na$_2$SO$_4$) and evaporated under vacuum to give 4.2 g of product (97% yield); LC/MS, m/z 282[M+H]$^+$. $^1$H NMR (400 MHz, CHLOROFORM-d) δ ppm 1.33 (s, 9 H) 1.49 (s, 9 H) 4.59 (s, 2 H) 6.02 (br. s., 2 H) 7.08 (dd, J=12.63, 1.77 Hz, 1 H) 7.22 (d, J=1.77 Hz, 1 H).

Step 2. Preparation of 4,N-Di-tert-butyl-2-fluoro-6-methyl-benzamide

To a solution of N,4-di-tert-butyl-2-fluoro-6-(hydroxymethyl)benzamide (4.3 g, 15.3 mmol, Eq: 1.00) in MeOH (100 ml) was added Pd—C 10% (50% wet) (1.19 g) and the reaction mixture was stirred under H$_2$ atmosphere (balloon) for 3 h. Reaction mixture was filtered over a celite pad and the celite pad washed with EtOH(3×50 mL). The combined filtrate and washes were evaporated under vacuum to give 4.01 g of product as a white solid (99% yield); LC/MS, m/z 266 [M+H]$^+$. $^1$H NMR (400 MHz, CHLOROFORM-d) δ ppm 1.30 (s, 9 H) 1.48 (s, 9 H) 2.41 (s, 3 H) 5.60 (br. s., 2 H) 6.90-6.95 (m, 1 H) 7.00 (d, J=0.51 Hz, 1 H).

Step 3. Preparation of 4-tert-Butyl-2-fluoro-6-methyl-benzamide

A solution of N,4-di-tert-butyl-2-fluoro-6-methylbenzamide (4.01 g, 15.1 mmol, Eq: 1.00) in TFA (48 ml) (4×12 mL, microwave vials) was stirred at 100° C. for 3 h under microwave assisted conditions. The contents of the four microwave vials were combined, evaporated under vacuum and residue was poured (carefully) into an aqueous saturated solution of NaHCO$_3$ (100 mL) and the product was extracted with CH$_2$Cl$_2$ (2×100 mL). The combined organic extracts were dried (Na$_2$SO$_4$) and evaporated under vacuum. The crude material was purified by chromatography (SiO$_2$, CH$_2$Cl$_2$ 100% to 30% AcOEt, in 30 min) to afford the desired product (2.55 g, 81% yield as a white solid. LC/MS, m/z 210[M+H]$^+$. $^1$H NMR (400 MHz, CHLOROFORM-d) δ ppm 1.32 (s, 9 H) 2.49 (t, J=0.63 Hz, 3 H) 5.86 (br. s., 2 H) 6.94-7.00 (m, 1 H) 7.05 (dd, J=1.26, 0.51 Hz, 1 H).

Step 4. Preparation of 4-tert-Butyl-n-[1-dimethylamino-meth-(e)-ylidene]-2-fluoro-6-methyl-benzamide To a solution of 4-tert-butyl-2-fluoro-6-methylbenzamide (1.28 g, 6.12 mmol, Eq: 1.00) in THF (49.2 ml) was added N,N-dimethylformamide dimethyl acetal (802 mg, 897 μl, 6.73 mmol, Eq: 1.1) and reaction mixture was heated to reflux temperature for 3 h. The reaction mixture was evaporated to dryness under vacuum to afford the desired product (1.6 g, 99% yield). The crude product was used in the next step without any further purification. $^1$H NMR (400 MHz, CHLOROFORM-d) δ ppm 1.30 (s, 9 H) 2.42 (s, 3 H) 3.16 (s, 3 H) 3.20 (s, 3 H) 6.93 (dd, J=11.75, 1.64 Hz, 1 H) 6.99 (s, 1 H) 8.57 (s, 1 H).

Step 5. Preparation of
6-tert-Butyl-8-fluoro-2H-isoquinolin-1-one,
potassium Salt To a solution of (E)-4-tert-butyl-N-((dimethylamino)methylene)-2-fluoro-6-methylbenzamide (1.6 g, 6.05 mmol, Eq: 1.00) in THF (38 mL) was added potassium tert-butoxide (7.87 ml of 1M, 7.87 mmol, Eq: 1.30) and the reaction mixture was heated to reflux temperature for 2 h (a precipitate was formed). Reaction mixture was cooled to room temperature and ether (40 ml) was added. The mixture was stirred for 30 min. The solid was collected by filtration (under vacuum) and washed with ether (40 ml), to give 1.22 g of product as a white solid (78% yield); LC/MS, m/z 220[M+H]$^+$.

Step 6. Preparation of
6-tert-Butyl-8-fluoro-2H-isoquinolin-1-one

To a suspension of 6-tert-butyl-8-fluoro-2H-isoquinolin-1-one, potassium salt (2.4 g, 9.29 mmol, Eq: 1.00) in DCM (200 ml) was added aqueous HCl (100 mL), the reaction mixture was stirred for 30 min at RT. Organic layer was separated, dried (Na$_2$SO$_4$) and evaporated under vacuum to give product as a white powder (1.9 g) in 93% yield; LC/MS, m/z 220[M+H]$^+$. $^1$H NMR (400 MHz, CHLOROFORM-d) δ ppm 7.70 (dd, J=7.20, 1.14 Hz, 1 H) 8.32 (dd, J=7.07, 5.81 Hz, 1 H) 8.42 (dd, J=13.89, 1.77 Hz, 1 H) 8.60 (d, J=1.77 Hz, 1 H).

Step 7. Preparation of 2-(6-tert-Butyl-8-fluoro-1-oxo-1H-isoquinolin-2-yl)-4-iodo-pyridine-3-carbaldehyde To a solution of 6-tert-butyl-8-fluoroisoquinolin-1(2H)-one (225 mg, 1.03 mmol, Eq: 1.00) in THF (11.1 ml) was added lithium bis(trimethylsilyl)amide in THF (1 M) (1.13 ml, 1.13 mmol, Eq: 1.1) at room temperature. The reaction mixture was stirred for 20 min. at the same temperature. Then 2-fluoro-4-iodonicotinaldehyde (335 mg, 1.33 mmol, Eq: 1.3) in THF (5 mL) was added. The reaction mixture was heated to 65° C. and stirred for 3 h. Then the reaction was poured into an aqueous-saturated solution of NH$_4$Cl (30 mL) and product was extracted with EtOAc (2×50 mL). The combined organic extracts were dried (Na$_2$SO$_4$) and evaporated under vacuum. Crude was diluted with CH$_2$Cl$_2$ (2 mL) and purified by chromatography (SiO$_2$, Hex:AcOEt, 100% to 70% in 25 min) to afford the desired product (350 mg) as a light yellow powder. LC/MS, m/z 451[M+H]$^+$. $^1$H NMR (400 MHz, CHLOROFORM-d) δ ppm 1.39 (s, 9 H) 6.65 (dd, J=7.58, 2.02 Hz, 1 H) 7.21 (dd, J=13.64, 1.77 Hz, 1 H) 7.31 (d, J=1.77 Hz, 1 H) 7.55 (d, J=7.58 Hz, 1 H) 7.91 (d, J=5.05 Hz, 1 H) 8.28 (d, J=5.31 Hz, 1 H) 9.94 (s, 1 H).

Example 23

Preparation of 6-tert-butyl-8-fluoro-2-{3-hydroxymethyl-4-[1-methyl-5-(5-methyl-4,5,6,7-tetrahydropyrazolo[1,5-a]pyrazin-2-ylamino)-6-oxo-1,6-dihydro-pyridazin-3-yl]-pyridin-2-yl}-2H-isoquinolin-1-one

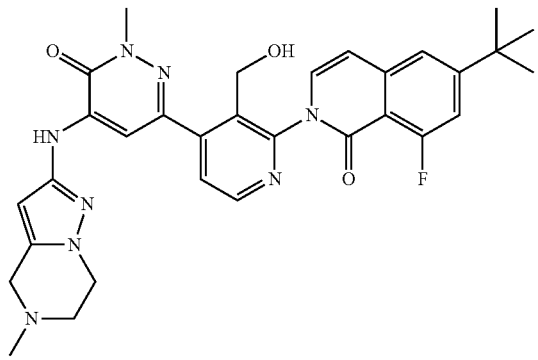 [SMILES: CN1CCn2nc(Nc3cc(-c4ccnc(-n5ccc6cc(C(C)(C)C)cc(F)c6c5=O)c4CO)nn(C)c3=O)cc2C1]

Preparation by a similar procedure to example 1 (Step 5-6), except substituting 6-chloro-2-methyl-4-(5-methyl-4,5,6,7-tetrahydropyrazolo[1,5-a]pyrazin-2-ylamino)pyridazin-3(2H)-one for 6-chloro-2-methyl-4-(5-(1-methylpiperidin-4-yl)pyridin-2-ylamino)pyridazin-3(2H)-one and substituting 2-(6-tert-Butyl-8-fluoro-1-oxo-1H-isoquinolin-2-yl)-4-iodo-pyridine-3-carbaldehyde for 2-(6-tert-butyl-8-fluoro-1-oxophthalazin-2(1H)-yl)-4-iodonicotinaldehyde in step 5 afforded 60 mg of the title compound as an off-white solid. (M+H)$^+$=585 m/e. $^1$H NMR (400 MHz, CHLOROFORM-d) δ ppm 1.42 (s, 9 H) 2.55 (s, 3 H) 2.98 (br. s., 2 H) 3.70 (br. s., 2 H) 3.92 (s, 3 H) 4.18 (br. s., 2 H) 4.24 (dd, J=10.74, 3.16 Hz, 1 H) 4.44-4.63 (m, 2 H) 5.91 (s, 1 H) 6.64 (dd, J=7.58, 2.02 Hz, 1 H) 7.24 (dd, J=13.64, 1.77 Hz, 1 H) 7.28 (d, J=7.58 Hz, 1 H) 7.35 (d, J=1.77 Hz, 1 H) 7.62 (d, J=5.05 Hz, 1 H) 7.93 (s, 1 H) 8.00 (s, 1 H) 8.68 (d, J=5.05 Hz, 1 H).

Example 24

Preparation of 6-tert-butyl-8-fluoro-2-{3-hydroxymethyl-4-[1-methyl-5-(5-oxetan-3-yl-4,5,6,7-tetrahydro-pyrazolo[1,5-a]pyrazin-2-ylamino)-6-oxo-1,6-dihydro-pyridazin-3-yl]-pyridin-2-yl}-2H-isoquinolin-1-one

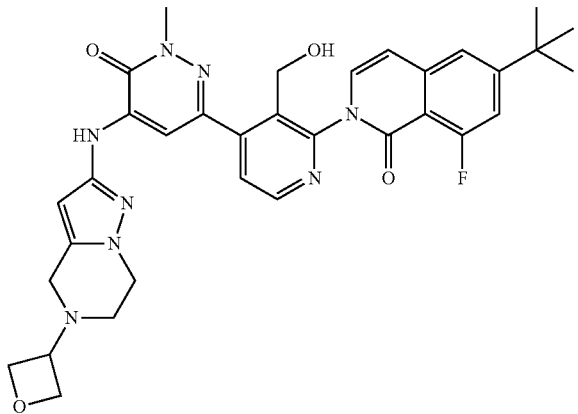 [SMILES: Cn1nc(-c2ccnc(-n3ccc4cc(C(C)(C)C)cc(F)c4c3=O)c2CO)cc(Nc2cc3n(n2)CCN(C2COC2)C3)c1=O]

Preparation by a similar procedure to example 1 (Step 5-6), except substituting 6-chloro-2-methyl-4-(5-oxetan-3-yl-4,5, 6,7-tetrahydro-pyrazolo[1,5-a]-pyrazin-2-ylamino)-2H-pyridazin-3-one for 6-chloro-2-methyl-4-(5-(1-methylpiperidin-4-yl)pyridin-2-ylamino)pyridazin-3(2H)-one and substituting 2-(6-tert-Butyl-8-fluoro-1-oxo-1H-isoquinolin-2-yl)-4-iodo-pyridine-3-carbaldehyde for 2-(6-tert-butyl-8-fluoro-1-oxophthalazin-2(1H)-yl)-4-iodonicotinaldehyde in step 5 afforded 100 mg of the title compound as an off-white solid. (M+H)$^+$=627 m/e. $^1$H NMR (400 MHz, CHLOROFORM-d) δ ppm 1.42 (s, 9 H) 2.84-2.96 (m, 2 H) 3.60-3.71 (m, 2 H) 3.80-3.87 (m, 1 H) 3.92 (s, 3 H) 4.19 (t, J=5.43 Hz, 2 H) 4.46-4.60 (m, 2 H) 4.70-4.75 (m, 2 H) 4.76-4.81 (m, 2 H) 5.96 (s, 1 H) 6.65 (dd, J=7.45, 2.15 Hz, 1 H) 7.21-7.27 (m, 2 H) 7.27 (d, J=7.8 Hz, 1 H) 7.35 (d, J=1.77 Hz, 1 H) 7.62 (d, J=5.05 Hz, 1 H) 7.92 (s, 1 H) 8.02 (s, 1 H) 8.68 (d, J=5.05 Hz, 1 H).

Example 25

Preparation of 6-tert-Butyl-2-{4-[5-(5-ethyl-4,5,6,7-tetrahydro-pyrazolo[1,5-a]pyrazin-2-ylamino)-1-methyl-6-oxo-1,6-dihydro-pyridazin-3-yl]-3-hydroxymethyl-pyridin-2-yl}-8-fluoro-2H-isoquinolin-1-one

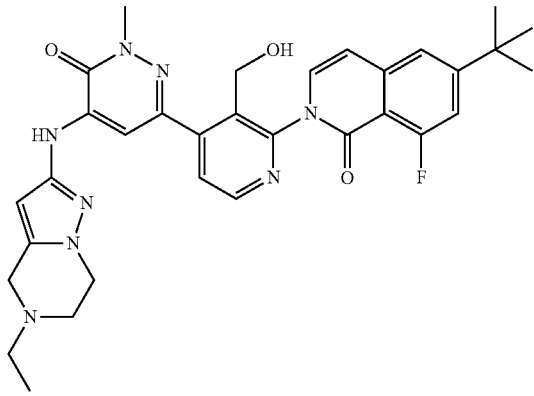 [SMILES: CCN1CCn2nc(Nc3cc(-c4ccnc(-n5ccc6cc(C(C)(C)C)cc(F)c6c5=O)c4CO)nn(C)c3=O)cc2C1]

Preparation by a similar procedure to example 1 (Step 5-6), except substituting 6-chloro-4-(5-ethyl-4,5,6,7-tetrahydro-pyrazolo[1,5-a]pyrazin-2-ylamino)-2-methyl-2H-pyridazin-3-one for 6-chloro-2-methyl-4-(5-(1-methylpiperidin-4-yl)pyridin-2-ylamino)pyridazin-3(2H)-one and substituting 2-(6-tert-Butyl-8-fluoro-1-oxo-1H-isoquinolin-2-yl)-4-iodo-pyridine-3-carbaldehyde for 2-(6-tert-butyl-8-fluoro-1-oxophthalazin-2(1H)-yl)-4-iodonicotinaldehyde in step 5 afforded 65 mg of the title compound as a light yellow solid. (M+H)$^+$=599 m/e. $^1$H NMR (400 MHz, CHLOROFORM-d) δ ppm 1.17-1.27 (m, 3 H) 1.41 (s, 9 H) 2.68 (br. s., 2 H) 2.98 (br. s., 2 H) 3.70 (br. s., 2 H) 3.92 (s, 3 H) 4.14 (br. s., 2 H) 4.24 (dd, J=10.61, 3.28 Hz, 1 H) 4.43-4.63 (m, 2 H) 5.92 (s, 1 H) 6.64 (dd, J=7.58, 2.02 Hz, 1 H) 7.24 (dd, J=13.39, 1.77 Hz, 1 H) 7.28 (d, J=7.4 Hz, 1 H) 7.35 (d, J=1.52 Hz, 1 H) 7.62 (d, J=5.05 Hz, 1 H) 7.91 (s, 1 H) 8.00 (s, 1 H) 8.68 (d, J=5.05 Hz, 1 H).

Example 26

Preparation of 6-tert-Butyl-2-{4-[5-(5-cyclopropylmethyl-4,5,6,7-tetrahydro-pyrazolo[1,5-a]pyrazin-2-ylamino)-1-methyl-6-oxo-1,6-dihydro-pyridazin-3-yl]-3-hydroxymethyl-pyridin-2yl}-8-fluoro-2H-phthalazin-1-one

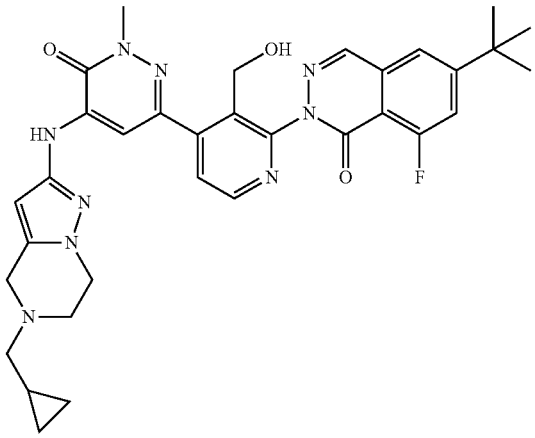 [SMILES: Cn1nc(-c2ccnc(-n3ncc4cc(C(C)(C)C)cc(F)c4c3=O)c2CO)cc(Nc2cc3n(n2)CCN(CC2CC2)C3)c1=O]

Preparation by a similar procedure to example 21, except substituting cyclopropylmethanamine for oxetan-3-amine in step 1 afforded 100 mg of the title compound as a pale yellow solid. (M+H)$^+$=626 m/e. $^1$H NMR (300 MHz, CHLOROFORM-d) δ ppm 0.01 (d, J=4.15 Hz, 2 H) 0.42 (d, J=7.55 Hz, 2 H) 0.77 (br. s., 1 H) 1.22 (s, 9 H) 2.30 (br. s., 2 H) 2.86 (br. s., 2 H) 3.58 (br. s., 2 H) 3.69 (s, 3 H) 3.77 (t, J=7.18 Hz, 1 H) 3.96 (br. s., 2 H) 4.32 (d, J=7.18 Hz, 2 H) 5.65 (s, 1 H) 7.26-7.36 (m, 2 H) 7.41 (d, J=4.91 Hz, 1 H) 7.68 (s, 1 H) 7.76 (s, 1 H) 8.10 (d, J=2.64 Hz, 1 H) 8.50 (d, J=5.29 Hz, 1 H).

Scheme I

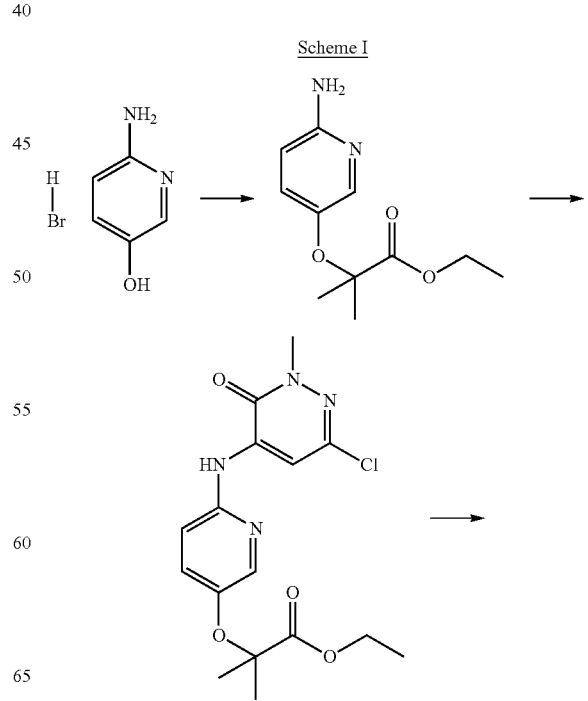

111
-continued

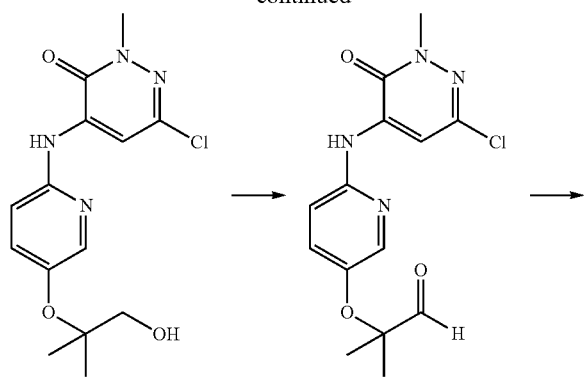

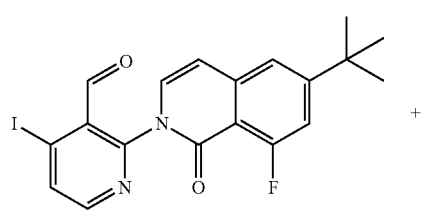

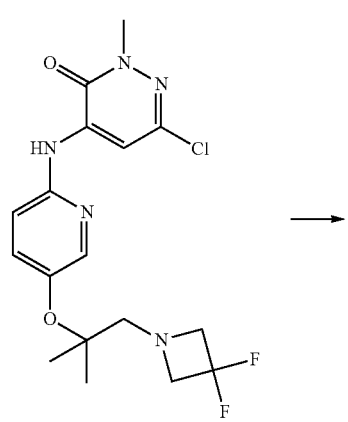

112
-continued

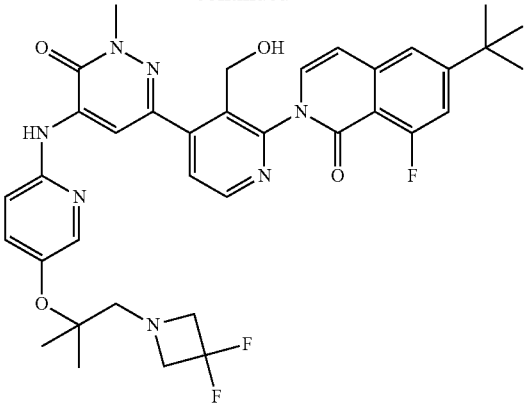

Preparation of I-27

Step 1. Preparation of 2-(6-amino-pyridin-3-yloxy)-2-methyl-propionic Acid Ethyl Ester

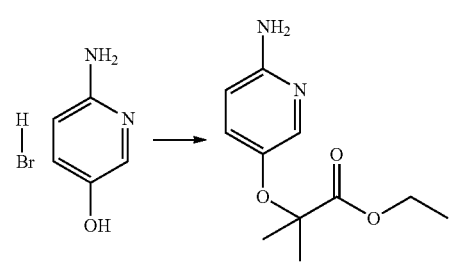

To a flask containing 6-aminopyridin-3-ol hydrobromide (2 g, 10.5 mmol) and ethyl-2-bromo-2-methylpropanate (2.04 g, 10.5 mmol) in anhydrous acetonitrile (25 ml) was added cesium carbonate (10.7 g, 33 mmol) and the material was stirred for 16 hours under argon atmosphere. Water (60 ml) and ethyl acetate (60 ml) were added and the material was shaken in a separatory funnel. The organic phase was collected and the aqueous phase was back extracted with ethyl acetate (2×50 ml). The combined organic phases were dried over magnesium sulfate, filtered and concentrated in vacuo. to provide a golden brown solid (1.626 g) (M+H)=225 m/e.

Step 2. Preparation of 2-[6-(6-chloro-2-methyl-3-oxo-2,3-dihydro-pyridazin-4-ylamino)-pyridin-3-yloxy]-2-methyl-propionic Acid Ethyl Ester

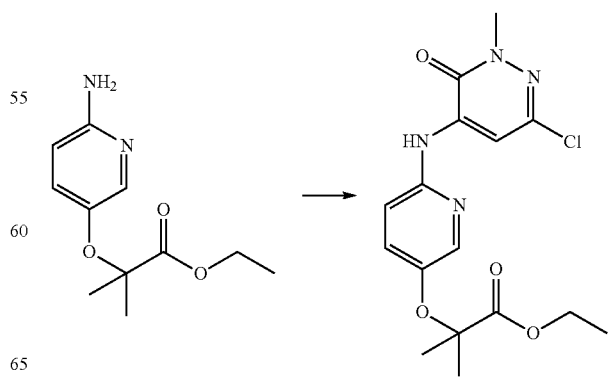

A flask containing 2-(6-amino-pyridin-3-yloxy)-2-methyl-propionic acid ethyl ester (1.365 g, 6.09 mmol), 4-bromo-6-chloro-2-methylpyridazin-3(2H)-one (1.77 g, 7.91 mmol), 4,5-bis(diphenylphosphino)-9,9-dimethylxanthene (528 mg, 0.913 mmol) and cesium carbonate (6.94 g, 21.3 mmol) in dry dioxane (60 ml) was evacuated under vacuum and back filled with argon (repeat 3 times). Tris(dibenzylideneacetone)dipalladium (0) (418 mg, 0.457 mmol) was added and the flask evacuated under vacuum and back filled with argon (repeat 3 times). The flask was place in an oil bath heated to 90° C. and stirred for 16 hours under argon atmosphere. The flask was cooled to ambient and the material was filtered through a plug of celite, rinsing well with dioxane. The volatiles were concentrated in vacuo and the residue was purified by silica gel chromatography, eluting with 5% to 25% ethyl acetate/hexane to provide the desired product as a light yellow-brown powder (2.035 g). (M+H)$^+$=367 m/e. $^1$H NMR (300 MHz, CHLOROFORM-d) δ ppm 1.30 (t, J=7.18 Hz, 3 H) 1.59 (s, 6 H) 3.80 (s, 3 H) 4.26 (q, J=7.18 Hz, 2 H) 6.83 (d, J=9.06 Hz, 1 H) 7.26-7.30 (m, 1 H) 8.04 (d, J=3.02 Hz, 1 H) 8.18 (s, 1 H) 8.22 (s, 1 H).

Step 3. Preparation of 6-chloro-4-[5-(2-hydroxy-1,1-dimethyl-ethoxy)-pyridin-2-ylamino]-2-methyl-2H-pyridazin-3-one

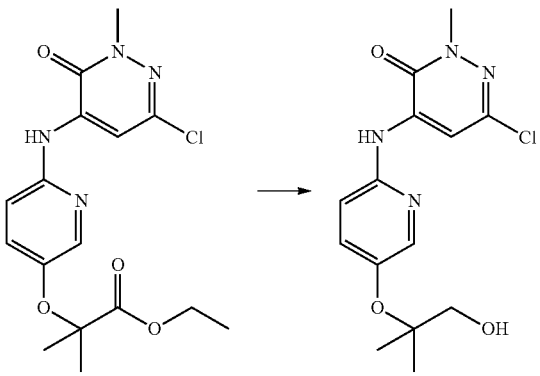 [SMILES: CCOC(=O)C(C)(C)Oc1ccc(Nc2cc(Cl)nn(C)c2=O)nc1 ; Cn1nc(Cl)cc(Nc2ccc(OC(C)(C)CO)cn2)c1=O]

2-[6-(6-Chloro-2-methyl-3-oxo-2,3-dihydro-pyridazin-4-ylamino)-pyridin-3-yloxy]-2-methyl-propionic acid ethyl ester (1.23 g, 3.35 mmol, Eq: 1.00) was dissolved in anhydrous THF (25 ml) and cooled to −30° C. (dry ice/acetonitrile cooling bath) under nitrogen atmosphere A solution of lithium aluminum hydride (4.7 ml, 4.69 mmol, 1.0 M in THF) was added slowly, over 10 minutes via drop-wise addition. The mixture was stirred for 1 hour while maintaining the bath temperature at about −20° C. The reaction was carefully quenched by adding water (0.1 ml) and stirring for 10 minutes at ambient. Then a 5% aqueous solution of sodium hydroxide (0.19 ml) was added and the mixture stirred for 10 minutes. Water (0.19 ml) was added and stirring continued for 10 minutes. Finally magnesium sulfate was added and the material was filtered through a plug of celite, rinsing well with tetrahydrofuran. The combined filtrate and washes were concentrated on a rotary evaporator to about half the volume. Ethyl acetate (50 ml) and water (70 ml) was added and the material was shaken in a separatory funnel. The organic phase was collected and the aqueous phase was back extracted with ethyl acetate (2×40 ml). The organics were combined, dried with magnesium sulfate, filtered and concentrated in vacuo. The residue was triturated from hot dichloromethane/hexanes to provide the desired product as a light yellow-brown solid (1.041 g). (M+H)=325 m/e. $^1$H NMR (300 MHz, CHLOROFORM-d) δ ppm 1.28 (s, 6 H) 3.81 (s, 3 H) 6.92 (d, J=8.69 Hz, 1 H) 7.30 (s, 1 H) 7.36 (dd, J=8.69, 2.64 Hz, 1 H) 8.12 (d, J=2.64 Hz, 1 H) 8.28 (s, 1 H).

Step 4. Preparation of 2-[6-(6-Chloro-2-methyl-3-oxo-2,3-dihydro-pyridazin-4-ylamino)-pyridin-3-yloxy]-2-methyl-propionaldehyde

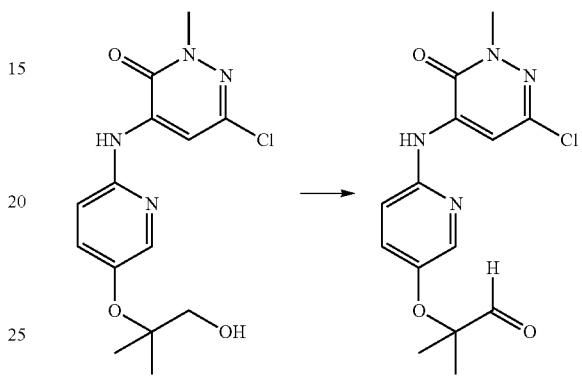

To a suspension of 6-chloro-4-(5-(1-hydroxy-2-methylpropan-2-yloxy)pyridin-2-ylamino)-2-methylpyridazin-3(2H)-one (750 mg, 2.31 mmol, Eq: 1.00) in DCM (100 ml) was added Dess-Martin periodinane (1.27 g, 3.00 mmol, Eq: 1.30). The reaction mixture was stirred at room temperature for about 40 minutes. Ether was added (100 mL) followed by 50 ml NaOH solution (1 M). The mixture was stirred for additional 15 minutes and transferred to separatory funnel. The organic layer was washed with equal volume of NaOH (1M) water (50 mL), dried (Na$_2$SO$_4$) and evaporated under vacuum to afford the desired product (668 mg) as a light brown powder. (M+H)=323 m/e. $^1$H NMR (400 MHz, DMSO-d$_6$) δ ppm 1.36 (s, 6 H) 3.68 (s, 3 H) 7.43-7.47 (m, 1 H) 7.51-7.55 (m, 1 H) 8.10 (dd, J=3.03, 0.51 Hz, 1 H) 8.27 (s, 1 H) 9.69 (s, 1 H) 9.82 (s, 1 H).

Step 5. Preparation of 6-Chloro-4-{5-[2-(3,3-difluoro-azetidin-1-yl)-1,1-dimethyl-ethoxy]-pyridin-2-ylamino}-2-methyl-2H-pyridazin-3-one

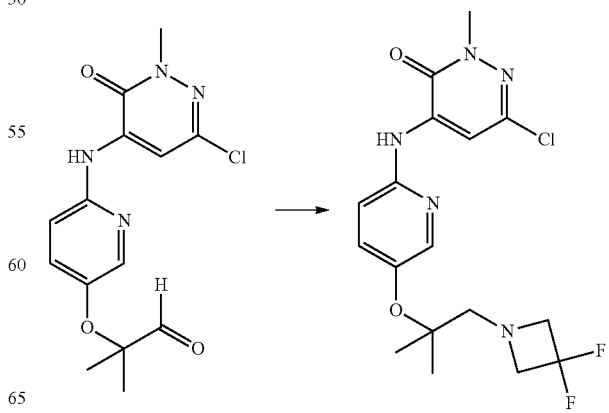

To a solution of 2-(6-(6-chloro-2-methyl-3-oxo-2,3-dihydropyridazin-4-ylamino)pyridin-3-yloxy)-2-methylpropanal (665 mg, 2.06 mmol, Eq: 1.00) in DCE (70 ml) was added 3,3-difluoroazetidine hydrochloride (347 mg, 2.68 mmol, Eq: 1.30). The mixture was stirred at RT for 1 h, then sodium triacetoxyborohydride (655 mg, 3.09 mmol, Eq: 1.5) was added and stirring was continued for 18 h. The reaction mixture was diluted with saturated NaHCO$_3$ solution and extracted with DCM (5×20 mL). The organic layer was dried (MgSO$_4$) and concentrated in vacuo. The resultant residue was purified by chromatography (SiO$_2$-50 g, Hex:AcOEt, 7:3 in 20 min, then 50% in 30 min) to afford the desired product (566 mg) as a white powder. (M+H)$^+$=400 m/e. $^1$H NMR (400 MHz, CHLOROFORM-d) δ ppm 1.29 (s, 6 H) 2.79 (br. s., 2 H) 3.70-3.81 (m, 4 H) 3.83 (s, 3 H) 6.87 (dd, J=8.84, 0.51 Hz, 1 H) 7.32 (d, J=8.59 Hz, 1 H) 8.10 (d, J=2.78 Hz, 1 H) 8.22 (s, 1 H) 8.28 (s, 1 H).

Example 27

Preparation of 6-tert-butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-8-fluoro-2H-isoquinolin-1-one

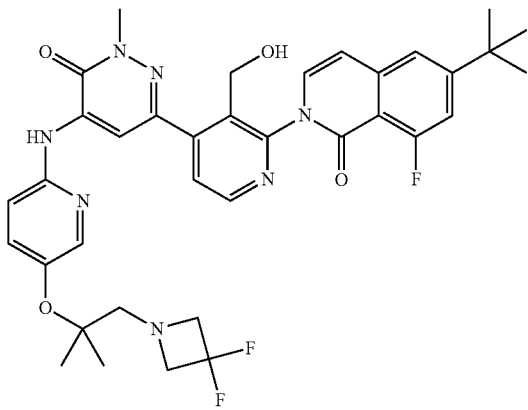

Preparation by a similar procedure to example 1 (Step 5-6), except substituting 6-chloro-4-{5-[2-(3,3-difluoro-azetidin-1-yl)-1,1-dimethyl-ethoxy]-pyridin-2-ylamino}-2-methyl-2H-pyridazin-3-one for 6-chloro-2-methyl-4-(5-(1-methylpiperidin-4-yl)pyridin-2-ylamino)pyridazin-3(2H)-one and substituting 2-(6-tert-Butyl-8-fluoro-1-oxo-1H-isoquinolin-2-yl)-4-iodo-pyridine-3-carbaldehyde for 2-(6-tert-butyl-8-fluoro-1-oxophthalazin-2(1H)-yl)-4-iodonicotinaldehyde in step 5 afforded 95 mg of the title compound as an off-white solid. (M+H)$^+$=690 m/e. $^1$H NMR (400 MHz, CHLOROFORM-d) δ ppm 1.30 (s, 6 H) 1.41 (s, 9 H) 2.80 (br. s., 1 H) 3.76 (br. s., 4 H) 3.94 (s, 3 H) 4.14 (dd, J=11.12, 3.03 Hz, 1 H) 4.45-4.67 (m, 2 H) 6.65 (dd, J=7.58, 2.02 Hz, 1 H) 6.96 (d, J=8.84 Hz, 1 H) 7.24 (dd, J=13.64, 1.77 Hz, 1 H) 7.30 (d, J=7.33 Hz, 2 H) 7.31-7.36 (m, 2 H) 7.63 (d, J=5.05 Hz, 1 H) 8.09 (d, J=2.78 Hz, 1 H) 8.31 (s, 1 H) 8.64 (s, 1 H) 8.71 (d, J=5.05 Hz, 1 H).

Preparation of I-28

Step 1. 4-(6-tert-Butyl-8-fluoro-1-oxo-1H-phthalazin-2-yl)-2-chloro-pyridine-3-carbaldehyde

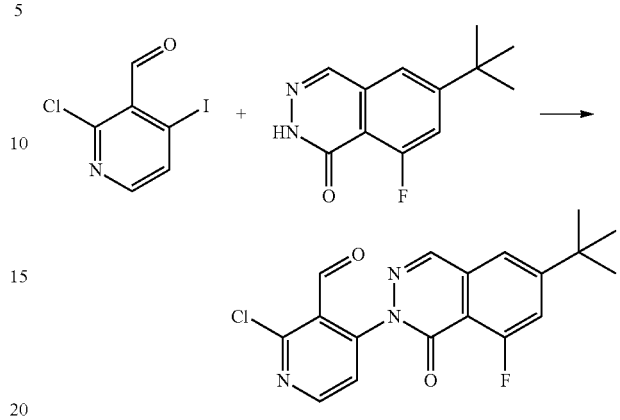

In a 50 mL round-bottomed flask, 2-chloro-4-iodonicotinaldehyde (389 mg, 1.45 mmol, Eq: 1.6), 6-tert-butyl-8-fluorophthalazin-1(2H)-one (200 mg, 908 μmol, Eq: 1.00) and potassium carbonate (251 mg, 1.82 mmol, Eq: 2) were combined with DMSO (8 ml) to give a yellow solution. The solution was degassed for 5 min with argon. Copper(I) iodide (173 mg, 908 μmol, Eq: 1.00) was added. The reaction mixture was heated to 110° C. and stirred for 2 h and the reaction was allowed to cool to room temperature. The reaction was diluted with 1:1 H$_2$O/sat. NH$_4$Cl (80 mL) and the resulting solid collected by filtration. The solid was washed several times with 1:1 H$_2$O/sat. NH$_4$Cl, then water (2×) and then EtOAc:hexanes (3:1, 2×). A lot of color in the organic phase. A brown solid remained. Solid was washed with EtOAc and then CH$_2$Cl$_2$ several times. The combined organic extracts were washed with water, dried over MgSO4 and concentrated in vacuo. The resulting residue was purified by flash chromatography (silica gel, 40 g, 5% to 30% EtOAc in hexanes) to afford the desired product (170 mg) as a white solid. (M+H)$^+$=360 m/e. $^1$H NMR (300 MHz, CHLOROFORM-d) δ ppm 1.42 (s, 9 H) 7.40-7.65 (m, 3 H) 8.24 (d, J=2.64 Hz, 1 H) 8.66 (d, J=5.29 Hz, 1 H) 10.32 (s, 1 H).

Example 28

Preparation of 4-(6-tert-Butyl-8-fluoro-1-oxo-1H-phthalazin-2-yl)-3-hydroxymethyl-1'-methyl-5'-[5-(morpholine-4-carbonyl)-pyridin-2-ylamino]-1'H-[2,3']bipyridinyl-6'-one

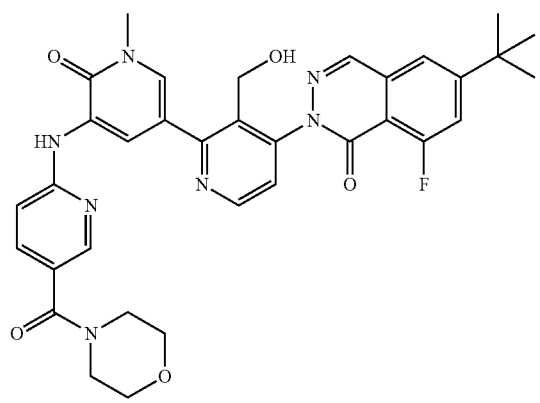 [SMILES: Cn1cc(-c2nccc(-n3ncc4cc(C(C)(C)C)cc(F)c4c3=O)c2CO)cc(Nc2ccc(C(=O)N3CCOCC3)cn2)c1=O]

Preparation by a similar procedure to example 8 except substituting 4-(6-tert-Butyl-8-fluoro-1-oxo-1H-phthalazin-2-yl)-2-chloro-pyridine-3-carbaldehyde for 2-(6-tert-Butyl-8-fluoro-1-oxo-1H-phthalazin-2-yl)-4-iodo-pyridine-3-carbaldehyde afforded 54 mg of the title compound as an off-white solid. ¹H NMR (400 MHz, CHLOROFORM-d) δ ppm 1.46 (s, 9H) 3.57-3.86 (s and overlapping m, 11 H) 4.05 (br. s., 1 H) 4.52 (br. s., 2 H) 6.88 (d, J=8.53 Hz, 1 H) 7.35 (d, J=5.27 Hz, 1 H) 7.55-7.64 (m, 2 H) 7.69 (dd, J=8.53, 2.26 Hz, 1 H) 7.91 (d, J=2.26 Hz, 1 H) 8.11 (s, 1 H) 8.36 (dd, J=11.29, 2.26 Hz, 2 H) 8.83 (d, J=5.02 Hz, 1 H) 9.05 (d, J=2.26 Hz, 1 H).

white solid. ¹H NMR (300 MHz, CHLOROFORM-d) δ ppm 1.30 (s, 9 H) 2.92 (s, 3 H) 3.61 (s, 3 H) 3.80-4.02 (m, 1 H) 4.36 (s, 2 H) 6.76 (d, J=9.06 Hz, 1 H) 7.21 (d, J=5.29 Hz, 1 H) 7.35-7.52 (m, 2 H) 7.73-7.90 (m, 2 H) 8.15 (s, 2 H) 8.19 (d, J=2.64 Hz, 1 H) 8.60-8.73 (m, 2 H) 9.01 (d, J=2.27 Hz, 1 H).

Example 30

Preparation of 6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-8-fluoro-2H-phthalazin-1-one

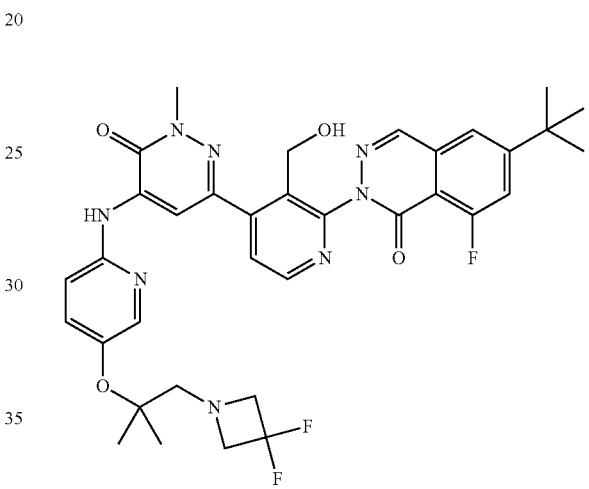

Example 29

Preparation of 4-(6-tert-Butyl-8-fluoro-1-oxo-1H-phthalazin-2-yl)-3-hydroxymethyl-5'-(5-methanesulfonyl-pyridin-2-ylamino)-1'-methyl-1'H-[2,3']bipyridinyl-6'-one

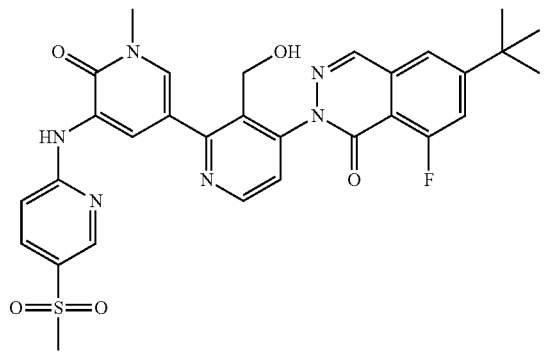

Preparation by a similar procedure to example 1 (Step 5-6), except substituting 6-chloro-4-{5-[2-(3,3-difluoro-azetidin-1-yl)-1,1-dimethyl-ethoxy]-pyridin-2-ylamino}-2-methyl-2H-pyridazin-3-one for 6-chloro-2-methyl-4-(5-(1-methylpiperidin-4-yl)pyridin-2-ylamino)pyridazin-3(2H)-one and substituting 2-(6-tert-Butyl-8-fluoro-1-oxo-1H-isoquinolin-2-yl)-4-iodo-pyridine-3-carbaldehyde for 2-(6-tert-butyl-8-fluoro-1-oxophthalazin-2(1H)-yl)-4-iodonicotinaldehyde in step 5 afforded 110 mg of the title compound as an off-white solid. (M+H)⁺=691 m/e. ¹H NMR (400 MHz, CHLOROFORM-d) δ ppm 1.28 (s, 6 H) 1.44 (s, 9 H) 2.77 (br. s., 2 H) 3.75 (br. s., 4 H) 3.85 (t, J=7.07 Hz, 1 H) 3.93 (s, 3 H) 4.55 (br. s., 2 H) 6.92 (d, J=8.84 Hz, 1 H) 7.31 (d, J=8.08 Hz, 1 H) 7.46-7.57 (m, 2 H) 7.64 (d, J=5.05 Hz, 1 H) 8.08 (d, J=2.78 Hz, 1 H) 8.23-8.35 (m, 2 H) 8.63 (s, 1 H) 8.74 (d, J=4.80 Hz, 1 H).

Preparation by a similar procedure to example 9 except substituting 4-(6-tert-Butyl-8-fluoro-1-oxo-1H-phthalazin-2-yl)-2-chloro-pyridine-3-carbaldehyde for 2-(6-tert-Butyl-8-fluoro-1-oxo-1H-phthalazin-2-yl)-4-iodo-pyridine-3-carbaldehyde afforded 54 mg of the title compound as an off- Preparation of I-31
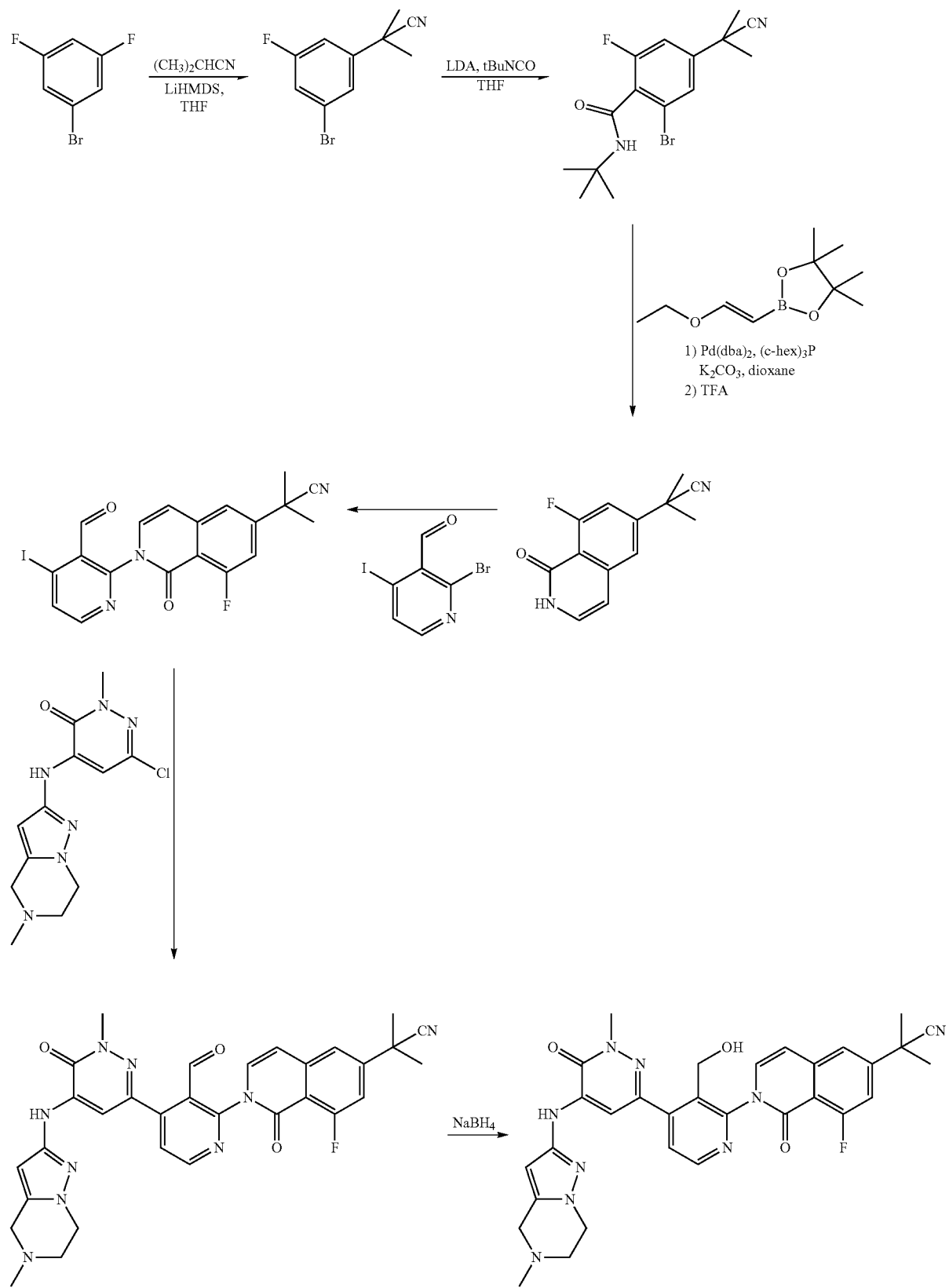
Scheme H

Step 1. Preparation of 2-(3-Bromo-5-fluoro-phenyl)-2-methyl -propionitrile

At 2-5° C. a solution of lithium bis(trimethylsilyl)amide in THF (326 ml of 1 M, 326 mmol, 1.05 equiv.) was added dropwise into a solution of 1-bromo-3,5-difluorobenzene (60 g, 311 mmol, 1.0 equiv.) and isobutyronitrile (25.8 g, 373 mmol, 1.2 equiv.) in 360 mL of THF. After stirring for 20 h, 13% starting reagent remained so an additional 0.1 eq of lithium bis(trimethylsilyl)amide was added. After an additional 6 hr, 10% starting reagent remained so another 0.1 eq. of lithium bis(trimethylsilyl)amide and 0.1 eq. of isobutyronitrile were added. The reaction mixture was stirred overnight. The reaction mixture was quenched with a 1 N HCl solution, then concentrated down to remove some of the THF. The reaction mixture was extracted with methyl-tert-butyl ether (2 times) and concentrated under reduced pressure to get the crude product (75.3 g) which was used as is.

Step 2. Preparation of 2-Bromo-N-tert-butyl-4-(cyano-dimethyl-methyl)-6-fluorobenzamide To a solution of 2-(3-bromo-5-fluorophenyl)-2-methylpropanenitrile (30 g, 124 mmol, 1.0 equiv.) in 180 mL THF was added lithium diisopropylamide (82.6 ml of 1.8 M, 149 mmol, 1.2 equiv.) dropwise at −75° C. The reaction mixture was stirred at −76° C. for 2 hr. The tert-butylisocyanate (18.4 g, 21.8 ml, 186 mmol, 1.5 equiv.) was added dropwise at −75° C. and stirring was continued for 2 hr. An additional 0.5 equiv. of tert-butylisocyanate was added and the reaction mixture was allowed to warm gradually to room temperature and stirred overnight. The reaction mixture was quenched with 180 mL water and the THF was then removed under reduced pressure at 60° C. IPA was added at 60° C. and the product was crystallized out from 180 mL $H_2O$ and 120 mL IPA at 60° C. The mixture was cooled to room temperature slowly overnight. The crystals were collected by filtration, washed with $H_2O$, $H_2O$/IPA (1/1), and heptane, and dried overnight to afford 2-bromo-N-tert-butyl-4-(2-cyanopropan-2-yl)-6-fluorobenzamide (34.7 g, 102 mmol, 82.1% yield) as white crystalline solid with >99% HPLC purity. $^1$H NMR (300 MHz, DMSO-$d_6$) δ ppm 1.34 (s, 9 H) 1.70 (s, 6 H) 7.47 (dd, J=10.01, 1.70 Hz, 1 H) 7.60 (s, 1 H) 8.34 (s, 1 H).

Step 3. Preparation of 2-(8-Fluoro-1-oxo-1,2-dihydro-isoquinolin-6-yl)-2-methyl-propionitrile A 500 mL round-bottomed flask was charged with 2-bromo-N-tert-butyl-4-(2-cyanopropan-2-yl)-6-fluorobenzamide (34.5 g, 101 mmol, 1 equiv.) and potassium carbonate (27.9 g, 202 mmol, 2 equiv.) and the flask was subsequently purged with nitrogen (3 times). 1,4-dioxane (242 ml) and water (34.5 ml) were added. The E-2-(2-ethoxyvinyl)-4,4,5,5-tetramethyl-1,3,2-dioxaborolane (28.0 g, 142 mmol, 1.4 equiv.) was then added by syringe. The reaction mixture was heated to 40° C. To the mixture was added bis(dibenzylideneacetone)palladium (2.33 g, 4.04 mmol, 0.04 equiv.) and tricyclohexylphosphine (2.27 g, 8.09 mmol, 0.08 equiv.) and the resulting mixture was heated with stirring at 90° C. (inner temperature)/100° C. (bath) for 2 h until reaction was complete. The reaction mixture was cooled to ambient temperature and quenched with 20% NaHSO$_3$ solution (150 mL) followed by stirring for 2 hr. The mixture was extracted with EtOAc (2 times), dried over MgSO$_4$, and concentrated under reduced pressure. The resultant product was dissolved with TFA (138 ml) in a 350 mL pressured bottle and heated to 100° C. (bath temp.) for 3 hr. The reaction mixture was transferred to a round-bottomed flask with toluene, and the TFA was removed under reduced pressure, then basified with 20% K$_2$CO$_3$ solution. The reaction mixture was extracted with EtOAc and then with DCM. Crystallization from methyl-tert-butylether afforded 2-(8-fluoro-1-oxo-1,2-dihydroisoquinolin-6-yl)-2-methylpropanenitrile (16.2 g, 69.6% yield) as a brown solid. $^1$H NMR (300 MHz, DMSO-$d_6$) δ ppm 1.74 (s, 6 H) 6.60 (dd, J=6.99, 1.70 Hz, 1 H) 7.16-7.28 (m, 1 H) 7.36 (dd, J=13.03, 1.70 Hz, 1 H) 7.61 (d, J=1.89 Hz, 1 H) 11.31 (br. s., 1 H).

Step 4. Preparation of 2-[8-Fluoro-2-(3-formyl-4-iodo -pyridin-2-yl)-1-oxo-1,2-dihydro-isoquinolin-6-yl]-2-methyl-propionitrile In a 100 mL round-bottomed flask 2-(8-fluoro-1-oxo-1,2-dihydroisoquinolin-6-yl)-2-methylpropanenitrile (800 mg, 3.47 mmol, 1 equiv.) was combined with THF (32.0 ml) to give a yellow suspension. A solution of lithium bis(trimethylsilyl)amide in THF 1M (4.52 ml, 4.52 mmol, 1.3 equiv.) was added. The reaction mixture was stirred at room temperature for 15 min. To the resultant amber solution was added 2-fluoro-4-iodonicotinaldehyde (1.31 g, 5.21 mmol, 1.5 equiv.). The reaction mixture was heated at 50° C. with stirring for 15 h. The reaction mixture was poured into 5 mL saturated NH$_4$Cl and 100 mL H$_2$O and extracted with DCM (3×100 mL). The organic layers were dried over Na$_2$SO$_4$ and concentrated in vacuo. The crude material was purified by flash chromatography (silica gel, 80 g, 0%, then 0% to 0.5% MeOH in DCM), followed by trituration with ether:hexanes (1:8) to afford 2-[8-fluoro -2-(3-formyl-4-iodo-pyridin-2-yl)-1-oxo-1,2-dihydro-isoquinolin-6-yl]-2-methyl-propionitrile as a pale yellow solid (830 mg). $(M+H)^+=462$ m/e.

Step 5. Preparation of 2-(8-Fluoro-2-{3-formyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-1-oxo-1,2dihydro-isoquinolin-6-yl)-2-methyl-propionitrile 6-chloro-2-methyl-4-(5-methyl-4,5,6,7-tetrahydropyrazolo[1,5-a]pyrazin-2-ylamino)pyridazin-3(2H)-one (511 mg, 1.73 mmol, 1 equiv.), bis(pinacolato)diboron (485 mg, 1.91 mmol, 1.1 equiv.) and potassium acetate (511 mg, 5.2 mmol, Eq: 3) were suspended in dioxane (25 ml). The reaction mixture was degassed under argon. X-PHOS (124 mg, 260 μmol, Eq: 0.15) and palladium(II) acetate (19.5 mg, 86.7 μmol, 0.05 equiv.) were added and the reaction mixture was stirred at 100° C. (external temperature) for 40 min. under an argon atmosphere until reaction was complete. Bath temperature was reduced to 80° C. Flask was raised out of the heating bath, but continued stirring. 2-(8-fluoro-2-(3-formyl-4-iodopyridin-2-yl)-1-oxo-1,2-dihydroisoquinolin-6-yl)-2-methylpropanenitrile (800 mg, 1.73 mmol, 1.0 equiv.) and potassium carbonate (719 mg, 5.2 mmol, 3 equiv.) were added, followed by 2.5 mL H$_2$O. Tricyclohexylphosphine (48.6 mg, 173 μmol, 0.1 equiv.) and bis(dibenzylideneacetone)palladium (49.9 mg, 86.7 μmol, 0.05 equiv.) were added. The reaction mixture was heated with vigorous stirring at 80° C. and stirred for 1.5 h. The reaction mixture was poured onto water. Some brine was added to break up the emulsion and the mixture was extracted with DCM (4 times). The combined organic extracts were dried over Na$_2$SO$_4$ and concentrated in vacuo. The resulting solid was triturated by adding 10 mL EtOAc followed by 75 mL ether. The solid was collected by filtration and washed several times with ether to give a pale green/grey solid (800 mg). (M+H)⁺=594 m/e. The product was used as is in the next step without further purification.

Example 31

Step 6. Preparation of 2-(8-Fluoro-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-1-oxo-1,2-dihydro-isoquinolin-6-yl)-2-methyl-proprionitrile

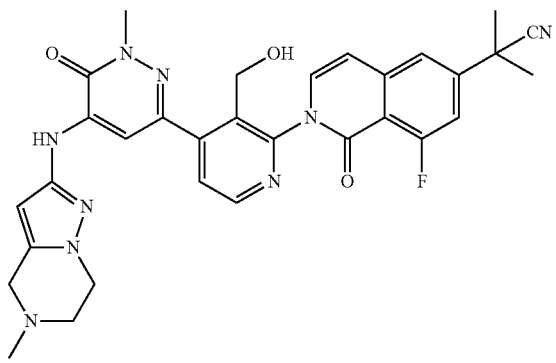 [SMILES: CN1CCn2nc(Nc3cc(-c4ccnc(-n5ccc6cc(C(C)(C)C#N)cc(F)c6c5=O)c4CO)nn(C)c3=O)cc2C1]

In a 25 mL round-bottomed flask, 2-(8-fluoro-2-{3-formyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-1-oxo-1,2-dihydro-isoquinolin-6-yl)-2-methyl-propionitrile (800 mg, 1.35 mmol, 1.0 equiv.) was combined with dry DCM (25 ml) and dry methanol (5 mL) to give a light yellow solution. The reaction mixture was cooled to 0° C. and sodium borohydride (91.8 mg, 2.43 mmol, Eq: 1.8) was added. The reaction mixture was stirred at 0° C. for 40 min. and then was quenched with 2 mL saturated NH₄Cl with stirring for 5 min. The reaction mixture was poured into 100 mL H₂O and extracted with DCM (3×150 mL). The combined organic layers were dried over Na₂SO₄ and concentrated in vacuo. The crude foam was taken up in 20 mL DCM and 15 mL methanol. To this mixture was added 200 mg of 10% Pd/C (Degussa brand). The reaction mixture was stirred at room temperature for 2 h. The solid was removed by filtration and washed several times with 10% methanol in DCM. The combined filtrate and washes were concentrated in vacuo. The crude material was purified by flash chromatography (silica gel, 40 g, 0% to 4% MeOH holding gradient as each peak came off). Center cut fractions were concentrated to give a glass, which was triturated with ether to afford 2-(8-fluoro-2-{3-hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-1-oxo-1,2-dihydro-isoquinolin-6-yl)-2-methyl-proprionitrile as an off-white solid. (M+H)⁺=596 m/e. ¹H NMR (300 MHz, CHLOROFORM-d) δ ppm 1.81 (s, 6 H) 2.52 (s, 3 H) 2.94 (t, J=5.67 Hz, 2 H) 3.65 (d, J=2.27 Hz, 2 H) 3.90 (s, 3 H) 4.05-4.22 (m, 3 H) 4.42-4.60 (m, 2 H) 5.85 (s, 1 H) 6.66 (dd, J=7.55, 1.89 Hz, 1 H) 7.22 (dd, J=12.46, 1.89 Hz, 1 H) 7.35 (d, J=7.55 Hz, 1 H) 7.53 (d, J=1.89 Hz, 1 H) 7.62 (d, J=4.91 Hz, 1 H) 7.92 (s, 1 H) 7.99 (s, 1 H) 8.68 (d, J=4.91 Hz, 1 H).

Example 32

Preparation of 6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl) -3-hydroxymethyl-pyridin-2-yl]-2H-phthalazin-1-one

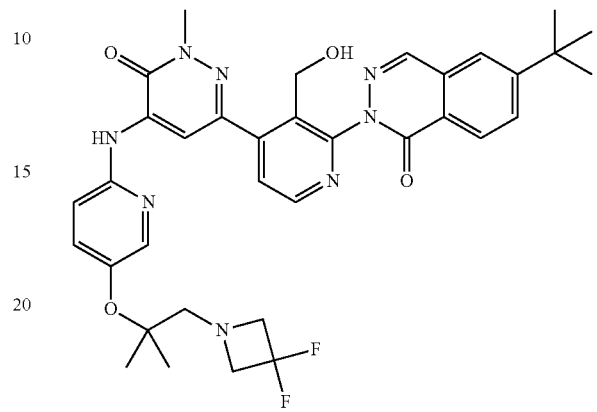

Preparation by a similar procedure to example 1 (Step 5-6), except substituting 6-chloro-4-{5-[2-(3,3-difluoro-azetidin-1-yl)-1,1-dimethyl-ethoxy]-pyridin-2-ylamino}-2-methyl-2H-pyridazin-3-one for 6-chloro-2-methyl-4-(5-(1-methylpiperidin-4-yl)pyridin-2-ylamino)pyridazin-3(2H)-one and substituting 2-(6-tert-Butyl-1-oxo-1H-isoquinolin-2-yl)-4-iodo-pyridine-3-carbaldehyde for 2-(6-tert-butyl-8-fluoro-1-oxophthalazin-2(1H)-yl)-4-iodonicotinaldehyde in step 5 afforded 149 mg of the title compound as an off-white solid. (M+H)⁺=673 m/e. ¹H NMR (400 MHz, CHLOROFORM-d) δ ppm 1.28 (br. s., 6 H) 1.46 (s, 9 H) 2.77 (br. s., 2 H) 3.75 (br. s., 4 H) 3.93 (s, 3 H) 3.98 (t, J=7.07 Hz, 1 H) 4.54 (br. s., 2 H) 6.93 (d, J=8.84 Hz, 1 H) 7.31 (d, J=7.07 Hz, 1 H) 7.64 (d, J=5.05 Hz, 1 H) 7.78 (d, J=1.52 Hz, 1 H) 7.90-7.95 (m, 1 H) 8.07 (d, J=2.53 Hz, 1 H) 8.29 (s, 1 H) 8.39 (d, J=0.76 Hz, 1 H) 8.45 (d, J=8.34 Hz, 1 H) 8.64 (s, 1 H) 8.75 (d, J=5.05 Hz, 1 H).

Example 33

Preparation of 2-{2-[4-(5-{5-[2-(3,3-Difluoro-azetidin-1-yl)-1,1-dimethyl-ethoxy]-pyridin-2-ylamino}-1-methyl-6-oxo-1,6-dihydro-pyridazin-3-yl) -3-hydroxymethyl-pyridin-2-yl]-8-fluoro-1-oxo-1,2-dihydro-isoquinolin-6-yl}-2-methyl-propionotrile

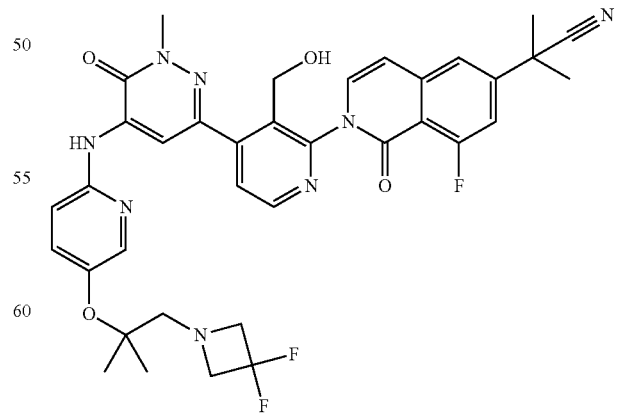

Preparation by a similar procedure to example 1 (Step 5-6), except substituting 6-chloro-4-{5-[2-(3,3-difluoro-azetidin- 1-yl)-1,1-dimethyl-ethoxy]-pyridin-2-ylamino}-2-methyl-2H-pyridazin-3-one for 6-chloro-2-methyl-4-(5-(1-methylpiperidin-4-yl)pyridin-2-ylamino)pyridazin-3(2H)-one in step 5 afforded 135 mg of the title compound as an off-white solid. (M+H)⁺=701 m/e ¹H NMR (400 MHz, CHLOROFORM-d) δ ppm 1.30 (br. s., 6 H) 1.81 (s, 6 H) 2.81 (br. s., 2 H) 3.81 (br. s., 4 H) 3.93 (s, 3 H) 4.01 (dd, J=10.36, 3.28 Hz, 1 H) 4.43-4.62 (m, 2 H) 6.67 (dd, J=7.58, 2.02 Hz, 1 H) 6.93 (d, J=8.84 Hz, 1 H) 7.23 (dd, J=12.25, 1.89 Hz, 1 H) 7.32 (br. s., 1 H) 7.37 (d, J=7.33 Hz, 1 H) 7.52-7.56 (m, 1 H) 7.64 (d, J=4.80 Hz, 1 H) 8.08 (d, J=2.78 Hz, 1 H) 8.31 (s, 1 H) 8.63 (s, 1 H) 8.71 (d, J=5.05 Hz, 1 H).

Example 34

Preparation of 2-(6-(2-(6-tert-Butyl-8-fluoro-1-oxophthalazin-2(1H)-yl)-3-(hydroxymethyl)pyridin-4-yl)-2-methyl-3-oxo-2,3-dihydropyridazin-4-ylamino)-5-methyl-4,5,6,7-tetrahydropyrazolo[1,5-a]pyrazine 5-oxide

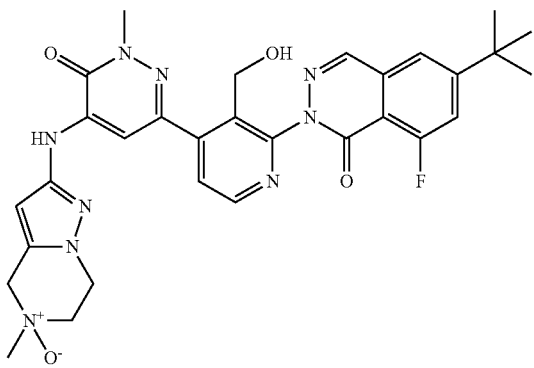 [SMILES: Cn1nc(-c2ccnc(-n3ncc4cc(C(C)(C)C)cc(F)c4c3=O)c2CO)cc(Nc2cc3n(n2)CC[N+](C)([O-])C3)c1=O]

To a solution of 6-tert-butyl-8-fluoro-2-(3-(hydroxymethyl)-4-(1-methyl-5-(5-methyl-4,5,6,7-tetrahydropyrazolo[1,5-a]pyrazin-2-ylamino)-6-oxo-1,6-dihydropyridazin-3-yl)pyridin-2-yl)phthalazin-1(2H)-one (500 mg, 854 μmol, 1 equiv.) in DCM (10 ml) was added 3-chlorobenzoperoxoic acid (191 mg, 854 μmol, 1 equiv.). The reaction mixture was stirred for 18 h. The reaction mixture was diluted with methylene chloride and washed with 1.0 N NaOH (aq). The layers were separated and the organic layer was washed with brine, dried over sodium sulfate, filtered and concentrated to afford a liquid that gradually hardened to a low melting, yellow solid under vacuum, overnight. The solid was dissolved in a minimum of methanol, diluted with methylene chloride and loaded onto a column. The crude material was purified by flash chromatography (silica gel, 40 g, 50% 60:10:1 DCM:MeOH:NH₄ OH in DCM) to give 2-(6-(2-(6-tert-butyl-8-fluoro-1-oxophthalazin-2(1H) -yl)-3-(hydroxymethyl)pyridin-4-yl)-2-methyl-3-oxo-2,3-dihydropyridazin-4-ylamino)-5-methyl-4,5,6,7-tetrahydropyrazolo[1,5-a]pyrazine 5-oxide (158.5 mg, 263 μmol, 30.9% yield) as a yellow solid. (M+H)⁺=602 m/e. ¹H NMR (300 MHz, METHANOL-d₄) d ppm 1.47 (s, 9 H) 3.45 (s, 3 H) 3.74 (dt, J=12.46, 2.46 Hz, 1 H) 3.89 (s, 3 H) 4.07 (td, J=11.80, 4.72 Hz, 1 H) 4.25-4.43 (m, 1 H) 4.45-4.62 (m, 2 H) 4.61-4.85 (m, 3 H) 6.13 (s, 1 H) 7.54-7.79 (m, 2 H) 7.87 (d, J=1.51 Hz, 1 H) 8.07 (s, 1 H) 8.50 (d, J=2.64 Hz, 1 H) 8.66 (d, J=5.29 Hz, 1 H).

Biological Assay Data

Bruton's Tyrosine Kinase (Btk) Inhibition Assay

The assay is a capture of radioactive $^{33}P$ phosphorylated product through filtration. The interactions of Btk, biotinylated SH₂ peptide substrate (Src homology), and ATP lead to phosphorylation of the peptide substrate. Biotinylated product is bound streptavidin sepharose beads. All bound, radiolabeled products are detected by scintillation counter.

Plates assayed are 96-well polypropylene (Greiner) and 96-well 1.2 μm hydrophilic PVDF filter plates (Millipore). Concentrations reported here are final assay concentrations: 10-100 μM compounds in DMSO (Burdick and Jackson), 5-10 nM Btk enzyme (His-tagged, full-length), 30 μM peptide substrate (Biotin-Aca-AAAEEIYGEI-NH₂), 100 μM ATP (Sigma), 8 mM imidazole (Sigma, pH 7.2), 8 mM glycerol-2-phosphate (Sigma), 200 μM EGTA (Roche Diagnostics), 1 mM MnCl₂ (Sigma), 20 mM MgCl₂ (Sigma), 0.1 mg/ml BSA (Sigma), 2 mM DTT (Sigma), 1 μCi $^{33}P$ ATP (Amersham), 20% streptavidin sepharose beads (Amersham), 50 mM EDTA (Gibco), 2 M NaCl (Gibco), 2 M NaCl w/1% phosphoric acid (Gibco), microscint-(Perkin Elmer).

IC₅₀ determinations are calculated from 10 data points per compound utilizing data pro-duced from a standard 96-well plate assay template. One control compound and seven unknown inhibitors were tested on each plate and each plate was run twice. Typically, compounds were diluted in half-log starting at 100 μM and ending at 3 nM. The control compound was staurosporine. Background was counted in the absence of peptide substrate. Total activity was determined in the presence of peptide substrate. The following protocol was used to determine Btk inhibition.

1) Sample preparation: The test compounds were diluted at half-log increments in assay buffer (imidazole, glycerol-2-phosphate, EGTA, MnCl₂, MgCl₂, BSA).
2) Bead preparation
 a.) rinse beads by centrifuging at 500 g
 b.) reconstitute the beads with PBS and EDTA to produce a 20% bead slurry
3) Pre-incubate reaction mix without substrate (assay buffer, DTT, ATP, $^{33}P$ ATP) and mix with substrate (assay buffer, DTT, ATP, $^{33}P$ ATP, peptide substrate) 30° C. for 15 min.
4) To start assay, pre-incubate 10 μL Btk in enzyme buffer (imidazole, glycerol-2-phosphate, BSA) and 10 μL of test compounds for 10 min at RT.
5) Add 30 μL reaction mixture without or with substrate to Btk and compounds.
6) Incubate 50 μL total assay mix for 30 min at 30° C.
7) Transfer 40 μL of assay to 150 μL bead slurry in filter plate to stop reaction.
8) Wash filter plate after 30 min, with following steps
 a. 3×250 μL NaCl
 b. 3×250 μL NaCl containing 1% phosphoric acid
 c. 1×250 μL H₂O
9) Dry plate for 1 h at 65° C. or overnight at RT
10) Add 50 μL microscint-20 and count $^{33}P$ cpm on scintillation counter.

Calculate percent activity from raw data in cpm percent activity=(sample−bkg)/(total activity−bkg)×100

Calculate IC₅₀ from percent activity, using one-site dose response sigmoidal model $y=A+((B-A)/(1+((x/C)^D)))$ x=cmpd conc, y=% activity, A=min, B=max, C=IC₅₀, D=1 (hill slope)

Inhibition of B Cell Activation in Whole Blood Measured by CD69 Expression

A procedure to test the ability of Btk inhibitors to suppress B cell receptor-mediated activation of B cells in human blood is as follows:

Human whole blood (HWB) is obtained from healthy volunteers, with the following restrictions: 24 hr drug-free, non-smokers. Blood is collected by venipuncture into Vacutainer tubes anticoagulated with sodium heparin. Test compounds are diluted to ten times the desired starting drug concentration in PBS (20×), followed by three-fold serial dilutions in 10% DMSO in PBS to produce a nine point dose-response curve. 5.5 µl of each compound dilution is added in duplicate to a 2 ml 96-well V bottom plate (Analytical Sales and Services, #59623-23); 5.5 µl of 10% DMSO in PBS is added to control and no-stimulus wells. HWB (100 µl) is added to each well, and after mixing the plates are incubated at 37 C, 5% $CO_2$, 100% humidity for 30 minutes. Goat F(ab')2 anti-human IgM (Southern Biotech, #2022-14) (10 µl of a 500 µg/ml solution, 50 µg/ml final concentration) is added to each well (except the no-stimulus wells) with mixing and the plates are incubated for an additional 20 hours.

At the end of the 20 hour incubation, samples are incubated with florescent-probe -labeled anti-bodies (15 µl PE Mouse anti-Human CD20, BD Pharmingen, #555623, and/or 20 µl APC Mouse anti-Human CD69, BD Pharmingen #555533) for 30 minutes, at 37 C, 5% $CO_2$, 100% humidity. Included are induced control, unstained and single stains for compensation adjustments and initial voltage settings. Samples are then lysed with 1 ml of 1× Pharmingen Lyse Buffer (BD Pharmingen #555899), and plates are centrifuged at 1800 rpm for minutes. Supernatants are removed via suction and the remaining pellets are lysed again with another 1 ml of 1× Pharmingen Lyse Buffer, and plates are spun down as before. Supernatants are aspirated and remaining pellets are washed in FACs buffer (PBS+1% FBS). After a final spin, the supernatants are removed and pellets are resuspended in 180l of FACs buffer. Samples are transferred to a 96 well plate suitable to be run on the HTS 96 well system on the BD LSR II flow cytometer.

Using appropriate excitation and emission wavelengths for the fluorophores used, data are acquired and percent positive cell values are obtained using Cell Quest Software. Results are initially analyzed by FACS analysis software (Flow Jo). The IC50 for test compounds is defined as the concentration which decreases by 50% the percentage of CD69-positive cells that are also CD20-positive after stimulation by anti-IgM (average of 8 control wells, after subtraction of the average of 8 wells for the no-stimulus background). The IC50 values are calculated using XLfit software version 3, equation 201.

Representative compound data for this assay are listed below in Table II. TABLE II.

TABLE II

| Compound | HWB IC50 (nM) |
| --- | --- |
| I-1 | 11 |
| I-2 | 5 |
| I-3 | 14 |
| I-4 | 95 |
| I-5 | 30 |
| I-6 | 77 |
| I-7 | 101 |
| I-8 | 27 |
| I-9 | 35 |
| I-10 | 9 |
| I-11 | 15 |
| I-12 | 28 |
| I-13 | 47 |
| I-14 | 6 |
| I-15 | 3 |
| I-16 | 28 |
| I-17 | 30 |
| I-18 | 29 |
| I-19 | 24 |
| I-20 | 74 |
| I-21 | 18 |
| I-22 | 44 |
| I-23 | 15 |
| I-24 | 6 |
| I-25 | 3 |
| I-26 | |
| I-27 | 62 |
| I-28 | 74 |
| I-29 | 162 |
| I-30 | 55 |
| I-31 | 36 |
| I-32 | 106 |
| I-33 | 212 |
| I-34 | 3500 |

Inhibition of B-cell Activation—B Cell FLIPR Assay in Ramos Cells

Inhibition of B-cell activation by compounds of the present invention is demonstrated by determining the effect of the test compounds on anti-IgM stimulated B cell responses.

The B cell FLIPR assay is a cell based functional method of determining the effect of potential inhibitors of the intracellular calcium increase from stimulation by an anti-IgM antibody. Ramos cells (human Burkitt's lymphoma cell line. ATCC-No. CRL-1596) were cultivated in Growth Media (described below). One day prior to assay, Ramos cells were resuspended in fresh growth media (same as above) and set at a concentration of $0.5 \times 10^6$/mL in tissue culture flasks. On day of assay, cells are counted and set at a concentration of $1 \times 10^6$/mLl in growth media supplemented with 1 µM FLUO-3AM (TefLabs Cat-No. 0116, prepared in anhydrous DMSO and 10% Pluronic acid) in a tissue culture flask, and incubated at 37° C. (4% $CO_2$) for one h. To remove extracellular dye, cells were collected by centrifugation (5 min, 1000 rpm), resuspended in FLIPR buffer (described below) at $1 \times 10^6$ cells/mL and then dispensed into 96-well poly-D-lysine coated black/clear plates (BD Cat-No. 356692) at $1 \times 10^5$ cells per well. Test compounds were added at various concentrations ranging from 100 µM to 0.03 µM (7 concentrations, details below), and allowed to incubate with cells for 30 min at RT. Ramos cell $Ca^{2+}$ signaling was stimulated by the addition of 10 µg/mL anti-IgM (Southern Biotech, Cat-No. 2020-01) and measured on a FLIPR (Molecular Devices, captures images of 96 well plates using a CCD camera with an argon laser at 480 nM excitation).

Media/Buffers:

Growth Medium: RPMI 1640 medium with L-glutamine (Invitrogen, Cat-No. 61870-010), 10% Fetal Bovine Serum (FBS, Summit Biotechnology Cat-No. FP-100-05); 1 mM Sodium Pyruvate (Invitrogen Cat. No. 11360-070).

FLIPR buffer: HBSS (Invitrogen, Cat-No. 141175-079), 2 mM $CaCl_2$ (Sigma Cat-No. C-4901), HEPES (Invitrogen, Cat-No. 15630-080), 2.5 mM Probenecid (Sigma, Cat-No. P-8761), 0.1% BSA (Sigma, Cat-No.A-7906), 111 mM Glucose (Sigma, Cat-No.G-7528)

Compound dilution details:

In order to achieve the highest final assay concentration of 100 μM, 24 μL of 10 mM compound stock solution (made in DMSO) is added directly to 576 μL of FLIPR buffer. The test compounds are diluted in FLIPR Buffer (using Biomek 2000 robotic pipettor) resulting in the following dilution scheme: vehicle, $1.00 \times 10^{-4}$ M, $1.00 \times 10^{-5}$, $3.16 \times 10^{-6}$, $1.00 \times 10^{-6}$, $3.16 \times 10^{-7}$, $1.00 \times 10^{-7}$, $3.16 \times 10^{-8}$.

Assay and Analysis:

Intracellular increases in calcium were reported using a max-min statistic (subtracting the resting baseline from the peak caused by addition of the stimulatory antibody using a Molecular Devices FLIPR control and statistic exporting software. The $IC_{50}$ was determined using a non-linear curve fit (GraphPad Prism software).

Mouse Collagen-Induced Arthritis (rCIA)

On day 0 mice are injected at the base of the tail or several spots on the back with an emulsion of Type II Collagen (i.d.) in Complete Freund's adjuvant (CFA). Following collagen immunization, animals will develop arthritis at around 21 to 35 days. The onset of arthritis is synchronized (boosted) by systemic administration of collagen in Incomplete Freund's adjuvant (IFA; i.d.) at day 21. Animals are examined daily after day 20 for any onset of mild arthritis (score of 1 or 2; see score description below) which is the signal to boost. Following boost, mice are scored and dosed with candidate therapeutic agents for the prescribed time (typically 2-3 weeks) and dosing frequency, daily (QD) or twice-daily (BID).

Rat Collagen-Induced Arthritis (rCIA)

On day 0, rats are injected with an emulsion of Bovine Type II Collagen in Incomplete Freund's adjuvant (IFA) is injected intradermally (i.d.) on several locations on the back. A booster injection of collagen emulsion is given around day 7, (i.d.) at the base of the tail or alternative sites on the back. Arthritis is generally observed 12-14 days after the initial collagen injection. Animals may be evaluated for the development of arthritis as described below (Evaluation of arthritis) from day 14 onwards. Animals are dosed with candidate therapeutic agents in a preventive fashion starting at the time of secondary challenge and for the prescribed time (typically 2-3 weeks) and dosing frequency, daily (QD) or twice-daily (BID).

Evaluation of Arthritis:

In both models, developing inflammation of the paws and limb joints is quantified using a scoring system that involves the assessment of the 4 paws following the criteria described below:

Scoring: 1=swelling and/or redness of paw or one digit.
2=swelling in two or more joints.
3=gross swelling of the paw with more than two joints involved.
4=severe arthritis of the entire paw and digits.

Evaluations are made on day 0 for baseline measurement and starting again at the first signs or swelling for up to three times per week until the end of the experiment. The arthritic index for each mouse is obtained by adding the four scores of the individual paws, giving a maximum score of 16 per animal.

Rat In Vivo Asthma Model

Male Brown-Norway rats are sensitized i.p. with 100 μg of OA (ovalbumin) in 0.2 ml alum once every week for three weeks (day 0, 7, and 14). On day 21 (one week following last sensitization), the rats are dosed q.d. with either vehicle or compound formulation subcutaneously 0.5 hour before OA aerosol challenge (1% OA for 45 minutes) and terminated 4 or 24 hours after challenge. At time of sacrifice, serum and plasma are collected from all animals for serology and PK, respectively. A tracheal cannula is inserted and the lungs are lavaged 3× with PBS. The BAL fluid is analyzed for total leukocyte number and differential leukocyte counts. Total leukocyte number in an aliquot of the cells (20-100 μl) is determined by Coulter Counter. For differential leukocyte counts, 50-200 μl of the sample is centrifuged in a Cytospin and the slide stained with Diff-Quik. The proportions of monocytes, eosinophils, neutrophils and lymphocytes are counted under light microscopy using standard morphological criteria and expressed as a percentage. Representative inhibitors of Btk show decreased total leukocyte count in the BAL of OA sensitized and challenged rats as compared to control levels.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A compound of Formula I,

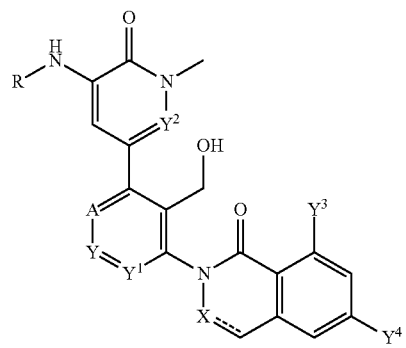

wherein:
⸺ is either a single or double bond;
each X is independently CH, $CH_2$, CHX', or N;
X' is lower alkyl;
R is H, —$R^1$, —$R^1$—$R^2$—$R^3$, —$R^1$—$R^3$, or —$R^2$—$R^3$;
$R^1$ is aryl, heteroaryl, bicyclic heteroaryl, cycloalkyl, heterocycloalkyl, or bicyclic heterocycle, each of which is optionally substituted with one or more lower alkyl, hydroxy, hydroxy lower alkyl, lower alkoxy, halo, nitro, amino, amido, cyano, oxo, or lower haloalkyl;
$R^2$ is —C(=O), —C(=O)O, —C(=O)$NR^{2'}$, —NHC(=O)O, —C($R^{2'}$)$_2$, —O, —S, —C(=NH)$NR^{2'}$, or —S(=O)$_2$;
each $R^{2'}$ is independently H or lower alkyl;
$R^3$ is H or $R^4$;
$R^4$ is lower alkyl, lower haloalkyl, lower alkoxy, amino, lower alkyl amino, cycloalkyl amino, lower dialkyl amino, aryl, arylalkyl, alkylaryl, heteroaryl, lower alkyl heteroaryl, heteroaryl lower alkyl, cycloalkyl, lower alkyl cycloalkyl, cycloalkyl lower alkyl, heterocycloalkyl, lower alkyl heterocycloalkyl, heterocycloalkyl lower alkyl, bicyclic cycloalkyl, bicyclic heterocycloalkyl, spirocycloalkyl, spiroheterocycloalkyl, or bicyclic spiroheterocycloalkyl, each of which is optionally substituted with one or more lower alkyl, halo, lower alkyl amino, lower dialkyl amino, hydroxy, hydroxy lower alkyl, lower alkoxy, lower alkanoyl, halo, nitro, amino, amido, acyl, cyano, oxo, sulfonyl, lower alkyl sulfonyl, guanidino, hydroxyl amino, carboxy, carbamoyl, carbamate, halo lower alkoxy, heterocycloalkyl, or halo lower alkyl, wherein two lower alkyl groups may together form a ring;

each of A, Y, and $Y^1$ is CH or N, with the proviso that at least one of A, Y, and $Y^1$ must be N;

$Y^2$ is CH or N;

$Y^3$ is H or F;

$Y^4$ is $Y^{4a}$, $Y^{4b}$, $Y^{4c}$, or $Y^{4d}$;

$Y^{4a}$ is H or halogen;

$Y^{4b}$ is lower alkyl, optionally substituted with one or more substituents selected from the group consisting of lower haloalkyl, halogen, hydroxy, amino, cyano, and lower alkoxy;

$Y^{4c}$ is lower cycloalkyl, optionally substituted with one or more substituents selected from the group consisting of lower alkyl, lower haloalkyl, halogen, hydroxy, amino, cyano, and lower alkoxy; and $Y^{4d}$ is amino, optionally substituted with one or more lower alkyl, alkoxy lower alkyl, or hydroxy lower alkyl;

or a pharmaceutically acceptable salt thereof.

2. The compound of claim 1, wherein ═ is a double bond and X is N.

3. The compound of claim 2, wherein A is CH, Y is CH, $Y^1$ is N, and $Y^2$ is N.

4. The compound of claim 3, wherein $Y^3$ is F.

5. The compound of claim 4, wherein $Y^4$ is tert-butyl.

6. The compound of claim 5, wherein R is $R^1$ and $R^1$ is 4,5,6,7-tetrahydro-pyrazolo[1,5-a]pyrazin-2-yl, optionally substituted with lower alkyl, heterocycloalkyl, cycloalkyl, or cycloalkyl lower alkyl.

7. The compound of claim 1 selected from the group consisting of:

6-tert-Butyl-8-fluoro-2-{3-hydroxymethyl-4-[1-methyl-5-(1'-methyl-1',2',3',4',5',6'-hexahydro-[3,4']bipyridinyl-6-ylamino)-6-oxo-1,6-dihydro-pyridazin-3-yl]-pyridin-2-yl}-2H-phthalazin-1-one;

6-tert-Butyl-8-fluoro-2-(3-hydroxymethyl-4-{1-methyl-5-[((S)-1-methyl-pyrrolidin-2-yl)-pyridin-2-ylamino]-6-oxo-1,6-dihydro-pyridazin-3-yl}-pyridin-2-yl)-2H-phthalazin-1-one;

6-tert-Butyl-8-fluoro-2-(3-hydroxymethyl-4-{1-methyl-5-[5-(morpholine-4-carbonyl)-pyridin-2-ylamino]-6-oxo-1,6-dihydro-pyridazin-3-yl}-pyridin-2-yl)-2H-phthalazin-1-one;

6-tert-Butyl-8-fluoro-2-{3-hydroxymethyl-4-[5-(5-methanesulfonyl-pyridin-2-ylamino)-1-methyl-6-oxo-1,6-dihydro-pyridazin-3-yl]-pyridin-2-yl}-2H-phthalazin-1-one;

6-{6-[2-(6-tert-Butyl-8-fluoro-1-oxo-1H-phthalazin-2-yl)-3-hydroxymethyl-pyridin-4-yl]-2-methyl-3-oxo-2,3-dihydro-pridazin-4-ylamino}-N,N-dimethyl-nicotinamide;

6-{6-[2-(6-Cyclopropyl-8-fluoro-1-oxo-1H-isoquinolin-2-yl)-3-hydroxymethyl-pridin-4-yl]-2-methyl-3-oxo-2,3-dihydro-pridazin-4-ylamino}-N,N-dimethyl-nicotinamide;

6-tert-Butyl-2-(3-hydroxymethyl-4-{1-methyl-5-[5-(morpholine-4-carbonyl)-pyridin-2-ylamino]-6-oxo-1,6-dihydro-pyridazin-3-yl}-pyridin-2-yl)-2H-phthalazin-1-one;

2'-(6-tert-Butyl-8-fluoro-1-oxo-1H-phthalazin-2-yl)-3'-hydroxymethyl-1-methyl-5-[5-(morpholine-4-carbonyl)-pyridin-2-ylamino]-1H-[3,4']bipyridinyl-6-one;

2'-(6-tert-Butyl-8-fluoro-1-oxo-1H-phthalazin-2-yl)-3'-hydroxymethyl-5-(5-methanesulfonyl-pyridin-2-ylamino)-1-methyl-1H-[3,4']bipyridinyl-6-one;

6-[2'-(6-tert-Butyl-8-fluoro-1-oxo-1H-phthalazin-2-yl)-3'-hydroxymethyl-1-methyl-6-oxo-1,6-dihydro-[3,4']bipyridinyl-5-ylamino]-N,N-dimethyl-nicotinamide;

2'-(6-Cyclopropyl-8-fluoro-1-oxo-1H-isoquinolin-2-yl)-3'-hydroxymethyl-1-methyl-5-[5-(morpholine-4-carbonyl)-pyridin-2-ylamino]-1H-[3,4']bipyridinyl-6-one;

6-tert-Butyl-2-(3-hydroxymethyl-4-{1-methyl-5-[5-((S)-1-methyl-pyrrolidin-2-yl)-pyridin-2-ylamino]-6-oxo-1,6-dihydro-pyridazin-3-yl}-pyridin-2-yl)-2H-phthalazin-1-one;

6-tert-Butyl-2-{3-hydroxymethyl-4-[1-methyl-5-(1'-methyl-1',2',3',4',5',6'-hexahydro-[3,4']bipyridinyl-6-ylamino)-6-oxo-1,6-dihydro-pyridazin-3-yl]-pyridin-2-yl}-2H-phthalazin-1-one;

6-tert-Butyl-2-{4-[5-(1'-ethyl-1',2',3',4',5',6'-hexahydro-[3,4']bipyridinyl-6-ylamino)-1-methyl-6-oxo-1,6-dihydro-pyridazin-3-yl]-3-hydroxymethyl-pyridin-2-yl}-8-fluoro-2H-phthalazin-1-one;

2-(4-{5-[5-(2-Azetidin-1-yl-1,1-dimethyl-ethoxy)-pyridin-2-ylamino]-1-methyl-6-oxo-1,6-dihydro-pyridazin-3-yl}-3-hydroxymethyl-pyridin-2-yl)-6-tert-butyl-8-fluoro-2H-phthalazin-1-one;

2-(4-{5-[5-(2-Azetidin-1-yl-1,1-dimethyl-ethoxy)-pyridin-2-ylamino]-1-methyl-6-oxo-1,6-dihydro-pyridazin-3-yl}-3-hydroxymethyl-pyridin-2-yl)-6-tert-butyl-2H-phthalazin-1-one;

2-{4-[5-(5-Azetidin-1-ylmethyl-1-methyl-1H-pyrazol-3-ylamino)-1-methyl-6-oxo-1,6-dihydro-pyridazin-3-yl]-3-hydroxymethyl-pyridin-2-yl}-6-tert-butyl-8-fluoro-2H-phthalazin-1-one;

6-tert-Butyl-8-fluoro-2-{3-hydroxymethyl-4-[1-methyl-5-(5-methyl-4,5,6,7-tetrahydro-pyrazolo[1,5-α]pyrazin-2-ylamino)-6-oxo-1,6-dihydro-pyridazin-3-yl]-pyridin-2-yl}-2H-phthalazin-1-one;

6-tert-Butyl-2-{3-hydroxymethyl-4-[1-methyl-5-(5-methyl-4,5,6,7-tetrahydro-pyrazolo[1,5-α]pyrazin-2-ylamino)-6-oxo-1,6-dihydro-pyridazin-3-yl]-pyridin-2-yl}-2H-phthalazin-1-one;

6-Cyclopropyl-8-fluoro-2-{3-hydroxymethyl-4-[1methyl-5-(5-methyl-4,5,6,7-tetrahydro-pyrazolo[1,5-α]pyrazin-2-ylamino)-6-oxo-1,6-dihydro-pyridazin-3-yl]-pyridin-2-yl}-2H-isoquinolin-1-one;

6-tert-Butyl-8-fluoro-2-{3-hydroxymethyl-4-[1-methyl-5-(5-oxetan-3-yl-4,5,6,7-tetrahydro-pyrazolo[1,5-α]pyrazin-2-ylamino)-6-oxo-1,6-dihydro-pyridazin-3-yl]-pyridin-2-yl}-2H-phthalazin-1-one;

6-tert-Butyl-2-{4-[5-(5-ethyl-4,5,6,7-tetrahydro-pyrazolo[1,5-α]pyrazin-2-ylamino)-1-methyl-6-oxo-1,6-dihydro-pyridazin-3-yl]-3-hydroxymethyl-pyridin-2-yl}-8-fluoro-2H-phthalazin-1-one;

6-tert-Butyl-8-fluoro-2-{3-hydroxymethyl-4-[1-methyl-5-(5-methyl-4,5,6,7-tetrahydro-pyrazolo[1,5-α]

pyrazin-2-ylamino)-6-oxo-1,6-dihydro-pyridazin-3-yl]-pyridin-2-yl}-2H-isoquinolin-1-one;

6-tert-Butyl-8-fluoro-2-{3-hydroxymethyl-4-[1-methyl-5-(5-oxetan-3-yl-4,5,6,7-tetrahydro-pyrazolo[1,5-α]pyrazin-2-ylamino)-6-oxo-1,6-dihydro-pyridazin-3-yl]-pyridin-2-yl}-2H-isoquinolin-1-one;

6-tert-Butyl-2-{4-[5-(5-ethyl-4,5,6,7-tetrahydro-pyrazolo[1,5-α]pyrazin-2-ylamino)-1-methyl-6-oxo-1,6-dihydro-pyridazin-3-yl]-3-hydroxymethyl-pyridin-2-yl}-8-fluoro-2H-isoquinolin-1-one;

6-tert-Butyl-2-{4-[5-(5-cyclopropylmethyl-4,5,6,7-tetrahydro-pyrazolo[1,5-α]pyrazin-2-ylamino)-1-methyl-6-oxo-1,6-dihydro-pyridazin-3-yl]-3-hydroxymethyl-pyridin-2-yl}-8-fluoro-2H-phthalazin-1-one;

6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-8-fluoro-2H-isoquinolin-1-one;

4-(6-tert-Butyl-8-fluoro-1-oxo-1H-phthalazin-2-yl)-3-hydroxymethyl-1'-methyl-5'-[5-(morpholine-4-carbonyl)-pyridin-2-ylamino]-1'H-[2,3']bipyridinyl-6'-one, 4-(6-tert-Butyl-8-fluoro-1-oxo-1H-phthalazin-2-yl)-3-hydroxymethyl-5'-(5-methanesulfonyl-pyridin-2-ylamino)-1'-methyl-1'H-[2,3']bipyridinyl-6'-one;

6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-8-fluoro-2H-phthalazin-1-one;

2-(8-Fluoro-2-{3-hydroxymethyl-4-[1-methyl-5-(5-methyl-4,5,6,7-tetrahydro-pyrazolo[1,5-α]pyrazin-2-ylamino)-6-oxo-1,6-dihydro-pyridazin-3-yl]-pyridin-2-yl}-1-oxo-1,2-dihydro-isoquinolin-6-yl)-2-methyl-propionitrile;

2{2-[4-(5-{5-[2-(3,3-Difluoro-azetidin-1-yl)-1,1-dimethyl-ethoxy]-pyridin-2-ylamino }-1-methyl-6-oxo-1,6-dihydro-pyridazin-3-yl)-3-hydroxymethyl-pyridin-2-yl]-8-fluoro-1-oxo-1,2-dihydro-isoquinolin-6-yl}-2-methyl-propionitrile;

6-tert-Butyl-2-[4-(5-{5-[2-(3,3-difluoro-azetidin-1-yl)-1,1-dimethyl-ethoxy]-pyridin-2-ylamino}-1-methyl-6-oxo-1,6-dihydro-pyridazin-3-yl)-3-hydroxymethyl-pyridin-2-yl]-2H-phthalazin-1-one; and 6-tert-Butyl-8-fluoro-2-{3-hydroxymethyl-4-[1-methyl-5-(5-methyl-5-oxy-4,5,6,7-tetrahydro-pyrazolo[1,5-α]pyrazin-2-ylamino)-6-oxo-1,6-dihydro-pyridazin-3-yl]-pyridin-2-yl}-2H-phthalazin-1-one.

8. A method for treating rheumatoid arthritis comprising administering to a patient in need thereof a therapeutically effective amount of the compound of claim 1.

9. A pharmaceutical composition comprising the compound of claim 1.

10. A pharmaceutical composition comprising the compound of claim 1, admixed with at least one pharmaceutically acceptable carrier, excipient or diluent.

* * * * *